United States Patent
Hayoz et al.

(10) Patent No.: US 8,652,752 B2
(45) Date of Patent: Feb. 18, 2014

(54) SULPHONIUM SALT INITIATORS

(75) Inventors: Pascal Hayoz, Hofstetten (CH); Hitoshi Yamato, Takarazuka (JP); Toshikage Asakura, Minoo (JP)

(73) Assignee: BASF SE, Ludwigshafen (DE)

( * ) Notice: Subject to any disclaimer, the term of this patent is extended or adjusted under 35 U.S.C. 154(b) by 345 days.

(21) Appl. No.: 12/681,785

(22) PCT Filed: Sep. 22, 2008

(86) PCT No.: PCT/EP2008/062587
§ 371 (c)(1),
(2), (4) Date: Aug. 11, 2010

(87) PCT Pub. No.: WO2009/047105
PCT Pub. Date: Apr. 16, 2009

(65) Prior Publication Data
US 2010/0297540 A1   Nov. 25, 2010

(30) Foreign Application Priority Data
Oct. 10, 2007  (EP) .................................. 07118194

(51) Int. Cl.
G03F 7/00       (2006.01)
G03F 7/004      (2006.01)
G03F 7/029      (2006.01)
C07D 333/00     (2006.01)
C07D 495/00     (2006.01)

(52) U.S. Cl.
USPC ............ 430/270.1; 430/913; 549/38; 549/43; 549/48; 549/49; 549/77

(58) Field of Classification Search
None
See application file for complete search history.

(56) References Cited

U.S. PATENT DOCUMENTS

| | | |
|---|---|---|
| 4,451,409 A | 5/1984 | Buske et al. |
| 4,694,029 A | 9/1987 | Land |
| 5,847,218 A | 12/1998 | Ohsawa |
| 2003/0235782 A1 | 12/2003 | Padmanaban et al. |
| 2005/0100819 A1 | 5/2005 | Fuji et al. |
| 2007/0060663 A1* | 3/2007 | Masumi .................. 522/31 |
| 2009/0197987 A1 | 8/2009 | Hayoz et al. |
| 2009/0208872 A1 | 8/2009 | Wolf et al. |
| 2010/0087563 A1 | 4/2010 | Hayoz et al. |

FOREIGN PATENT DOCUMENTS

| | | |
|---|---|---|
| EP | 0667338 | 8/1995 |
| EP | 1693704 A | 8/2006 |
| GB | 2061280 A | 9/1979 |
| JP | 07-252214 | 10/1995 |
| JP | 2007-250103 | 9/2007 |
| WO | 03/008404 A2 | 1/2003 |
| WO | 03/072567 A1 | 9/2003 |
| WO | 2007/003507 A1 | 1/2007 |
| WO | 2007/118794 A1 | 10/2007 |
| WO | 2008/040648 A1 | 4/2008 |

OTHER PUBLICATIONS

English language machine-generated translation for JP2007-250103 (19 pages); 2007.
Copending U.S. Appl. No. 12/445,756.
Copending U.S. Appl. No. 12/681,784.
Copending U.S. Appl. No. 12/681,786.
PAJ JP 08-311018.

* cited by examiner

*Primary Examiner* — Amanda C. Walke
(74) *Attorney, Agent, or Firm* — Shruti Costales

(57) ABSTRACT

Compounds of the Formula (I), wherein $L_1$, $L'_1$, $L''_1$, $L_2$, $L'_2$, $L''_2$, $L_3$, $L'_3$, $L''_3$, $L_4$, $L'_4$ and $L''_4$ for example are hydrogen or COT; R, R' and R" for example are hydrogen, $C_6$-$C_{12}$aryl or $C_3$-$C_{20}$heteroaryl; X, X' and X" for example are O, S, single bond, $NR_a$ or $NCOR_a$, T is for example hydrogen, $C_1$-$C_{20}$alkyl, $C_3$-$C_{12}$cycloalkyl, $C_2$-$C_{20}$alkenyl, $C_5$-$C_{12}$cycloalkenyl, $C_7$-$C_{18}$cycloalkylenaryl, $C_5$-$C_{18}$cycloalkylenheteroaryl, $C_6$-$C_{14}$aryl, providedthat at least one of R, R' or R" is unsubstituted or substituted $C_3$-$C_{20}$heteroaryl; and Y is an inorganic or organic anion; are suitable as photolatent acid generators.

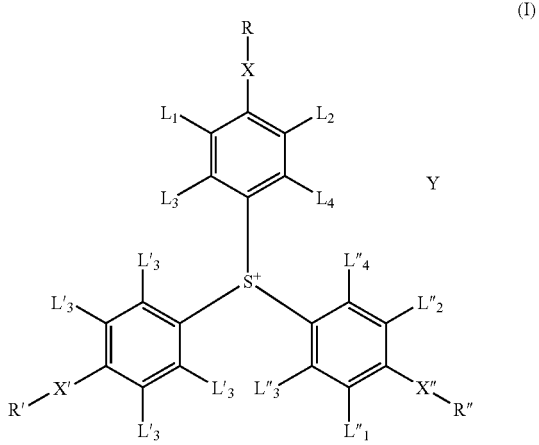

4 Claims, No Drawings

SULPHONIUM SALT INITIATORS

The invention pertains to novel sulphonium salt photoinitiators and their use in photocurable compositions.

Sulphonium salts are known in the art as photoinitiators. In GB 2061280 triarylsulphonium salts, comprising a phenlythio moiety, are disclosed. Other compounds of this type, inter alia with phenoxy groups, are known from U.S. Pat. Nos. 4,451,409, 4,694,029 and WO07/118794, for example tris(4-phenoxyphenyl)sulphonium hexafluorophosphate. WO 03/072567 and WO 03/008404 disclose sulphonium salts, wherein the sulphonium ion is located in a condensed ring system, for example in the thioxanthyl moiety. In JP08-311018-A a preparation process for sulphonium salts is disclosed as well as tris(4-butoxyphenyl)sulphonium and tris[4-(dimethylamino)phenyl]sulphonium cations. US 2003/0235782 and US 2005/0100819 provide sulphonium salts in photoresist applications. WO 07/003507 discloses sulphomium salts with a phenyl-COOR-moiety and WO08/040648 describe sulphonium salts with specific substituents.

One major problem of commercially available sulphonium salt photoinitiators is the formation of toxic and/or odorous break down products like diphenyl sulfide thioxanthone or benzene. In technique there is a need for effective cationic photoinitiators, which are reactive, in particular in both clear and pigmented coatings, thin and thick layers, with and without the addition of sensitizers as co-initiators, non toxic and which generate non toxic and odorless break down products and which further are low-yellowing.

It now has been found, that compounds of the formula I,

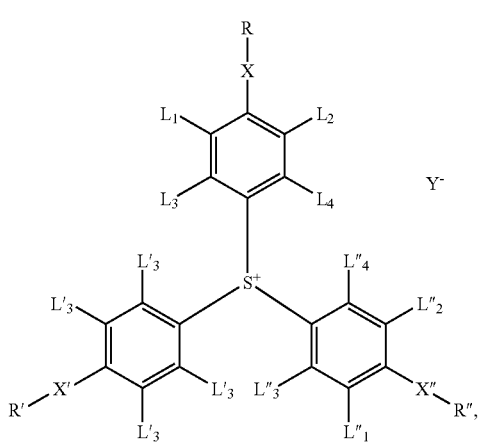

(I)

wherein $L_1$, $L'_1$, $L''_1$, $L_2$, $L'_2$, $L''_2$, $L_3$, $L'_3$, $L''_3$, $L_4$, $L'_4$ and $L''_4$ independently of one another are hydrogen, $R_1$, $OR_1$, $SR_1$, $NR_1R_2$, halogen, $NO_2$, CN, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$, COOT or COT;

R, R' and R" independently of each another are hydrogen, $C_6$-$C_{12}$aryl, $C_6$-$C_{12}$aryl substituted with at least one L, or are T, or are $C_3$-$C_{20}$heteroaryl or $C_3$-$C_{20}$heteroaryl substituted with at least one L, wherein the case that the $C_3$-$C_{20}$heteroaryl comprises an annelated benzene ring, the bond to the corresponding X, X' or X" is not located on said annelated ring;

X, X' and X" independently of each other are O, S, $CR_aR_b$, single bond, $NR_a$ or $NCOR_a$; provided that if X, X' or X" is 0, the corresponding R, R' or R" is not pyridinyl;

T is hydrogen, $C_1$-$C_{20}$alkyl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E; or T is $C_3$-$C_{12}$cycloalkyl, $C_3$-$C_{12}$cycloalkyl substituted by one or more D, $C_2$-$C_{12}$cycloalkyl interrupted by one or more O, CO, COO, CONR$_5$, S or NR$_5$, $C_2$-$C_{12}$cycloalkyl substituted by one or more D and interrupted by one or more O, CO, COO, CONR$_5$, S or NR$_5$; or T is $C_2$-$C_{20}$alkenyl, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl, $C_5$-$C_{12}$cycloalkenyl substituted by one or more D, $C_3$-$C_{12}$cycloalkenyl interrupted by one or more O, CO, COO, CONR$_5$, S or NR$_5$, $C_3$-$C_{12}$cycloalkenyl substituted by one or more D and interrupted by one or more O, CO, COO, CONR$_5$, S or NR$_5$; or T is $C_2$-$C_{20}$alkinyl, $C_2$-$C_{20}$alkinyl substituted by one or more D; $C_4$-$C_{20}$alkinyl interrupted by one or more O, CO, COO, CONR$_5$, S or NR$_5$, $C_4$-$C_{20}$alkinyl substituted by one or more D and interrupted by one or more O, CO, COO, CONR$_5$, S or NR$_5$; or T is $C_7$-$C_{12}$bicycloalkyl, $C_7$-$C_{12}$bicycloalkyl substituted by one or more D, $C_5$-$C_{12}$bicycloalkyl interrupted by one or more O, CO, COO, CONR$_5$, S or NR$_5$, $C_5$-$C_{12}$bicycloalkyl substituted by one or more D and interrupted by one or more O, CO, COO, CONR$_5$, S or NR$_5$; or T is $C_7$-$C_{12}$bicycloalkenyl, $C_7$-$C_{12}$bicycloalkenyl substituted by one or more D, $C_5$-$C_{12}$ bicycloalkenyl interrupted by one or more O, CO, COO, CONR$_5$, S or NR$_5$, $C_5$-$C_{12}$bicycloalkenyl substituted by one or more D and interrupted by one or more O, CO, COO, CONR$_5$, S or NR$_5$; or T is $C_{10}$-$C_{20}$tricycloalkyl, $C_6$-$C_{12}$tricycloalkyl substituted by one or more D, $C_7$-$C_{15}$tricycloalkyl interrupted by one or more O, CO, COO, CONR$_5$, S or NR$_5$, $C_7$-$C_{15}$tricycloalkyl substituted by one or more D and interrupted by one or more O, CO, COO, CONR$_5$, S or NR$_5$; or T is $C_8$-$C_{18}$cycloalkylenaryl, $C_8$-$C_{18}$cycloalkylenaryl substituted by one or more D, $C_7$-$C_{18}$cycloalkylenaryl interrupted by one or more O, CO, COO, CONR$_5$, S or NR$_5$, $C_7$-$C_{18}$cycloalkylenaryl substituted by one or more D and interrupted by one or more O, CO, COO, CONR$_5$, S or NR$_5$; or T is $C_7$-$C_{18}$cycloalkylenheteroaryl, $C_7$-$C_{18}$cycloalkylenheteroaryl substituted by one or more D, $C_6$-$C_{18}$cycloalkylenheteroaryl interrupted by one or more O, CO, COO, CONR$_5$, S or NR$_5$, $C_6$-$C_{18}$cycloalkylenheteroaryl substituted by one or more D and interrupted by one or more O, CO, COO, CONR$_5$, S or NR$_5$; or T is $C_6$-$C_{14}$aryl, $C_6$-$C_{14}$aryl substituted by one or more D, $C_3$-$C_{12}$heteroaryl or $C_3$-$C_{12}$heteroaryl substituted by one or more D;

$R_1$, $R_2$, $R_a$ and $R_b$ independently of one another have the meaning of T;

D is hydrogen, $R_5$, $OR_5$, $SR_5$, $NR_5R_6$, halogen, $NO_2$, CN, O-glycidyl, O-vinyl, O-allyl, $COR_5$, $NR_5COR_6$, $COOR_5$, $OCOR_5$, $CONR_5R_6$, $OCOOR_5$, $OCONR_5R_6$, $NR_5COOR_6$, $SO_3H$, $SO_3M$, =O, $C_6$-$C_{14}$aryl, $C_6$-$C_{14}$aryl substituted by one or more $R_{12}$, $OR_{12}$, halogen, $SR_{12}$, $NO_2$, CN, $COR_{12}$, $NR_{12}COR_{13}$, $COOR_{12}$, $OCOR_{12}$, $CONR_{12}R_{13}$, $OCOOR_{12}$, $OCONR_{12}R_{13}$, $NR_{12}COOR_{13}$ or $SO_3H$, $C_3$-$C_{12}$heteroaryl, $C_3$-$C_{12}$heteroaryl substituted by one or more $R_{12}$, $OR_{12}$, halogen, $SR_{12}$, $NO_2$, CN, $COR_{12}$, $NR_{12}COR_{13}$, $COOR_{12}$, $OCOR_{12}$, $CONR_{12}R_{13}$, $OCOOR_{12}$, $OCONR_{12}R_{13}$, $NR_{12}COOR_{13}$ or $SO_3H$; or is $C_3$-$C_{12}$cycloalkyl, $C_3$-$C_{12}$cycloalkyl substituted by one or more $R_{14}$, $C_2$-$C_{12}$cycloalkyl interrupted by one or more O, CO, COO, CONR$_5$, S or NR$_5$, $C_2$-$C_{12}$cycloalkyl substituted by one or more $R_{14}$ and interrupted by one or more O, CO, COO, CONR$_5$, S or NR$_5$; or D is $C_5$-$C_{12}$cycloalkenyl, $C_5$-$C_{12}$cycloalkenyl substituted by one or more $R_{14}$, $C_3$-$C_{12}$cycloalkenyl interrupted by one or more O, CO, COO, CONR$_5$, S or NR$_5$, $C_3$-$C_{12}$cycloalkenyl substituted by one or more $R_{14}$ and interrupted by one or more O, CO, COO, CONR$_5$, S or NR$_5$; or D is $C_7$-$C_{12}$bicycloalkyl, $C_7$-$C_{12}$bicycloalkyl substituted by one or more $R_{14}$, $C_5$-$C_{12}$bicycloalkyl interrupted by one or more O, CO, COO, CONR$_5$, S or NR$_5$, $C_5$-$C_{12}$bicycloalkyl substituted by one or more $R_{14}$ and interrupted by one or more O, CO, COO, CONR$_5$, S or NR$_5$; or D is $C_7$-$C_{12}$bicycloalkenyl, $C_7$-$C_{12}$bicycloalkenyl substituted by one or more $R_{14}$, $C_5$-$C_{12}$bicycloalkenyl interrupted by one or more O, CO, COO, CONR$_5$, S or NR$_5$, $C_5$-$C_{12}$bicycloalkenyl substituted by one or more $R_{14}$ and interrupted by one or more O, CO, COO, CONR$_5$, S or NR$_5$; or D is $C_{10}$-$C_{20}$tricycloalkyl, $C_{10}$-$C_{20}$tricycloalkyl substituted by one or more $R_{14}$, $C_7$-$C_{15}$tricycloalkyl interrupted by one or more O, CO, COO, CONR$_5$, S or NR$_5$, $C_6$-$C_{12}$tricycloalkyl substituted by one or more $R_{14}$ and interrupted by one or more O, CO, COO, CONR$_5$, S or NR$_5$; or is $C_8$-$C_{18}$cycloalkylenaryl, $C_8$-$C_{18}$cycloalkylenaryl substituted by one or more $R_{14}$, $C_7$-$C_{18}$cycloalkylenaryl interrupted by one or more O, CO, COO, CONR$_5$, S or NR$_5$, $C_7$-$C_{18}$cycloalkylenaryl substituted by one or more $R_{14}$ and interrupted by one or more O, CO, COO, CONR$_5$, S or NR$_5$; or $C_7$-$C_{18}$cycloalkylenheteroaryl, $C_7$-$C_{18}$cycloalkylenheteroaryl substituted by one or more $R_{14}$, $C_8$-$C_{18}$cycloalkylenheteroaryl interrupted by one or more O, CO, COO, CONR$_5$, S or NR$_5$, $C_8$-$C_{18}$cycloalkylenheteroaryl substituted by one or more $R_{14}$ and interrupted by one or more O, CO, COO, CONR$_5$, S or NR$_5$;

E is O, S, COO, OCO, CO, NR$_5$, NCOR$_5$, NR$_5$CO, CONR$_5$, OCOO, OCONR$_5$, NR$_5$COO, SO$_2$, SO, CR$_5$=CR$_6$ or

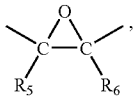

is $C_6$-$C_{14}$arylene, $C_3$-$C_{12}$heteroarylene, $C_3$-$C_{12}$cycloalkylene, $C_3$-$C_{12}$cycloalkylene substituted by one or more $R_{14}$, $C_2$-$C_{12}$cycloalkylene interrupted by one or more O, CO, COO, CONR$_5$, S or NR$_5$, $C_2$-$C_{12}$cycloalkylene substituted by one or more $R_{14}$ and interrupted by one or more O, CO, COO, CONR$_5$, S or NR$_5$; or E is $C_5$-$C_{12}$cycloalkenylene, $C_5$-$C_{12}$cycloalkenylene substituted by one or more $R_{14}$, $C_3$-$C_{12}$cycloalkenylene interrupted by one or more O, CO, COO, CONR$_5$, S or NR$_5$, $C_3$-$C_{12}$cycloalkenylene substituted by one or more $R_{14}$ and interrupted by one or more O, CO, COO, CONR$_5$, S or NR$_5$; or E is $C_7$-$C_{12}$bicycloalkylene, $C_7$-$C_{12}$bicycloalkylene substituted by one or more $R_{14}$, $C_5$-$C_{12}$bicycloalkylene interrupted by one or more O, CO, COO, CONR$_5$, S or NR$_5$, $C_5$-$C_{12}$bicycloalkylene substituted by one or more $R_{14}$ and interrupted by one or more O, CO, COO, CONR$_5$, S or NR$_5$; or E is $C_7$-$C_{12}$bicycloalkenylene, $C_7$-$C_{12}$bicycloalkenylene substituted by one or more $R_{14}$, $C_5$-$C_{12}$bicycloalkenylene interrupted by one or more O, CO, COO, CONR$_5$, S or NR$_5$, $C_5$-$C_{12}$bicycloalkenylene substituted by one or more $R_{14}$ and interrupted by one or more O, CO, COO, CONR$_5$, S or NR$_5$; or E is $C_{10}$-$C_{20}$tricycloalkylene, $C_{10}$-$C_{20}$tricycloalkylene substituted by one or more $R_{14}$, $C_7$-$C_{15}$tricycloalkylene interrupted by one or more O, CO, COO, CONR$_5$, S or NR$_5$, $C_7$-$C_{15}$tricycloalkylene substituted by one or more $R_{14}$ and interrupted by one or more O, CO, COO, CONR$_5$, S or NR$_5$; or E is $C_8$-$C_{18}$cycloalkylenarylene, $C_8$-$C_{18}$cycloalkylenarylene substituted by one or more $R_{14}$, $C_7$-$C_{18}$cycloalkylenarylene interrupted by one or more O, CO, COO, CONR$_5$, S or NR$_5$, $C_7$-$C_{18}$cycloalkylenarylene substituted by one or more $R_{14}$ and interrupted by one or more O, CO, COO, CONR$_5$, S or NR$_5$; or E is $C_7$-$C_{18}$cycloalkylenheteroarylene, $C_7$-$C_{18}$cycloalkylenheteroarylene substituted by one or more $R_{14}$, $C_6$-$C_{18}$cycloalkylenheteroarylene interrupted by one or more O, CO, COO, CONR$_5$, S or NR$_5$, $C_6$-$C_{18}$cycloalkylenheteroarylene substituted by one or more $R_{14}$ and interrupted by one or more O, CO, COO, CONR$_5$, S or NR$_5$;

$R_5$ and $R_6$ independently of one another are hydrogen, a covalent bond to another substituent to form a ring, $C_1$-$C_6$alkylene to form a ring with another substituent, $C_1$-$C_{12}$alkyl, phenyl or phenyl substituted by $C_1$-$C_4$alkyl and/or $C_1$-$C_4$alkoxy;

$R_7$, $R_8$, $R_9$, $R_{10}$ and $R_{11}$ independently of one another are hydrogen, $C_1$-$C_{12}$alkyl, $C_1$-$C_{12}$alkoxy, phenyl, phenoxy, substituted phenyl or substituted phenoxy;

$R_{12}$ and $R_{13}$ independently of one another are hydrogen, $C_1$-$C_{12}$alkyl, $C_5$-$C_{12}$cycloalkyl or phenyl;

$R_{14}$ is hydrogen, $C_1$-$C_{12}$alkyl, $C_5$-$C_{12}$cycloalkyl, $C_1$-$C_{12}$alkoxy, $C_2$-$C_{12}$cycloalkyloxy, phenyl or halogen;

n is an integer from 1 to 100;

Y is an inorganic or organic anion;

M is an inorganic or organic cation; and provided that at least one of R, R' or R" is $C_3$-$C_{20}$heteroaryl or $C_3$-$C_{20}$heteroaryl substituted with at least one L; are suitable as photoinitiators.

Said compounds excel at a good reactivity in combination with low yellowing, low odor and good solubility in the photocurable formulation. The photolatent acid sulphonium salt compounds of formula I exhibit a very satisfactory reactivity combined with good solubility and low yellowing properties. A very important advantage in view of environmental aspects is the fact that the compounds according to the present invention do not release benzene or thioxanthone.

Specific compounds of the formula I according to the present invention are such, wherein at least two of R, R' or R" independently of one another are $C_3$-$C_{20}$heteroaryl or $C_3$-$C_{20}$heteroaryl substituted with at least one L.

Interesting are compounds

R, R' and R" are identical; and L, L' and L" are identical; and $L_1$, $L'_1$ and $L''_1$ are identical; and $L_2$, $L'_2$ and $L''_2$ are identical; and $L_3$, $L'_3$ and $L''_3$ are identical; and $L_4$, $L'_4$ and $L''_4$ are identical and X, X' and X" are identical, namely a compound of the formula Ia

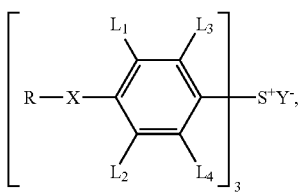

(Ia)

wherein R, X, Y, $L_1$, $L_2$, $L_3$ and $L_4$ are defined above.

$L_1$, $L'_1$, $L''_1$, $L_2$, $L'_2$, $L''_2$, $L_3$, $L'_3$, $L''_3$, $L_4$, $L'_4$ and $L''_4$ are for example hydrogen, $R_1$, $OR_1$, $SR_1$, $NR_1R_2$, halogen, $NO_2$, CN, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$, COOT or COT;

$R_1$ has one of the meanings given for T, as defined above.

Preferably $L_1$, $L'_1$, $L''_1$, $L_2$, $L'_2$, $L''_2$, $L_3$, $L'_3$, $L''_3$, $L_4$, $L'_4$ and $L''_4$ independently of one another are hydrogen, $R_1$, $OR_1$, $SR_1$, halogen, $NO_2$, CN or $COR_1$. Particular preferred $L_1$, $L'_1$, $L''_1$, $L_2$, $L'_2$, $L''_2$, $L_3$, $L'_3$, $L''_3$, $L_4$, $L'_4$ and $L''_4$ independently of one another are hydrogen, $R_1$, $OR_1$ or halogen. Even more preferred are compounds wherein $L_1$, $L'_1$, $L''_1$, $L_2$, $L'_2$, $L''_2$ are independently of each other hydrogen, $R_1$, $OR_1$ or halogen; and $L_3$, $L'_3$, $L''_3$, $L_4$, $L'_4$ and $L''_4$ are hydrogen. Most preferred are compounds wherein $L_1$, $L'_1$, $L''_1$, $L_2$, $L'_2$, $L''_2$ are independently of each other hydrogen, $C_1$-$C_6$alkyl, $C_5$-$C_6$cycloalkyl, $C_1$-$C_6$alkoxy or phenyl; and $L_3$, $L'_3$, $L''_3$, $L_4$, $L'_4$ and $L''_4$ are hydrogen. In other preferred compounds $L_1$, $L'_1$, $L''_1$, $L_2$, $L'_2$, $L''_2$ are independently of each other $C_1$-$C_6$alkyl, $C_5$-$C_6$cycloalkyl, $C_1$-$C_6$alkoxy or phenyl; and $L_3$, $L'_3$, $L''_3$, $L_4$, $L'_4$ and $L''_4$ are hydrogen.

$L_3$, $L'_3$, $L''_3$, $L_4$, $L'_4$ and $L''_4$ preferably are hydrogen.

X, X' and X" preferably are O, S or $CR_aR_b$, in particular O or S, especially S.

R, R' and R" are for example hydrogen, $C_6$-$C_{12}$aryl, $C_6$-$C_{12}$aryl substituted with at least one L, or are T, or are $C_3$-$C_{20}$heteroaryl or $C_3$-$C_{20}$heteroaryl substituted with at least one L, wherein the case that the $C_3$-$C_{20}$heteroaryl comprises an annelated benzene ring, the bond to the corresponding X, X' or X" is not located on said annelated ring.

In the case that R, R' and R" as $C_3$-$C_{20}$heteroaryl comprise an annelated benzene ring, the bond to the corresponding X, X' or X" is not located on said annelated ring. That is, for example structures like the following are formed

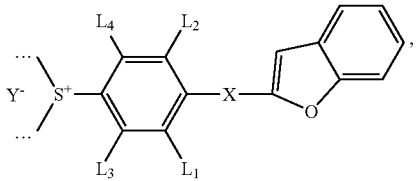

whereas structures like

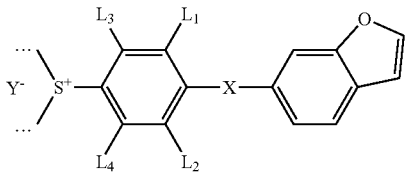

are not covered by the present claims

Especially R, R' and R" are for example hydrogen, $C_6$-$C_{12}$aryl, or are $C_3$-$C_{20}$heteroaryl or $C_3$-$C_{20}$heteroaryl substituted with at least one L, wherein the case that the $C_3$-$C_{20}$heteroaryl comprises an annelated benzene ring, the bond to the corresponding X, X' or X" is not located on said annelated ring.

Preferred R, R' and R" are $C_3$-$C_{20}$heteroaryl unsubstituted or substituted as defined above, in particular by $C_1$-$C_{20}$alkyl.

In the context of the present invention a group that is defined to be substituted is meant to be substituted at least once, that is it bears one or more substituents. This refers in particular to substituted aryl or heteroaryl.

D is for example hydrogen, $R_5$, $OR_5$, $SR_5$, halogen, $NO_2$, CN, O-glycidyl, O-vinyl, O-allyl, $COR_5$, $COOR_5$, $OCOR_5$, $OCOOR_5$, $SO_3H$, $SO_3M$, =O, $C_6$-$C_{14}$aryl, $C_6$-$C_{14}$aryl substituted by one or more $R_{12}$, $OR_{12}$, halogen, $NO_2$, $SR_{12}$, $SO_3H$ or CN, $C_3$-$C_{12}$heteroaryl, $C_3$-$C_{12}$heteroaryl substituted by one or more $R_{12}$, $OR_{12}$, halogen, $NO_2$, $SR_{12}$, $SO_3H$ or CN; or D is is $C_3$-$C_{12}$cycloalkyl, $C_3$-$C_{12}$cycloalkyl substituted by one or more $R_{14}$, $C_2$-$C_{12}$cycloalkyl interrupted by one or more O, CO, COO or S, $C_2$-$C_{12}$cycloalkyl substituted by one or more $R_{14}$ and interrupted by one or more O, CO, COO or S; or D is $C_5$-$C_{12}$cycloalkenyl, $C_5$-$C_{12}$cycloalkenyl substituted by one or more $R_{14}$, $C_3$-$C_{12}$cycloalkenyl interrupted by one or more O, CO, COO or S, $C_3$-$C_{12}$cycloalkenyl substituted by one or more $R_{14}$ and interrupted by one or more O, CO, COO or S; or D is $C_7$-$C_{12}$bicycloalkyl, $C_7$-$C_{12}$bicycloalkyl substituted by one or more $R_{14}$, $C_5$-$C_{12}$bicycloalkyl interrupted by one or more O O, CO, COO or S, $C_5$-$C_{12}$bicycloalkyl substituted by one or more $R_{14}$ and interrupted by one or more O, CO, COO or S; or D is $C_7$-$C_{12}$bicycloalkenyl, $C_7$-$C_{12}$bicycloalkenyl substituted by one or more $R_{14}$, $C_5$-$C_{12}$bicycloalkenyl interrupted by one or more O, CO, COO or S, $C_5$-$C_{12}$bicycloalkenyl substituted by one or more $R_{14}$ and interrupted by one or more O, CO, COO or S; or D is $C_8$-$C_{18}$cycloalkylenaryl, $C_8$-$C_{18}$cycloalkylenaryl substituted by one or more $R_{14}$, $C_7$-$C_{18}$cycloalkylenaryl interrupted by one or more O, CO, COO or S, $C_7$-$C_{18}$cycloalkylenaryl substituted by one or more $R_{14}$ and interrupted by one or more O, CO, COO or S; or $C_7$-$C_{18}$cycloalkylenheteroaryl, $C_7$-$C_{18}$cycloalkylenheteroaryl substituted by one or more $R_{14}$, $C_8$-$C_{18}$cycloalkylenheteroaryl interrupted by one or more O, CO, COO or S, $C_8$-$C_{18}$cycloalkylenheteroaryl substituted by one or more $R_{14}$ and interrupted by one or more O, CO, COO or S.

especially D is hydrogen, $R_5$, $OR_5$, $SR_5$, halogen, $NO_2$, CN, O-glycidyl, O-vinyl, O-allyl, $COR_5$, $COOR_5$, $OCOR_5$, $OCOOR_5$, $SO_3H$, $SO_3M$, =O, $C_6$-$C_{14}$aryl, $C_6$-$C_{14}$aryl substituted by one or more $R_{12}$, $OR_{12}$, halogen, $NO_2$, $SR_{12}$, $SO_3H$ or CN, $C_3$-$C_{12}$heteroaryl, $C_3$-$C_{12}$heteroaryl substituted by one or more $R_{12}$, $OR_{12}$, halogen, $NO_2$, $SR_{12}$, $SO_3H$ or CN; or D is is $C_3$-$C_{12}$cycloalkyl, $C_3$-$C_{12}$cycloalkyl substituted by one or more $R_{14}$, $C_2$-$C_{12}$cycloalkyl interrupted by one or more O, CO, COO or S, $C_2$-$C_{12}$cycloalkyl substituted by one or more $R_{14}$ and interrupted by one or more O, CO, COO or S; or D is $C_5$-$C_{12}$cycloalkenyl, $C_5$-$C_{12}$cycloalkenyl substituted by one or more $R_{14}$, $C_3$-$C_{12}$cycloalkenyl interrupted by one or more O, CO, COO or S, $C_3$-$C_{12}$cycloalkenyl substituted by one or more $R_{14}$ and interrupted by one or more O, CO, COO or S; or D is $C_7$-$C_{12}$bicycloalkyl, $C_7$-$C_{12}$bicycloalkyl substituted by one or more $R_{14}$, $C_5$-$C_{12}$bicycloalkyl interrupted by one or more O O, CO, COO or S, $C_5$-$C_{12}$bicycloalkyl substituted by one or more $R_{14}$ and interrupted by one or more O, CO, COO or S; or D is $C_7$-$C_{12}$bicycloalkenyl, $C_7$-$C_{12}$bicycloalkenyl substituted by one or more $R_{14}$, $C_5$-$C_{12}$bicycloalkenyl interrupted by one or more O, CO, COO or S, $C_5$-$C_{12}$bicycloalkenyl substituted by one or more $R_{14}$ and interrupted by one or more O, CO, COO or S.

preferred D is hydrogen or OH.

E is for example O, S, COO, OCO, CO, OCOO, $SO_2$, SO, $CR_5$=$CR_6$ or

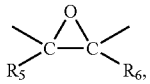

is $C_6$-$C_{14}$arylene, $C_3$-$C_{12}$heteroarylene, $C_3$-$C_{12}$cycloalkylene, $C_3$-$C_{12}$cycloalkylene substituted by one or more $R_{14}$, $C_2$-$C_{12}$cycloalkylene interrupted by one or more O, CO, COO or S, $C_2$-$C_{12}$cycloalkylene substituted by one or more $R_{14}$ and interrupted by one or more O, CO, COO or S; or E is $C_5$-$C_{12}$cycloalkenylene, $C_5$-$C_{12}$cycloalkenylene substituted by one or more $R_{14}$, $C_3$-$C_{12}$cycloalkenylene interrupted by one or more O, CO, COO or S, $C_3$-$C_{12}$cycloalkenylene substituted by one or more $R_{14}$ and interrupted by one or more O, CO, COO or S; or E is $C_7$-$C_{12}$bicycloalkylene, $C_7$-$C_{12}$bicycloalkylene substituted by one or more $R_{14}$, $C_5$-$C_{12}$bicycloalkylene interrupted by one or more O, CO, COO or S, $C_5$-$C_{12}$bicycloalkylene substituted by one or more $R_{14}$ and interrupted by one or more O, CO, COO or S; or E is $C_7$-$C_{12}$bicycloalkenylene, $C_7$-$C_{12}$bicycloalkenylene substituted by one or more $R_{14}$, $C_5$-$C_{12}$bicycloalkenylene interrupted by one or more O, CO, COO or S, $C_5$-$C_{12}$bicycloalkenylene substituted by one or more $R_{14}$ and interrupted by one or more O, CO, COO or S; or E is $C_8$-$C_{18}$cycloalkylenarylene, $C_8$-$C_{18}$cycloalkylenarylene substituted by one or more $R_{14}$, $C_7$-$C_{18}$cycloalkylenarylene interrupted by one or more O, CO, COO or S, $C_7$-$C_{18}$cycloalkylenarylene substituted by one or more $R_{14}$ and interrupted by one or more O, CO, COO or S; or E is $C_7$-$C_{18}$cycloalkylenheteroarylene, $C_7$-$C_{18}$cycloalkylenheteroarylene substituted by one or more $R_{14}$, $C_6$-$C_{18}$cycloalkylenheteroarylene interrupted by one or more O, CO, COO or S, $C_6$-$C_{18}$cycloalkylenheteroarylene substituted by one or more $R_{14}$ and interrupted by one or more O, CO, COO or S;

Especially E is O, S, COO, OCO, CO, OCOO, $SO_2$, SO, $CR_5$=$CR_6$ or

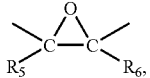

is $C_6$-$C_{14}$arylene, $C_3$-$C_{12}$heteroarylene, $C_3$-$C_{12}$cycloalkylene, $C_3$-$C_{12}$cycloalkylene substituted by one or more $C_1$-$C_{12}$alkyl or $C_1$-$C_{12}$alkoxy, $C_2$-$C_{12}$cycloalkylene interrupted by one or more O, CO, COO or S, $C_2$-$C_{12}$cycloalkylene substituted by one or more $C_1$-$C_{12}$alkyl or $C_1$-$C_{12}$alkoxy and interrupted by one or more O, CO, COO or S; or E is $C_5$-$C_{12}$cycloalkenylene, $C_5$-$C_{12}$cycloalkenylene substituted by one or more $C_1$-$C_{12}$alkyl or $C_1$-$C_{12}$alkoxy, $C_3$-$C_{12}$cycloalkenylene interrupted by one or more O, CO, COO or S, $C_3$-$C_{12}$cycloalkenylene substituted by one or more $C_1$-$C_{12}$alkyl or $C_1$-$C_{12}$alkoxy and interrupted by one or more O, CO, COO or S; or E is $C_7$-$C_{12}$bicycloalkylene, $C_7$-$C_{12}$bicycloalkylene substituted by one or more $C_1$-$C_{12}$alkyl or $C_1$-$C_{12}$alkoxy, $C_5$-$C_{12}$bicycloalkylene interrupted by one or more O, CO, COO or S, $C_5$-$C_{12}$bicycloalkylene substituted by one or more $C_1$-$C_{12}$alkyl or $C_1$-$C_{12}$alkoxy and interrupted by one or more O, CO, COO or S; or E is $C_7$-$C_{12}$bicycloalkenylene, $C_7$-$C_{12}$bicycloalkenylene substituted by one or more $C_1$-$C_{12}$alkyl or $C_1$-$C_{12}$alkoxy, $C_5$-$C_{12}$bicycloalkenylene interrupted by one or more O, CO, COO or S, $C_5$-$C_{12}$bicycloalkenylene substituted by one or more $C_1$-$C_{12}$alkyl or $C_1$-$C_{12}$alkoxy and interrupted by one or more O, CO, COO or S.

Preferred E is O, S or $CR_5$=$CR_6$.

$R_{14}$ preferably is $C_1$-$C_{12}$alkyl or $C_1$-$C_{12}$alkoxy.

$C_1$-$C_{20}$alkyl is linear or branched and is, for example, $C_1$-$C_{18}$-, $C_1$-$C_{14}$-, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_1$-$C_{18}$alkyl, $C_1$-$C_{14}$alkyl, $C_1$-$C_{12}$alkyl, $C_1$-$C_8$alkyl, $C_1$-$C_6$alkyl and $C_1$-$C_4$alkyl have the same meanings as given above for $C_1$-$C_{20}$alkyl up to the corresponding number of C-atoms.

$C_2$-$C_{20}$alkyl interrupted by one or more E, is for example interrupted 1-9, 1-7 or once or twice by E. In case the groups are interrupted by more than one E, said E preferably are seperated from one another by at least one carbon atom, i.e. the E preferably are non-consecutive, in particular if E denotes O. Examples are the following structural units —$CH_2$—O—$CH_3$, —$CH_2CH_2$—O—$CH_2CH_3$, —[$CH_2CH_2O$]$_y$—$CH_3$, with y=1-9, —($CH_2CH_2O$)$_7$$CH_2CH_3$, —$CH_2$—CH($CH_3$)—O—$CH_2$—$CH_2CH_3$, —$CH_2$—CH($CH_3$)—O—$CH_2CH_3$, —$CH_2$—S—$CH_3$, —$CH_2CH_2$—S—$CH_2CH_3$, —$CH_2$—(CO)O—$CH_3$, —$CH_2$—(CO)—$CH_3$, —$CH_2$—$NR_5$—$CH_3$, —$CH_2CH_2$—$NR_5$—$CH_2CH_3$, —$CH_2$—COO—$CH_2$—$CH_2$—O—$CH_3$ etc.

$C_2$-$C_{10}$alkenyl is mono or polyunsaturated, linear or branched and is for example $C_2$-$C_8$-, $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_5$-$C_{12}$cycloalkyl is for example cyclopentyl, cyclohexyl, cyclooctyl, cyclo-dodecyl, especially cyclopentyl and cyclohexyl, preferably cyclohexyl. $C_3$-$C_{12}$Cycloalkyl in the context of the present application is to be understood as alkyl which at least comprises one ring. For example methyl-cyclopentyl, cyclopentyl, cyclohexyl, methyl- or dimethylcyclohexyl, cyclooctyl, especially cyclopentyl and cyclohexyl, preferably cyclohexyl are also meant. Further examples are structures like

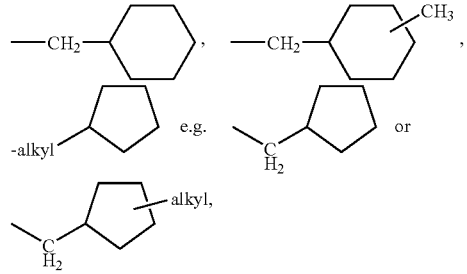

$C_2$-$C_{12}$cycloalkyl interupted by one or more E with E defined as O, S, COO, OCO, CO, $NR_2$, $NCOR_2$, $NR_2CO$, $CONR_2$, OCOO, $OCONR_2$, $NR_2COO$, $SO_2$, SO, phenylene, $C_4$-$C_6$cycloalkylene, $CR_2$=$CR_3$ or

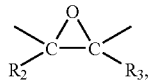

is for example

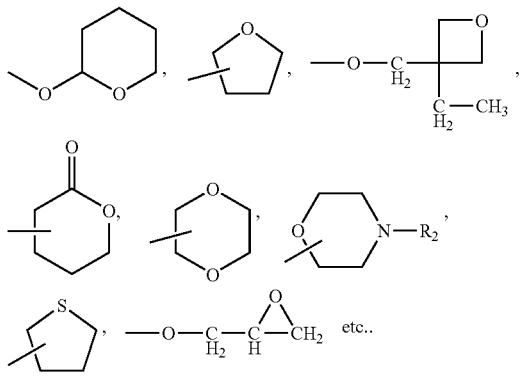

$C_7$-$C_{12}$bicycloalkyl in the context of the present application is to be understood as alkyl which at least comprises two annelated rings. For example

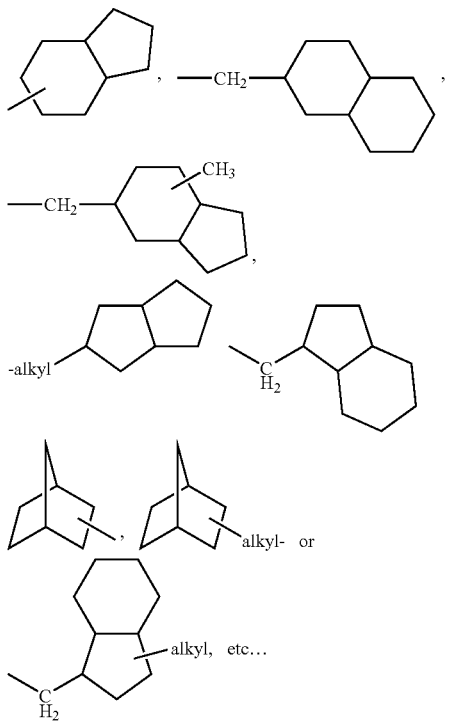

$C_5$-$C_{12}$bicycloalkyl interupted by one or more E with E defined as O, S, COO, OCO, CO, $NR_5$, $NCOR_5$, $NR_5CO$, $CONR_5$, OCOO, $OCONR_5$, $NR_5COO$, $SO_2$, SO, $CR_5$=$CR_6$ or

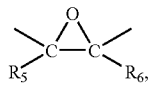

is for example

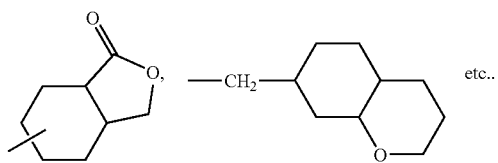

$C_{10}$-$C_{20}$tricycloalkyl in the context of the present application is to be understood as alkyl which at least comprises three annelated rings. For example

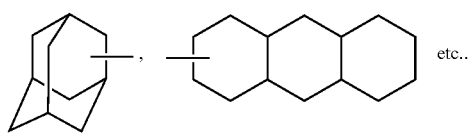

$C_7$-$C_{15}$tricycloalkyl interupted by one or more E with E defined as O, S, COO, OCO, CO, $NR_5$, $NCOR_5$, $NR_5CO$, $CONR_5$, OCOO, $OCONR_5$, $NR_5COO$, $SO_2$, SO, $CR_5$=$CR_6$ or

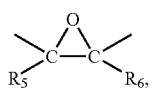

is for example

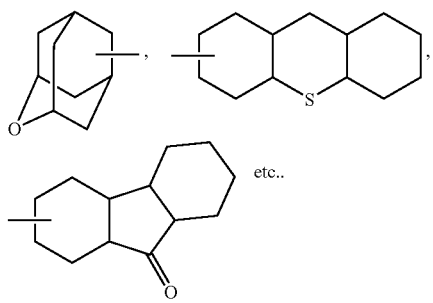

$C_5$-$C_{12}$cycloalkenyl, has one or more double bonds and is for example $C_4$-$C_6$cycloalkenyl or $C_6$-$C_8$cycloalkenyl. Examples are cyclopentenyl, cyclohexenyl or cyclooctenyl, especially cyclopentenyl and cyclohexenyl, preferably cyclohexenyl. $C_5$-$C_{12}$cycloalkenyl in the context of the present application is to be understood as alkenyl which at least comprises one ring. For example methyl-cyclopentenyl, dimethylcyclohexenyl etc. are also meant.

$C_7$-$C_{12}$bicycloalkenyl in the context of the present application is to be understood as alkenyl which at least comprises two annelated rings. For example

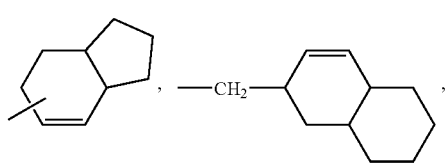

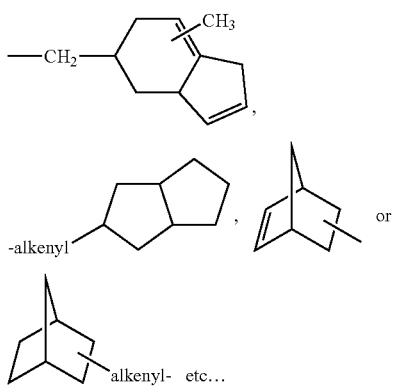

$C_6$-$C_{18}$aryl is for example phenyl, 1-naphthyl, 2-naphthyl, anthryl or phenanthryl, in particular phenyl.

Substituted $C_6$-$C_{14}$aryl is for example substituted one to four times, e.g. once, twice or three times, especially once or twice. Substituents on the phenyl ring are in position 2-, 3- or 4-, or in position 2,4-, 2,6-, 2,3-, 3,4-, 3,5-, 2,4,6- especially in position 2- or 4- of the phenyl ring.

Substituted naphthyl, anthryl or phenanthryl is for example substituted one to four times, e.g. once, twice or three times, preferably once.

Glycidyl is

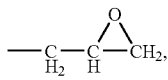

O-glycidyl denotes

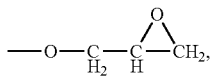

O-vinyl is

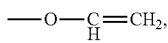

O-allyl means

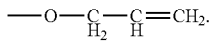

$C_8$-$C_{18}$cycloalkylenearyl denotes an aryl as defined above with an annelated cycloalkyl, for example

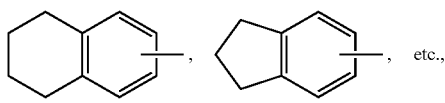

interrupted $C_7$-$C_{18}$cycloalkylenearyl is for example

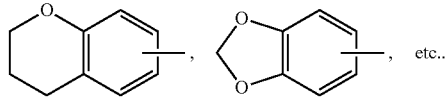

Halogen is fluorine, chlorine, bromine or iodine, especially chlorine or fluorine, preferably fluorine.

Phenylene is

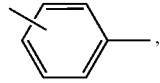

o-phenylene means, ortho-phenylene

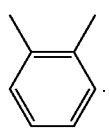

$C_3$-$C_{20}$heteroaryl, especially $C_3$-$C_{12}$heteroaryl, in the context of the present invention is meant to comprise either one ring or a multiple ring system, e.g. a fused ring-system. $C_3$-$C_{20}$heteroaryl as heteroatom comprises one or more, e.g. 1-3 or 1 or, especially 1 heteroatom(s), in particular selected from the group consisting of O, S and N.

In the context of the present invention, any heteroaryl is not meant to include an ionic heteroatom, as for example N⁺ or S⁺.

Examples are thienyl, benzo[b]thienyl, naphtho[2,3-b] thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 7-phenanthryl, anthraquinone-2-yl (=9, 10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl or 10-methyl-2-phenoxazinyl.

Preferred are heterocycles not comprising a N-atom, that is in particular heterocycles comprising O and/or S as heteroatoms, especially S; For example, thienyl, furyl, benzo[b]thienyl, naphtho[2,3-b]thienyl, thianthrenyl, benzofuryl, dibenzofuryl, chromenyl, xanthenyl, thioxanthyl, phenoxathiinyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl.

In particular preferred are compounds of the formula I or Ia, respectively, wherein R and R' and R'' as $C_3$-$C_{20}$heteroaryl are thienyl or furyl, both of which are unsubstituted or are substituted by at least one $C_1$-$C_4$alkyl and/or COT.

$C_7$-$C_{18}$cycloalkylenheteroaryl denotes a heteroaryl as described above with an annelated cycloalkyl (up to the corresponding number of C-atoms), for example

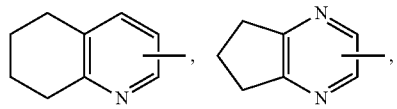

etc., interrupted $C_6$-$C_{18}$cycloalkyleneheteroaryl is for example

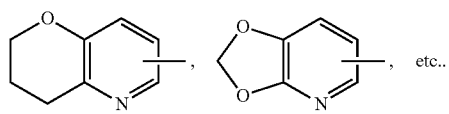

$C_3$-$C_{12}$cycloalkylene is for example cyclopentylene, cyclohexylene, cyclooctylene, cyclododecylene, especially cyclopentylene and cyclohexylene, preferably cyclohexylene. $C_3$-$C_{12}$Cycloalkylene in the context of the present application is to be understood as alkylene which at least comprises one ring. For example methyl-cyclopentylene, cyclopentylene, cyclohexylene, methyl- or dimethylcyclohexylene, cyclooctylene, especially cyclopentylene and cyclohexylene, preferably cyclohexylene. Further examples are structures like

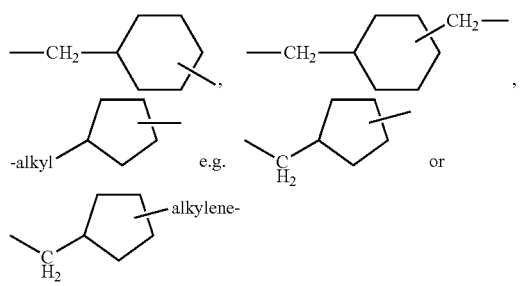

$C_7$-$C_{12}$bicycloalkylene in the context of the present application is to be understood as alkylene which at least comprises two annelated rings. For example

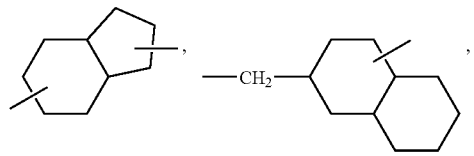

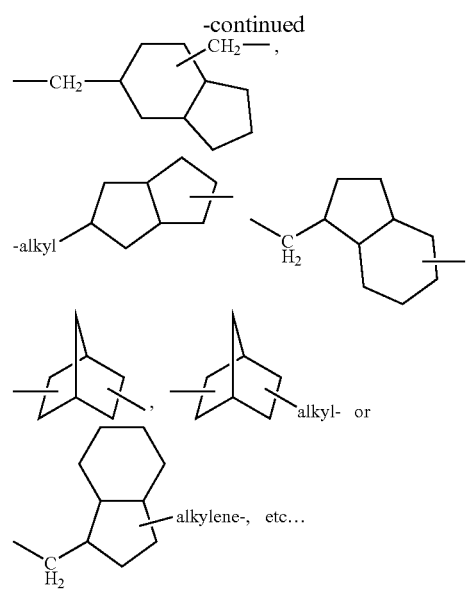

$C_5$-$C_{12}$bicycloalkylene interupted by one or more E with E defined as O, S, COO, OCO, CO, $NR_5$, $NCOR_5$, $NR_5CO$, $CONR_5$, OCOO, $OCONR_5$, $NR_5COO$, $SO_2$, SO, $CR_5$=$CR_6$ or

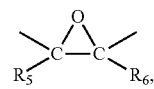

is for example

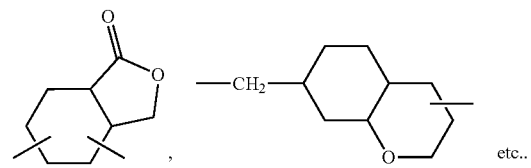

$C_{10}$-$C_{20}$tricycloalkylene in the context of the present application is to be understood as alkylene which at least comprises three annelated rings. For example

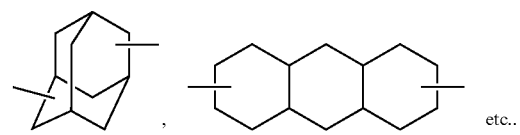

$C_7$-$C_{15}$tricycloalkylene interupted by one or more E with E defined as O, S, COO, OCO, CO, $NR_5$, $NCOR_5$, $NR_5CO$, $CONR_5$, OCOO, $OCONR_5$, $NR_5COO$, $SO_2$, SO, $CR_5$=$CR_6$ or

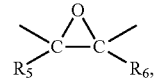

is for example

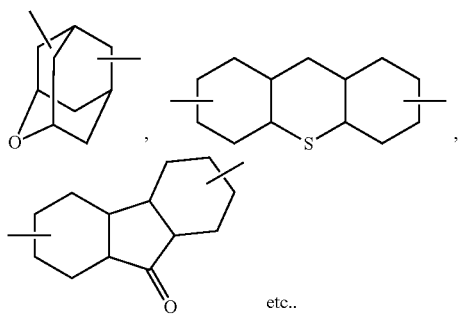, etc..

$C_5$-$C_{12}$cycloalkenylene, has one or more double bonds and is for example $C_4$-$C_6$-cycloalkenylene or $C_6$-$C_8$-cycloalkenylene. Examples are cyclopentenylene, cyclohexenylene or cyclooctenylene, especially cyclopentenylene and cyclohexenylene, preferably cyclohexenylene. $C_6$-$C_{12}$cycloalkenylene in the context of the present application is to be understood as alkenylene which at least comprises one ring. For example methylcyclopentenylene, dimethylcyclohexenylene etc. are also meant.

$C_7$-$C_{12}$bicycloalkenylene in the context of the present application is to be understood as alkenylene which at least comprises two annelated rings. For example

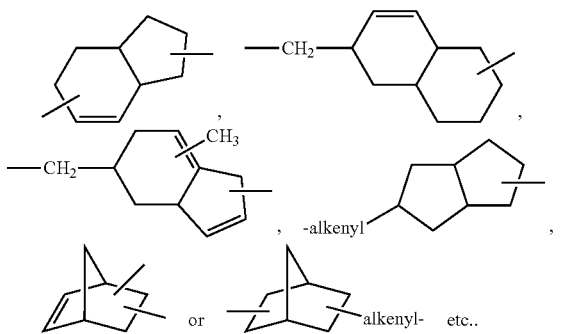

$C_6$-$C_{14}$arylene is for example phenylene, 1-naphthylene, 2-naphthylene, anthreneylene or phenanthrylene, in particular phenylene.

$C_8$-$C_{18}$cycloalkylenearylene denotes an arylene as defined above with an annelated cycloalkyl, for example

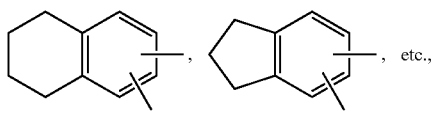, etc., interrupted $C_7$-$C_{18}$cycloalkylenearylene is for example

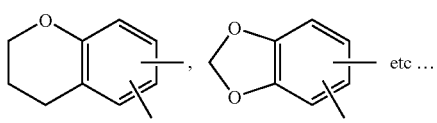 etc ...

$C_3$-$C_{20}$heteroarylene, especially $C_3$-$C_{12}$heteroarylene, in the context of the present invention is meant to comprise either one ring or a multiple ring system, e.g. a fused ring-system, as described above for the corresponding $C_3$-$C_{20}$heteroaryl, wherein the $C_3$-$C_{20}$heteroaryl comprises an additional bond. Examples are thienylene, benzo[b]thienylene etc.

$C_7$-$C_{18}$cycloalkylenheteroarylene denotes a heteroarylene as described above with an annelated cycloalkyl (up to the corresponding number of C-atoms), for example

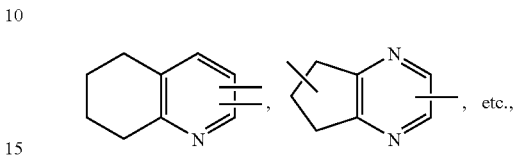, etc., interrupted $C_6$-$C_{18}$cycloalkyleneheteroarylene is for example

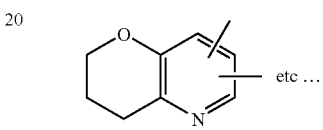 etc ...

Examples for Y as an organic or inorganic anion are halogenide, $ClO_4$, CN, hydrogenosulfate, trifluoroacetate; or for example non-nucleophilic anions, selected from the group $(BZ_4)^-$, $(SbZ_6)^-$, $(AsZ_6)^-$, $(PZ_6)^-$, $(B(C_6Z_nH_m)_4)^-$, with Z denoting a halogen, in particular F or Cl, preferably F and n and m independently of each other being an integer from 0 to 5, provided that the sum of n+m is 5, e.g. $(B(C_6Z_5)_4)^-$; $C_1$-$C_{20}$alkylsulphonate, $C_1$-$C_{20}$haloalkylsulphonate, $C_1$-$C_{20}$perfluoroalkylsulphonate, unsubstituted $C_6$-$C_{10}$arylsulphonate, camphorsulphonate, $C_1$-$C_{20}$-perfluoroalkylsulphonylmethide, $C_1$-$C_{20}$-perfluoroalkylsulphonylimide, and $C_6$-$C_{10}$arylsulphonate which is unsubstituted or substituted by halogen, $NO_2$, $SO_3M$, $C_1$-$C_{12}$alkyl, $C_1$-$C_{12}$haloalkyl, $C_1$-$C_{12}$alkoxy, phenylsulphonyloxy, $C_1$-$C_4$alkylphenylsulphonyloxy or by $COOR_{100}$; wherein $R_{100}$ is $C_1$-$C_{20}$alkyl, phenyl, benzyl or phenyl mono- or polysubstituted by $C_1$-$C_{12}$alkyl, $C_1$-$C_{12}$alkoxy or by halogen; and M is as defined above; or Y is a carborane as for example disclosed by C. A. Reed in Accounts of Chemical Research (1998), 31(3), 133-139 or U.S. Pat. No. 5,278,119.

$C_1$-$C_{20}$Alkylsulphonate is $R_xSO_3^-$ wherein $R_x$ is linear or branched $C_1$-$C_{20}$alkyl as described above. Examples thereof include methylsulphonate, ethylsulphonate, propylsulphonate, pentylsulphonate and hexylsulphonate.

$C_2$-$C_{20}$Haloalkylsulphonate is $R_xSO_3^-$ wherein $R_x$ is halo-substituted $C_2$-$C_{20}$alkyl, $C_2$-$C_{10}$-, $C_2$-$C_8$- or $C_4$-$C_8$-alkyl. Examples thereof include $C_2F_5SO_3^-$, $C_4F_9SO_3^-$ and $C_8F_{17}SO_3^-$.

$C_6$-$C_{10}$Arylsulphonate is $R_xSO_3^-$ wherein $R_x$ is $C_6$-$C_{10}$aryl, e.g. phenyl or naphthyl.

Alkyl-substituted arylsulphonates are, for example, toluenesulphonate, 2,4,6-trimethylbenzene-sulphonate, 2,4,6-tris(isopropyl)benzenesulphonate, 4-tert-butylbenzenesulphonate and 4-dodecylbenzenesulphonate.

Halo-substituted arylsulphonates are, for example, 4-chlorobenzenesulphonate, 4-fluorobenzenesulphonate, 2,4,6-trifluorobenzenesulphonate and pentafluorobenzenesulphonate.

Camphorsulphonate is

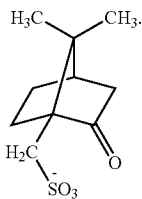

$C_1$-$C_{20}$-Perfluoroalkylsulphonylmethide is

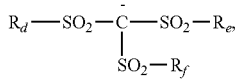

$C_1$-$C_{20}$-perfluoroalkylsulphonylimide is $R_d$—$SO_2$—$\overline{N}$—$SO_2$—$R_e$, wherein $R_d$, $R_e$ and $R_f$ independently of one another are $C_1$-$C_{20}$perfluoroalkyl which is unsubstituted or is substituted by $N(R_g)(R_h)$, or $R_d$, $R_e$ and $R_f$ are phenyl unsubstituted or preferably substituted by $CF_3$; or $R_d$ and $R_e$ together are $C_1$-$C_6$-perfluoroalkylene, which optionally is interrupted by —O—; $R_g$ and $R_h$ independently of one another are $C_1$-$C_{12}$alkyl or $R_g$ and $R_h$ together are $C_1$-$C_6$perfluoroalkylene, which optionally is interrupted by O or $N(C_1$-$C_{12}$-Alkyl).

Perfluoroalkyl is alkyl which is fully substituted by fluoro, i.e. the hydrogen atoms of the alkyl radical are replaced by fluoro. The same applies for the perfluoroalkylene.

Examples of such anions are $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(C_4F_9SO_2)_3C^-$, $(CF_3SO_2)_2(C_4F_9SO_2)C^-$, $(CF_3SO_2)(C_4F_9SO_2)N^-$, $[(3,5$-bis$(CF_3)$—$(C_6H_3)SO_2]_2N^-$,

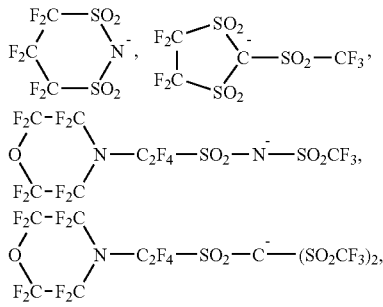

$C_6F_5SO_2C^-(SO_2CF_3)_2$, $C_6F_5SO_2N^-SO_2CF_3$. Such anions are known the person skilled in the art. The anions as well as their preparation are described e.g. in U.S. Pat. No. 5,554,664.

Other anions, that are suitable as Y in the context of the present invention are for example those as described in US 2005/0100819, page 12, [0122] to page 20, [0146], which disclosure hereby is incorporated by reference.

Y as organic or inorganic anion, for example is halogen or a non-nucleophilic anion, selected from the group $C_1$-$C_4$alkylsulphate, or perfluoroalkyl sulfonyl methides of the formula

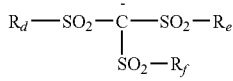

(wherein $R_d$, $R_e$ and $R_f$ independently of one another are $C_1$-$C_8$perfluoroalkyl, which optionally may form rings), e.g.

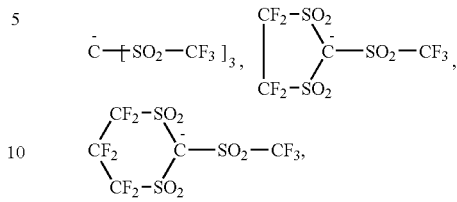

$C_fF_{2f+1}SO_3^-$, $(BZ_4)^-$, $(SbZ_6)^-$, $(AsZ_6)^-$, $(PZ_6)^-$ and $(B(C_6Z_5)_4)^-$; wherein Z is a halogen; and f is an integer from 1 to 8.

Examples of suitable methide anions are given in U.S. Pat. No. 5,554,664, JP2005-309408-A and JP2004-085657-A. The disclosures with respect to the definitions of the anions in said documents hereby are incorporated by reference.

Y in particular is halogen or a non-nucleophilic anion, selected from the group $C_1$-$C_2$alkylsulphate,

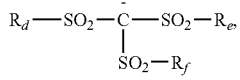

$C_fF_{2f+1}SO_3^-$, $(BZ_4)^-$, $(SbZ_6)^-$, $(AsZ_6)^-$, $(PZ_6)^-$ and $(B(C_6Z_5)_4)^-$; wherein Z is a halogen, in particular fluoro; and f is an integer from 1 to 8.

For example Y is a halogen or a non-nucleophilic anion, selected from the group $C_1$-$C_{20}$-perfluoroalkylsulphonylmethide, $C_fF_{2f+1}SO_3^-$, $(BZ_4)^-$, $(SbZ_6)^-$, $(AsZ_6)^-$, $(PZ_6)^-$ and $(B(C_6Z_5)_4)^-$; wherein f is an integer from 1 to 8.

Y in particular is halogen or a non-nucleophilic anion, selected from the group $C_fF_{2f+1}SO_3^-$, $(BF_4)^-$, $(SbF_6)^-$, $(AsF_6)^-$, $(PF_6)^-$ and $(B(C_6F_5)_4)^-$; wherein f is an integer from 1 to 8.

M as an organic or inorganic cation, for example is Li, Na, K, Cs, $N(R_m)_4$, $N(R_m)_3R_n$, $N(R_m)_2R_nR_o$, $P(R_m)_4$, $P(R_m)_3R_n$, $P(R_m)_2R_nR_o$, $S(R_m)_3$, $S(R_m)_2R_n$ or $SR_mR_nR_o$.

M preferably is Li, Na, K, $N(R_m)_4$, $N(R_m)_3R_n$, $N(R_m)_2R_nR_o$, $S(R_m)_3$, $S(R_m)_2R_n$, $SR_mR_nR_o$; in particular Na, K, $N(R_m)_4$, $N(R_m)_3R_n$, $S(R_m)_3$ or $S(R_m)_2R_n$.

$R_m$, $R_n$ and $R_o$ independently of one another are $C_1$-$C_{20}$alkyl, phenyl or phenyl which is substituted by one or more $C_1$-$C_4$alkyl.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The preferences referring to the compounds of the formula I (Ia) as given hereinbefore and in the context of the whole text, are intended not to refer to the compounds as such only, but to all categories of the claims. That is to the compositions comprising the compounds of the formula I, as well as the use or process claims in which said compounds are employed.

Another embodiment of the invention are compounds of the formula I as defined above, wherein $L_1$, $L'_1$, $L''_1$, $L_2$, $L'_2$, $L''_2$, $L_3$, $L'_3$, $L''_3$, $L_4$, $L'_4$ and $L''_4$ independently of one another are hydrogen, $R_1$, $OR_1$ or halogen; and X is O or S.

Preferred are compounds of the formula I as defined above, wherein

X is O or S;

$L_1$ and $L_2$, if X is O then $L_1$, $L_2$ independently of each other are $R_1$, $OR_1$ or halogen; if X is S, then $L_1$, $L_2$ are independently of each other hydrogen, $R_1$, $OR_1$ or halogen; and $L_3$ and $L_4$ are hydrogen.

Especially preferred are compounds of the formula I as defined above, wherein, if X is O then $L_1$ and $L_2$ independently of each other are $C_1$-$C_{12}$alkyl, $C_7$-$C_9$phenylalkyl, $C_5$-$C_{12}$cycloalkyl, $C_1$-$C_{12}$alkoxy, $C_5$-$C_{12}$cycloalkoxy, phenyl or halogen; if X is S, then $L_1$ and $L_2$ independently of each other are hydrogen, $R_1$, $OR_1$, halogen.

Preferred further are such compounds of the formula I, wherein $L_1$, $L_2$, $L_3$ and $L_4$ independently of one another are hydrogen or an organic substituent;

R is $C_3$-$C_{20}$heteroaryl or T; and, if both $L_1$ and $L_2$ are phenyl or cyclohexyl, R additionally denotes hydrogen;

X is O, S, $NR_a$ or $NCOR_a$;

Further preferred are compounds of the formula I, wherein $L_1$ and $L_2$, $L'_1$ and $L'_2$, $L''_1$ and $L''_2$ independently of one another are are as defined above, except hydrogen; and $L_3$ and $L_4$, $L'_3$ and $L'_4$, $L''_3$ and $L''_4$ independently of one another are as defined above; and all other substituents are as defined above (or below in preferred embodiments).

Other preferred compounds are of the formula I as defined above, wherein

T is $C_1$-$C_{20}$alkyl, $C_2$-$C_{20}$alkenyl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E;

X is O or S;

D is hydrogen, $R_5$, $OR_5$, halogen, O-glycidyl, O-vinyl, O-allyl, $COR_5$, $COOR_5$, $OCOR_5$, or $OCOOR_5$;

E is O, COO, OCO, CO, phenylene, $C_5$-$C_6$ cycloalkylene or $CR_2$=$CR_3$.

Particularly preferred are compounds of the formula I as defined above, wherein $L_3$ and $L_4$ are hydrogen; and $L_1$, $L_2$ independently of one another are hydrogen or $C_1$-$C_4$alkyl;

L is hydrogen, $R_1$, $OR_1$, $SR_1$, halogen, $NO_2$, CN, $COOR_1$, $OCOR_1$, $OCOOR_1$, COOT or COT;

X is O, S, $CR_aR_b$ or a single bond, provided that if X is O, R is not pyridinyl; and $R_1$ has one of the meanings given for T as defined in claim 1.

The compounds according to the present invention can for example be prepared by reacting a compound of the formula II with a thionylhalogenide, especially thionylchloride in the presence of a Friedel-Crafts catalyst:

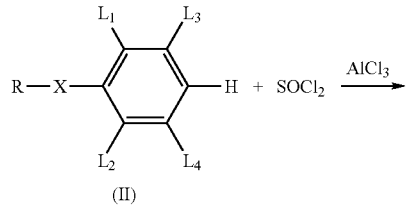

(II)

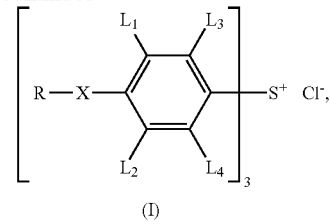

(I)

wherein R, $L_1$, $L_2$, $L_3$, $L_4$ and X are as defined above.

If compounds of the formula I, wherein L, $L'_1$, $L''_1$, $L_2$, $L'_2$, $L''_2$, $L_3$, $L'_3$, $L''_3$, $L_4$, $L'_4$ and $L_4$ are not identical, mixtures of compounds of the formula (II), (II') and/or (II'') are employed in the above reaction:

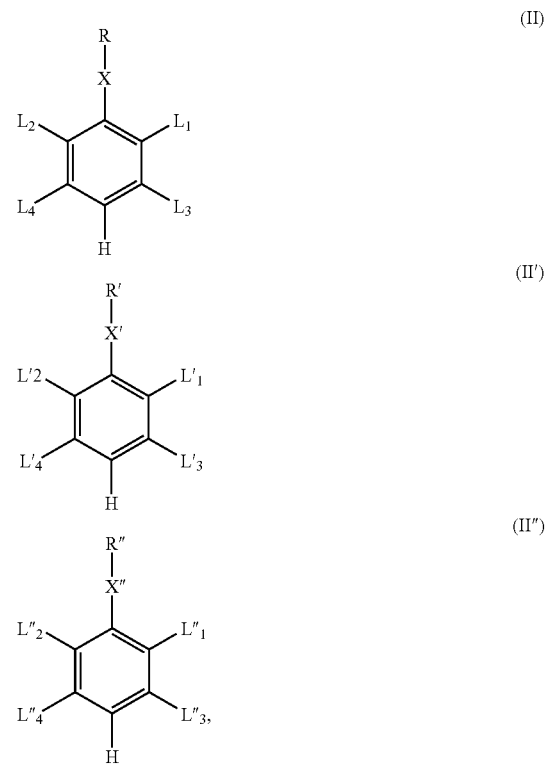

wherein R, R', R'', X, X', X'', L, $L'_1$, $L''_1$, $L_2$, $L'_2$, $L''_2$, $L_3$, $L'_3$, $L''_3$, $L_4$, $L'_4$ and $L_4$ are as defined above.

Preferably, the compounds according to the present invention can for example be prepared by reacting a compound of the formula IIa, that is a compound of the formula II, wherein R is hydrogen, with a thionylhalogenide, especially thionylchloride in the presence of a Friedel-Crafts catalyst, with a subsequent substitution reaction of the hydrogen with R as defined above however other than hydrogen:

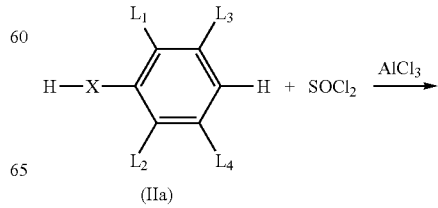

(IIa)

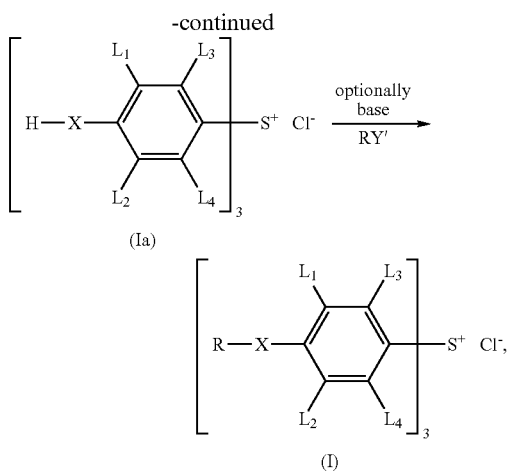

wherein R, $L_1$, $L_2$, $L_3$, $L_4$ and X are as defined above and Y' is halogenide, mesylate, tosylate, $OR_2$ or NCO.

If compounds wherein L, $L'_1$, $L''_1$, $L_2$, $L'_2$, $L''_2$, $L_3$, $L'_3$, $L''_3$, $L_4$, $L'_4$ and $L_4$ are not identical, mixtures of compounds of the formula (IIa), (IIa') and/or (IIa'') are employed in the above reaction:

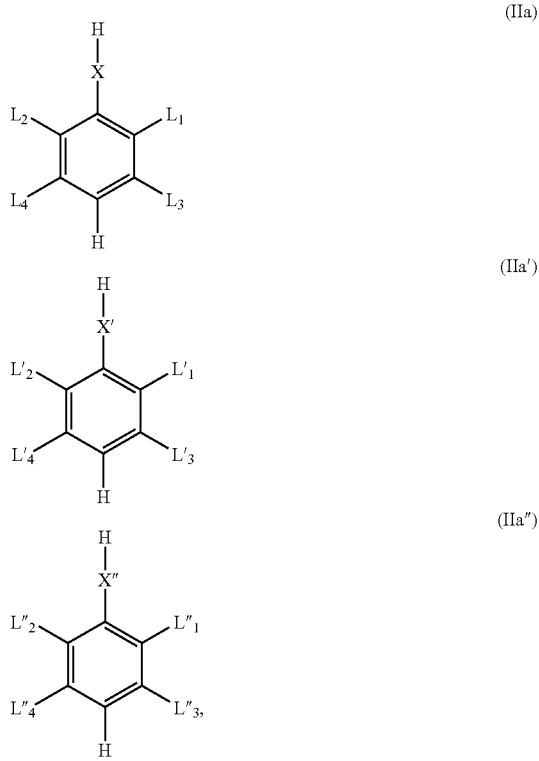

wherein X, X', X'', L, $L'_1$, $L''_1$, $L_2$, $L'_2$, $L''_2$, $L_3$, $L'_3$, $L''_3$, $L_4$, $L'_4$ and $L_4$ are as defined above.

The reaction suitably is carried out in the presence of a Friedel-Crafts catalyst. Friedel-Crafts catalysts can be Lewis acids and/or strong Bronsted acids. Such catalysts are known to the person skilled in the art and published in textbooks of chemistry. The catalysts used for Friedel-Crafts reactions for example are described in George A. Olah, *Friedel-Crafts and Related Reactions*, Vol. I, 201 and 284-90 (1963). Aluminum trihalides such as $AlBr_3$ and $AlCl_3$ are particularly suitable, especially $AlCl_3$.

Other examples are $SnCl_4$, $ZnCl_2$, $FeCl_3$, $HPF_6$; rare earth metal trifluormethanesulfonates (published in *Bulletin of the Chemical Society of Japan*, 2000, 73(10), 2325); copper trifluormethanesulfonates (known from *Tetrahedron*, 2001, 57, 241); uranyl salts (disclosed in *Journal of Molecular Catalysis A: Chemical*, 2000, 164(1-2), 195). The use of HF is described in *Journal of Organic Chemistry*, 1991, 56(20), 5955, while in *Journal of Organic Chemistry*, 1996, 61(26), 9546 alumina/trifluoroacetic anhydride is employed under microwave conditions. $ZnCl_2$ as catalyst is known from *Indian Journal of Heterocyclic Chemistry*, 2002, 11, 229.

Zeolite catalysts in Friedel Crafts reactions are for example disclosed *J. Molecular Catalysis: Chemical* 1998, 134, 121, *Applied Catalysis A: General*, 2000, 201, 159, while the use of clays or exchanged clays is known from U.S. Pat. No. 4,304,941.

The application of heteropoly acids or heteropoly acid-containing solid supports is for example described in *Journal of Molecular Catalysis A: Chemical* 2004, 209(1-2), 189.

Mixtures of Friedel-Crafts catalysts can be used and mixtures of Friedel-Crafts catalysts with salts like MY or more specifically $MPF_6$ or more interestingly with $NaPF_6$ or $KPF_6$ can be used.

The preparation process conveniently is carried out in a solvent. However it is also possible, for example, to use the aromatic hydrocarbon of formula II or IIa itself, when liquid, as solvent, in which case it is used in excess. It will be readily understood that the process can also be carried out in inert solvents. Suitable solvents are, for example, the solvents described in George A. Olah, Friedel-Crafts and Related Reactions, Vol. I, 298-302 (1963). The choice of the respective solvent depends on the solubility of the educts and catalysts. Typical examples of solvents which may be used in the process are halogenated hydrocarbons such as chlorobenzene, dichlorobenzene, carbon tetrachloride, dichloromethane, tetrachloroethylene, bromobenzene, aromatic hydrocarbon derivatives such as nitrobenzene, dinitrobenzene, benzene and toluene, saturated aliphatic hydrocarbons such as pentane, hexane, heptane and the mixtures of isomers thereof, petroleum ether or cyclohexane, or further solvents, typically carbon disulfide, nitroalkanes such as nitromethane, diethyl ether, dimethyl sulfoxide or tetramethylene sulfone.

Dichloromethane, chlorobenzene and dichlorobenzene are preferred solvents.

The process is generally carried out by mixing the educt compound of formula II or IIa with the thionylchloride and reacting said educts in a suitable vessel, which is optionally provided with a heating means. The reaction optionally is carried out under inert conditions, i.e. the vessel should be equipped with appropriate means to create said atmosphere by for example working in an atmosphere of nitrogen. Other inert gases, as for example Ar or He, could also be employed. The person skilled in the art is familiar with these facts.

The reaction of the compound of the formula II [(II'), (II'')] or IIa [(IIa'), (IIa'')] with the thionylchloride can be carried out in different manner. Representative, but not exclusive examples are given below.

a) the compound of formula II [(II'), (II'')] or IIa [(IIa'), (IIa'')] is placed, together with the catalyst and the thionylchloride, in the reaction vessel and is immediately cooled or heated to the final reaction temperature, or b) the compound of formula II [(II'), (II'')] or IIa [(IIa'), (IIa'')], together with the catalyst and the thionylchloride, is placed in the reaction vessel and cooled or heated slowly during the reaction to the final temperature, or c) the thionylchloride is added during the reaction, to the compound of formula II [(II'), (II'')] or IIa [(IIa'), (IIa'')] and the catalyst which have been previously cooled or heated to the reaction temperature, d) the catalyst is suspended in a minimum amount of either one or both of the starting materials and then the reactants are added subsequently in any order or are added together.

The reaction vessel also may for example consist of a column that is filled with the catalyst and the thionylchloride and the compound of formula II II [(II'), (II")] or IIa [(IIa'), (IIa")] are pumped (e.g. continuouesly) over the catalyst through the column.

A further possibility is to bring the reactants together via a reactive distillation, which is a process in which a catalytic chemical reaction and distillation occur simultaneously in a single apparatus.

The mol ratio of the compound of formula II [(II'), (II")] or IIa [(IIa'), (IIa")] to the thionylhalogenide in the above reaction is for example from 10:1 to 1:1; 10:1 to 1:2; or is 10:1, 5:1, 4:1, 3.5 :1, 3:2, 3:1, 1:1 or 1:2, preferably 3:1.

The reaction temperatures in principle depent on the boiling point of the educts and solvents that are employed in the reaction. Said temperature is conveniently in the range from −20° C. to about 200° C., for example from −20° C. to 140° C. or from −20° C. to 100° C., in particular from −20° C. to 80° C., preferably from −10° C. to 80° C., most preferably from 0° C. to 60° C.

The substitution of hydrogen with R=other than hydrogen can for example be done in a solvent as e.g. formamide, acetone, methylethylketone, dimethylformamide, water, optionally in the presence of a base as e.g. tributylamine, potassium carbonate, sodium carbonate, sodium hydroxide, triethylamine, soium acetate, at reaction temperatures between 0° C. and 100° C. The person skilled in the art knows how to alkylate and acylate functional groups as OH, SH and $NR_aH$.

To prepare compounds of the formula I, wherein Y is other than e.g. Cl, the chloride compound is reacted to the compound with the wanted anion by a conventional ion exchange reaction, known to the person skilled in the art. The anion Y may be already present during the Friedel-Crafts reaction.

It is of course also possible to synthesize the compounds of formula I via a stepwise synthesis through a diaryl-sulfoxide intermediate (synthesis of diarylsulphoxides from arenes and thionylchloride: Oae and Zalut, *J. Am. Chem. Soc.* 82, 5359 (1960), synthesis of diarylsulphoxides from diarylsulfides via oxidation: Drabowicz and Mikolajczyk, *Org. Prep. Proced. Int.* 14, 45-89 (1982)), which is then further reacted under the following conditions with a third compound of formula (II') to get a compound of formula (I). Again, the anion can then be exchanged optionally to an anion Y:

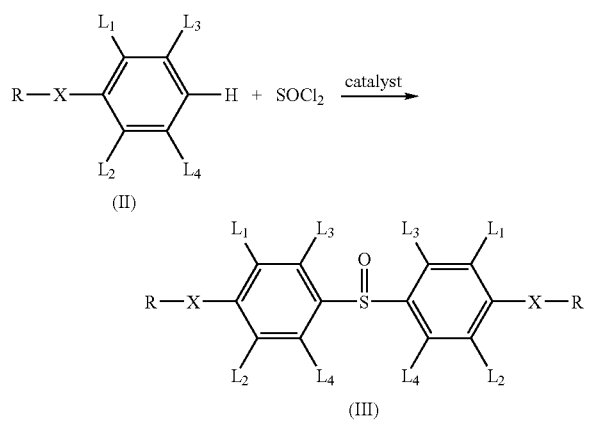

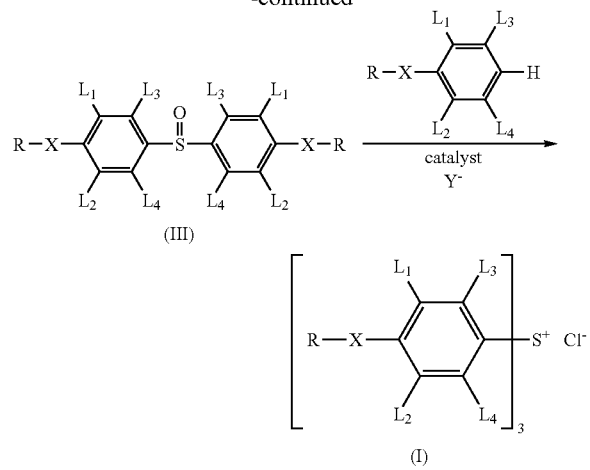

In the case where R is hydrogen, the resulting product (Ia) is for example subsequently substituted by RY' as described above.

The introduction of the third compound of formula (II) in the reaction scheme depicted above can be done in a strongly acidic medium, followed my metathesis with a salt of the desired anion. Several strong acids are available as solvents, for example, sulfuric acid, polyphosphoric acid, methanesulfonic acid, or gaseous hydrogen chloride (U.S. Pat. No. 3,488,378). Mixtures of methanesulfonic acid and phosphorus pentoxide (J. Org. Chem 1990, 55, 4222), or acetic anhydride and sulphuric acid, or methanesulfonic anhydride are also known. Typical conditions for these methods are temperatures between −50 and +100° C. Higher temperatures are usually not useful, because of secondary reactions, such as, for example, sulfonation of one aromatic ring. Lewis acids, such as aluminum chloride in terachloroethylene (WO 03/008404) can also be used. Usually, the sulfonium salt obtained by these methods has as counteranion the anion derived from one of the acids, for instance, a hydrogenosulfate, methanesulfonate, or trifluoromethanesulfonate.

Conditions without metathesis, such as arylation in acetic acid/acetic anhydride/sulfuric acid in the presence of potassium hexafluorophosphate or aqueous 75% $HPF_6$ are described for example in US 2004/0030158-A.

The starting compounds of formula II [(II'), (II")] or IIa [(IIa'), (IIa")] are for example commercially available, known to the person skilled in the art, or can be synthesized easily by the person skilled in the art.

Accordingly, subject of the invention also is a process for the preparation of a compound of the formula I, by reacting a compound of the formula II

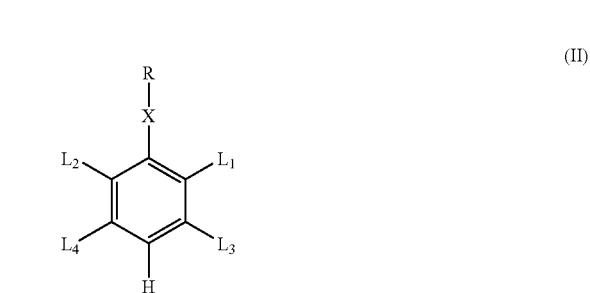

or mixtures of compounds of the formula II, II' and/or II"

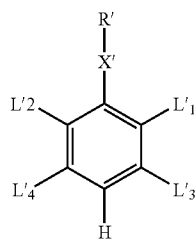
(II')

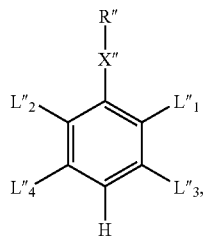
(II")

wherein

R, R', R", X, X', X", $L_1$, $L'_1$, $L"_1$, $L_2$, $L'_2$, $L"_2$, $L_3$, $L'_3$, $L"_3$, $L_4$, $L'_4$ and $L"_4$ are as defined above, with thionylchloride in the presence of a Friedel-Crafts catalyst, optionally followed by an exchange of the anion Y.

The compounds of the formula I are used as photolatent acids, i.e compounds that upon irradiation release an acid.

Accordingly, an object of the invention is a radiation-sensitive composition comprising (a1) a cationically or acid-catalytically polymerisable or crosslinkable compound or (a2) a compound that increases its solubility in a developer under the action of acid; and/or (ax) a radically polymerisable or crosslinkable compound; and (b) at least one compound of the formula I according to claim 1; as well as a radiation-sensitive composition, additionally to components (a1) or (a2) and/or (ax) and (b), comprising additives (c) and/or sensitiser compounds (d) and optionally further photoinitiators (e).

Further subject of the invention is the use of a compound of formula I as described above as photolatent acid donor in the polymerisation or crosslinking of cationically or acid-catalytically polymerisable or crosslinkable compounds or to increase the solubility of compounds that increase their solubility in a developer under the action of acid.

The compositions according to the invention comprise as component (a1), for example, resins and compounds that can be cationically polymerised by alkyl- or aryl-containing cations or by protons. Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. These include also modified surface-coating resins, such as, for example, acrylic-modified polyester and alkyd resins. Examples of individual types of resins that are included under the terms acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, 4$^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff. The surface-coating preferably comprises an amino resin. Examples thereof include etherified and non-etherified melamine, urea, guanidine and biuret resins. Of special importance is acid catalysis for the curing of surface-coatings comprising etherified amino resins, such as, for example, methylated or butylated melamine resins (N-methoxymethyl- or N-butoxymethyl-melamine) or methylated/butylated glycolurils.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and β-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis(2-hydroxyethyl)aniline; the glycidyl ethers of di- and polyphenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, o-icresyl glycidyl ether, polytetrahydrofuran glycidyl ether, n-butyl glycidyl ether, 2-ethylhexylglycidylether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components (a1) that are used in the formulations according to the invention are, for example, glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967).

There is also a large number of commercially available glycidyl ether epoxides that are suitable as component (a1), such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other glycidyl ether compounds suitable as component (a1) that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (a1).

The glycidyl ethers (a1) are, for example, compounds of formula XX

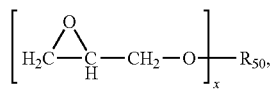
(XX)

wherein
x is a number from 1 to 6; and
$R_{50}$ is a mono- to hexavalent alkyl or aryl radical.

Preference is given, for example, to glycidyl ether compounds of formula XX, wherein
x is the number 1, 2 or 3; and
$R_{50}$ when x=1, is unsubstituted or $C_1$-$C_{12}$alkyl-substituted phenyl, naphthyl, anthracyl, biphenylyl, $C_1$-$C_{20}$alkyl, or $C_2$-$C_{20}$alkyl interrupted by one or more oxygen atoms, or
$R_{50}$ when x=2, is 1,3-phenylene, 1,4-phenylene, $C_6$-$C_{10}$cycloalkylene, unsubstituted or halosubstituted $C_1$-$C_{40}$alkylene, $C_2$-$C_{40}$alkylene interrupted by one or more oxygen atoms, or a group

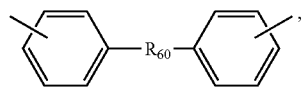

or
$R_{50}$ when x=3, is a radical

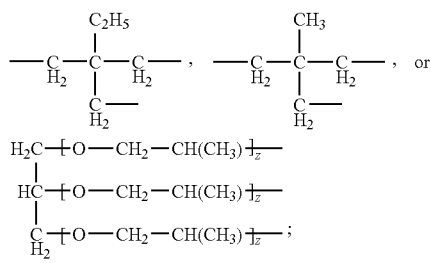

z is a number from 1 to 10; and
$R_{60}$ is $C_1$-$C_{20}$alkylene, oxygen or

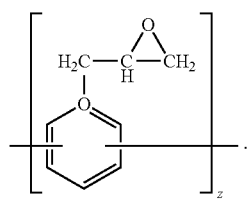

The glycidyl ethers (a1) are, for example, compounds of formula XXa

(XXa)

wherein
$R_{70}$ is unsubstituted or $C_1$-$C_{12}$alkyl-substituted phenyl; naphthyl; anthracyl; biphenylyl;
$C_1$-$C_{20}$alkyl, $C_2$-$C_{20}$alkyl interrupted by one or more oxygen atoms; or a group of formula

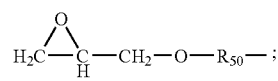

$R_{50}$ is phenylene, $C_1$-$C_{20}$alkylene, $C_2$-$C_{20}$alkylene interrupted by one or more oxygen atoms, or a group

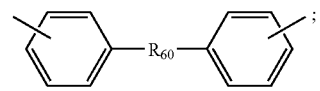

and
$R_{60}$ is $C_1$-$C_{20}$alkylene or oxygen.

Preference is given to the glycidyl ether compounds of formula XXb

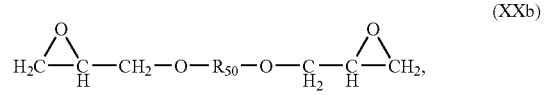
(XXb)

wherein
$R_{50}$ is phenylene, $C_1$-$C_{20}$alkylene, $C_2$-$C_{20}$alkylene interrupted by one or more oxygen atoms, or a group

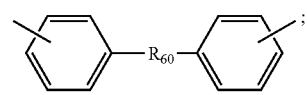

and
$R_{60}$ is $C_1$-$C_{20}$alkylene or oxygen.

Further examples for component (a1) are polyglycidyl ethers and poly(β-methylglycidyl)ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene) glycols, propane-1,2-diol and poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl) propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino)

diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulphone, 1,1,2,2-tetrakis(4-hydroxyphenyl)ethane, 2,2-bis(4-hydroxyphenyl)-propane(bis-phenol A) and 2,2-bis(3,5-dibromo-4-hydroxyphenyl)propane.

Further hydroxy compounds suitable for the preparation of polyglycidyl ethers and poly(β-methylglycidyl)ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two aminohydrogen atoms, such as aniline, n-butylamine, bis(4-aminophenyl)methane, bis(4-aminophenyl)-propane, bis-(4-methylaminophenyl)methane and bis(4-aminophenyl)ether, sulphone and sulphoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl)ether.

There also come into consideration as component (a1) epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethylhydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT® GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro-[5.5]undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, Araldit® GY 250 (A), ARALDIT®GY 282 (F), ARALDIT®GY 285 (F)), and photocurable siloxanes that contain epoxy groups.

Further suitable cationically polymerisable or crosslinkable components (a1) can be found, for example, also in U.S. Pat. Nos. 3,117,099, 4,299,938 and 4,339,567.

From the group of aliphatic epoxides there are suitable especially the monofunctional symbol α-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solventless state. Resins that are viscous to solid at room temperature can be applied hot.

Also suitable as component (a1) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexylmethyleneoxyethene)-glutaric acid methyl ester and (4-butoxyethene)-isophthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP 119425.

As component (a1), preference is given to cycloaliphatic epoxides, or epoxides based on bisphenol A.

Accordingly, the invention relates also to a radiation-sensitive composition wherein component (a1) is at least one compound selected from the group of cycloaliphatic epoxy compounds, glycidyl ethers, oxetane compounds, vinyl ethers, acid-crosslinkable melamine resins, acid-crosslinkable hydroxymethylene compounds and acid-crosslinkable alkoxymethylene compounds.

If desired, the composition according to the invention can also contain free-radically polymerisable components, such as ethylenically unsaturated monomers, oligomers or polymers. These radically polymerizable components may be added to either component (a1) or component (a2). Said radically curable components may, however, also be part of (a1) or (a2), see description of (A1), (A2) and (A3), components comprising both, radically crosslinking and cationically crosslinking groups, further below. Suitable materials contain at least one ethylenically unsaturated double bond and are capable of undergoing addition polymerisation.

Examples of suitable monomers that contain an ethylenic double bond include alkyl and hydroxyalkyl acrylates and methacrylates, such as methyl, ethyl, propyl, isopropyl, butyl, hexyl, 2-ethylhexyl and 2-hydroxyethyl (meth)acrylate, stearyl acrylate and isobornyl acrylates. Further suitable examples include acrylonitrile, acrylamide, methacrylamide, N-substituted (meth)acrylamides, vinyl esters, such as vinyl acetate, vinyl ethers, such as isobutylvinyl ether, styrene, alkyl- and halo-substituted styrene, N-vinylpyrrolidone, vinyl chloride and vinylidene chloride.

Examples of suitable monomers that contain at least two double bonds include glycerol diacrylates, glycerol triacrylates, ethylene glycol diacrylates, diethylene glycol diacrylates, diethylene glycol dimethacrylate, triethylene glycol dimethacrylates, 1,3-propanediol diacrylate, 1,3-propanediol dimethacrylate, neopentyl glycol diacrylates, hexamethylene glycol diacrylate, bisphenol-A diacrylates, 4,4'-bis(2-acryloyloxyethoxy)diphenylpropane, pentaerythritol triacrylate or tetraacrylate, pentaerythritol tetramethacrylate, trimethylolpropane triacrylate, 1,2,4-butanetriol trimethacrylate, 1,4-cyclohexanediol diacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane and trishydroxyethyl isocyanurate trimethacrylate; the bis-acrylates and bis-methacrylates of poly(ethylene glycol) having a molecular weight of from 200 to 500, diallyl phthalate, divinyl succinate, divinyl adipate and divinyl phthalate, vinyl acrylate, divinyl benzene, triallyl phosphate, triallyl isocyanurates and tris(2-acryloyl-ethyl)isocyanurate.

Examples of higher-molecular-weight (oligomeric) polyunsaturated compounds include acrylated epoxy resins, acrylated or vinyl ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, poly-urethane, polyether, polyvinyl ether and epoxy main chains can also be used. Also copolymers of vinyl ethers and monomers which are functionalised with maleic acid, as described in WO 90/01512, are also very suitable. Also suitable, however, are copolymers of monomers functionalised with vinyl ether and maleic acid. Such unsaturated oligomers can also be referred to as pre-polymers. Functionalised acrylates are also suitable. Examples of suitable monomers that are normally used to form the base polymer (the backbone) of the functionalised acrylate or methacrylate polymer are acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc . . . In addition, suitable amounts of functional monomers are copolymerised during the polymerisation in order to obtain the functional polymers. Acid-functionalised acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate and 3,4-dihydroxybutyl methacrylate. Epoxy-functionalised acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl meth-acrylate, etc. It is also possible to obtain isocyanate-functional polymers from isocyanate-functionalised monomers, such as meta-isopropenyl-α,α-dimethylbenzyl isocyanate.

Especially suitable are, for example, esters of ethylenically unsaturated mono- or poly-functional carboxylic acids and polyols or polyepoxides, and polymers having ethylenically unsaturated groups in the chain or in side groups, such as unsaturated polyesters, poly-amides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Mixtures of saturated di- or poly-carboxylic acids with unsaturated carboxylic acids may, however, also be used. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichlorohydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified by other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, penta-erythritol triacrylate, pentaerythritol tetraacrylate, dipentaerythritol diacrylate, dipenta-erythritol triacrylate, dipentaerythritol tetraacrylate, dipentaerythritol pentaacrylate, dipenta-erythritol hexaacrylate, tripentaerythritol octaacrylate, pentaerythritol dimethacrylate, penta-erythritol trimethacrylate, dipentaerythritol dimethacrylate, dipentaerythritol tetrameth-acrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Suitable unsaturated, free-radically polymerisable compounds are also the amides of the same or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetraamine and di-(β-aminoethoxy)- or di-(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated or unsaturated diisocyanates and saturated or unsaturated diols.

Polybutadiene and polyisoprene and copolymers thereof are known. Suitable comonomers include, for example, olefins, such as ethylene, propene, butene, hexene, (meth)acrylates, acrylonitrile, styrene and vinyl chloride. Polymers having (meth)acrylate groups in the side chain are also known. They may be, for example, reaction products of novolak-based epoxy resins with (meth)acrylic acid; homo- or co-polymers of vinyl alcohol or hydroxyalkyl derivatives thereof that have been esterified with (meth)acrylic acid; or homo- and co-polymers of (meth)acrylates that have been esterified with hydroxyalkyl(meth)acrylates.

It is also possible to use compounds that can be crosslinked equally both free-radically and cationically. Such compounds contain, for example, both a vinyl group and a cycloaliphatic epoxy group. Examples thereof are described in JP 2-289611-A and U.S. Pat. No. 6,048,953.

Mixtures of two or more of such free-radically polymerisable materials can also be used.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids.

The binder will be selected according to the field of use and the properties required therefor, such as developability in aqueous and organic solvent systems, adhesion to substrates and sensitivity to oxygen.

Suitable binders are, for example, polymers having a molecular weight of approximately from 2000 to 2 000 000, preferably from 5000 to 1 000 000. Examples thereof are: homo- and copolymers of acrylates and methacrylates, for example copolymers of methyl methacrylate/ethyl acrylate/methacrylic acid, poly(methacrylic acid alkyl esters), poly (acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as poly-ethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephthalate) and poly(hexamethylene glycol succinate); and polyamides.

The resins mentioned below under (C1) may also be used as the free-radically curable component (ax). Of particular interest are, for example, unsaturated acrylates having reactive functional groups. The reactive functional group may be selected, for example, from a hydroxyl, thiol, isocyanate, epoxy, anhydride, carboxyl, amino or blocked amino group. Examples of OH-group-containing unsaturated acrylates are hydroxyethyl and hydroxybutyl acrylates and also glycidyl acrylates.

A further description of the radically polymerizing component (ax) is for example given in WO 07/062963 page 29, line 25 to page 32, line 19 the disclosure of which hereby is incorporated by reference. Further the additives, described as suitable in such radically polymerizable compositions, as given in WO 07/062963 also are suitable in the context of the present invention in case a component (ax) is present.

The unsaturated compounds may also be used in admixture with non-photopolymerisable film-forming components. These may be, for example, polymers that can be dried physically or solutions thereof in organic solvents, such as nitro-cellulose or cellulose acetobutyrate.

They may alternatively be chemically or thermally curable resins, such as polyisocyanates, polyepoxides or melamine resins. Drying oils, such as linseed oil, linseed-oil-modified alkyd resins, tung oil and soybean oil, can also be present. The concomitant use of thermally curable resins is important for use in so-called hybrid systems which are photopolymerised in a first step and crosslinked by thermal aftertreatment in a second step.

Thus, the radiation-curable compositions of the present invention may also comprise:

(A1) compounds having one or more free-radically polymerisable double bonds that additionally contain at least one further functional group that is reactive in addition and/or condensation reactions (examples are given above), (A2) compounds having one or more free-radically polymerisable double bonds that additionally contain at least one further functional group that is reactive in addition and/or condensation reactions, the additional functional group being complementary to or reactive towards the additional functional group of component (A1), (A3) at least one monomeric, oligomeric and/or polymeric compound having at least one functional group that is reactive in addition and/or condensation reactions towards the functional groups of component (A1) or (A2) that are present in addition to the free-radically polymerisable double bonds.

Component (A2) in each case carries the groups complementary to or reactive towards component (A1). Different types of functional groups may also be present in a component.

Component (A3) provides a component that contains further functional groups that are reactive in addition and/or condensation reactions and that are able to react with the functional groups of (A1) or (A2) that are present in addition to the free-radically polymerisable double bonds. Component (A3) contains no free-radically polymerisable double bonds.

Examples of such combinations (A1), (A2), (A3) can be found in WO 99/55785.

Examples of suitable functional groups are hydroxyl, isocyanate, epoxy, anhydride, carboxyl and blocked amino groups. Examples have been described above.

Constituents of the thermally curable component (C) are, for example, thermally curable lacquer or coating system constituents customary in the art. Component (C) accordingly may consist of a large number of constituents.

Examples of component (C) include oligomers and/or polymers derived from $\alpha,\beta$-unsaturated acids and derivatives thereof, for example polyacrylates and polymethacrylates, polymethyl methacrylates impact-resistant-modified with butyl acrylate, polyacrylamides and polyacrylonitriles. Further examples of component (C) are urethanes, polyurethanes derived on the one hand from polyethers, polyesters and polyacrylates having free hydroxyl groups and on the other hand from aliphatic or aromatic polyisocyanates, and educts thereof. Component (C) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (C).

Component (C) is, for example, generally a film-forming binder based on a thermoplastic or thermocurable resin, especially on a thermocurable resin. Examples thereof are alkyd, acrylic, polyester, phenolic, melamine, epoxy and polyurethane resins and mixtures thereof. Examples thereof can be found, for example, in Ullmann's Encyclopedia of Industrial Chemistry, 5th Ed., Vol. A18, pp. 368-426, VCH, Weinheim 1991.

Component (C) may also be a cold-curable or hot-curable binder, in which case the addition of a curing catalyst may be advantageous. Suitable catalysts that accelerate the full cure of the binder can be found, for example, in Ullmann's Encyclopedia of Industrial Chemistry, Vol. A18, page 469, VCH Verlagsgesellschaft, Weinheim 1991.

Specific examples of binders suitable as component (C) are:

1. surface-coatings based on cold- or hot-crosslinkable alkyd, acrylate, polyester, epoxy or melamine resins or mixtures of such resins, optionally with the addition of a curing catalyst;
2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during heating; it is also possible to add melamine resins as appropriate;
4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly)ketimines and aliphatic or aromatic isocyanates, isocyanurates or polyisocyanates;
7. two-component surface-coatings based on (poly)ketimines and an unsaturated acrylate resin or a polyacetoacetate resin or a methacrylamidoglycolate methyl ester;
8. two-component surface-coatings based on carboxyl- or amino-group-containing polyacrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly)oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane(meth)acrylate having (meth)acryloyl groups and free isocyanate groups and on one or more compounds that react with iso-cyanates, for example free or esterified polyols. Such systems have been published, for example, in EP 928800.

Blocked isocyanates that can also be used as component (C) are described, for example, in Organischer Metallschutz: Entwicklung and Anwendung von Beschichtungsstoffen, pages 159-160, Vincentz Verlag, Hanover (1993). These are compounds in which the highly reactive NCO group is "blocked" by reaction with specific radicals, for example a primary alcohol, phenol, acetic acid ethyl ester, $\in$-caprolactam, phthalimide, imidazole, oxime or amine. The blocked isocyanate is stable in liquid systems and also in the presence of hydroxy groups. Upon heating, the blocking group (protecting group) is removed again and the NCO group is freed.

1-Component (1C) and 2-component (2C) systems may be used as component (C). Examples of such systems are described in Ullmann's Encyclopedia of Industrial Chemistry, Vol. A18, Paints and Coatings, pages 404-407, VCH Verlagsgesellschaft mbH, Weinheim (1991). It is possible to optimise the composition by specific adaptation, for example by varying the binder/crosslinking agent ratios. Such measures will be known to the person skilled in the art and are customary in coating technology.

In the curing process according to the invention, component (C) is preferably a mixture based on acrylate/melamine (and melamine derivatives), 2-component polyurethane, 1-component polyurethane, 2-component epoxy/carboxy or 1-component epoxy/carboxy. Mixtures of such systems are also possible, for example the addition of melamine (or derivatives thereof) to 1-component polyurethanes.

Component (C) is preferably a binder based on a polyacrylate with melamine or on a melamine derivative or a system based on a polyacrylate and/or polyester polyol with an unblocked polyisocyanate or polyisocyanurate.

Component (C) may also comprise monomeric and/or oligomeric compounds having ethylenically unsaturated bonds (prepolymers) that additionally contain at least one or more OH, $NH_2$, COOH, epoxy or NCO group(s) (=C1) that are capable of reaction with the binder and/or the crosslinking agent constituent of component (C). After application and thermal curing, the ethylenically unsaturated bonds are converted to a crosslinked, high molecular weight form by irradiation with UV light. Examples of such components (C) are described, for example, in the above-mentioned publication, Ullmann's Encyclopedia of Industrial Chemistry, 5th Ed., Vol. A18, pages 451-453, or by S. Urano, K. Aoki, N. Tsuboniva and R. Mizuguchi in Progress in Organic Coatings, 20 (1992), 471-486, or by H. Terashima and O. Isozaki in JOCCA 1992 (6), 222.

(C1) may, for example, also be an OH-group-containing unsaturated acrylate, for example hydroxyethyl or hydroxybutyl acrylate or a glycidyl acrylate. Component (C1) may be of any desired structure (for example it may contain units of polyester, polyacrylate, polyether, etc.), provided that it contains an ethylenically unsaturated double bond and additionally free OH, COOH, NH$_2$, epoxy or NCO groups.

(C1) may, for example, also be obtained by reacting an epoxy-functional oligomer with acrylic acid or methacrylic acid. A typical example of an OH-functional oligomer having vinylic double bonds is alkyd resins. At least some of the alkyd resin composition in the non-aqueous coating is oxidatively drying as a result of the incorporation of a large number of unsaturated, aliphatic compounds, at least some of which are polyunsaturated.

Formulations containing those modified alkyd resins as component (a1) may optionally contain, in addition to the photoinitiator (b), an oxidative dryer. Suitable oxidative dryers are, for example, metal siccatives. There may be mentioned as suitable siccatives, for example, the metal salts of (cyclo)aliphatic acids, such as octanoic acid and naphthenic acid, the metals to be used being, for example, cobalt, manganese, lead, zirconium, calcium, zinc and rare earth metals. Mixtures of siccatives may be used. Preference is given to metal salts of cobalt, zirconium and calcium, or mixtures thereof. The siccatives (calculated as metal) are usually used in an amount of from 0.001 to 3% by weight.

Under certain conditions it may also be advantageous, when using the modified alkyd resins as component (a1), to use one or more mono- or bis-acylphosphine oxide photoinitiators in addition to the sulphonium salt of formula (I). Suitable monoacyl- or bisacyl-phosphine oxide photoinitiators

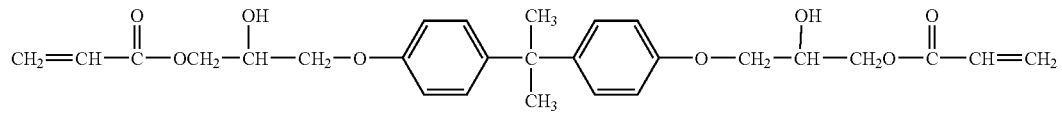

obtained by reaction of

CH$_2$═CHCOOH with

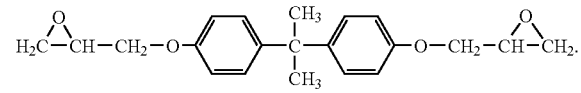

Another possible method of obtaining component (C1) is, for example, the reaction of an oligomer that contains only one epoxy group and has a free OH group at another position in the molecule.

The quantity ratio of the free-radically radiation-curable-polymerisable components to the thermally polymerisable component (C) in the UV- and thermally-crosslinkable formulations is not critical. "Dual-cure" systems are known to the person skilled in the art, who will therefore be familiar with the optimum mixing ratios of the free-radically- and thermally-crosslinkable components according to the intended use. For example, the ratio can be in the range from 5:95 to 95:5, from 20:80 to 80:20 or from 30:70 to 70:30, for example from 40:60 to 60:40.

Examples of "dual-cure" systems, that is to say systems comprising both radiation-curable and thermally curable components, can be found inter alia in U.S. Pat. No. 5,922,473, columns 6 to 10.

The formulations according to the invention can further comprise as component (a1) non-aqueous coating compositions based on an oxidatively drying alkyd resin which contains at least one, preferably two or more, functional group(s) capable of undergoing polymerisation or polycondensation reactions in the presence of an acid. Examples of such resins are vinyl-ether-functionalised alkyd resins, acetal-functionalised alkyd resins, and/or alkoxysilane-functionalised alkyd resins, as proposed, e.g., in WO 99/47617. Those modified alkyd resins may be used alone or in combination with other include, for example, monoacylphosphine oxides such as (2,4,6-trimethylbenzoyl)-diphenylphosphine oxide (DAROCUR®TPO) or (2,4,6-trimethylbenzoyl-phenyl-ethoxy-phosphine oxide, or bisacylphosphine oxide photoinitiators such as bis(2,6-di-methoxybenzoyl)-2,4,4-trimethylpentyl-phosphine oxide, bis(2,4,6-trimethylbenzoyl)-(2,4-dipentyloxyphenyl)-phosphine oxide and bis(2,4,6-trimethylbenzoyl)phenyl-phosphine oxide (IRGACURE®819). Those monoacyl- or bisacylphosphine oxides are advantageously used in an amount of from 0.5 to 5%.

When component (a1)) contains modified alkyd resins, in addition to the photoinitiator (b) it is also possible to use an oxidative dryer and suitable monoacyl- or bisacyl-phosphine oxide photoinitiators.

The alkyd resins used as component (a1) contain a large number of unsaturated, aliphatic compounds, at least some of which are polyunsaturated. The unsaturated aliphatic compounds preferably used for the preparation of those alkyd resins are unsaturated aliphatic monocarboxylic acids, especially polyunsaturated aliphatic monocarboxylic acids.

Examples of mono-unsaturated fatty acids are myristoleic acid, palmitic acid, oleic acid, gadoleic acid, erucic acid and ricinoleic acid. Preferably fatty acids containing conjugated double bonds, such as dehydrogenated castor oil fatty acid and/or tung oil fatty acid, are used. Other suitable monocarboxylic acids include tetrahydrobenzoic acid and hydrogenated or non-hydrogenated abietic acid or the isomers thereof. If desired, the monocarboxylic acid in question may be used wholly or in part in the form of a triglyceride, e.g. as vegetable oil, in the preparation of the alkyd resin. If desired, mixtures of two or more such mono-carboxylic acids or triglycerides may be used, optionally in the presence of one or more saturated, (cyclo)aliphatic or aromatic monocarboxylic acids, e.g. pivalic acid, 2-ethyl-hexanoic acid, lauric acid, palmitic acid, stearic acid, 4-tert-butyl-benzoic acid, cyclopentanecarboxylic acid, naphthenic acid, cyclohexanecarboxylic acid, 2,4-dimethylbenzoic acid, 2-methylbenzoic acid and benzoic acid.

If desired, polycarboxylic acids may also be incorporated into the alkyd resin, such as phthalic acid, isophthalic acid, terephthalic acid, 5-tert-butylisophthalic acid, trimellitic acid, pyromellitic acid, succinic acid, adipic acid, 2,2,4-trimethyladipic acid, azelaic acid, sebacic acid, dimerised fatty acids, cyclopentane-1,2-dicarboxylic acid, cyclohexane-1,2-dicarboxylic acid, 4-methylcyclohexane-1,2-dicarboxylic acid, tetrahydrophthalic acid, endomethylene-cyclohexane-1,2-dicarboxylic acid, butane-1,2,3,4-tetracarboxylic acid, endoisopropylidene-cyclohexane-1,2-dicarboxylic acid, cyclohexane-1,2,4,5-tetracarboxylic acid and butane-1,2,3,4-tetracarboxylic acid. If desired, the carboxylic acid in question may be used as an anhydride or in the form of an ester, for example an ester of an alcohol having from 1 to 4 carbon atoms.

In addition, the alkyd resin can be composed of di- or poly-valent hydroxyl compounds.

Examples of suitable divalent hydroxyl compounds are ethylene glycol, 1,3-propanediol, 1,6-hexanediol, 1,12-dodecanediol, 3-methyl-1,5-pentanediol, 2,2,4-trimethyl-1,6-hexane-diol, 2,2-dimethyl-1,3-propanediol and 2-methyl-2-cyclohexyl-1,3-propanediol. Examples of suitable triols are glycerol, trimethylolethane and trimethylolpropane. Suitable polyols having more than 3 hydroxyl groups are pentaerythritol, sorbitol and etherified products of the compounds in question, such as ditrimethylolpropane and di-, tri- and tetra-pentaerythritol. Preferably, compounds having from 3 to 12 carbon atoms, e.g. glycerol, pentaerythritol and/or dipentaerythritol, are used.

The alkyd resins can be obtained by direct esterification of the constituents, with the option that some of those components may already have been converted into ester diols or polyester diols. The unsaturated fatty acids can also be used in the form of a drying oil, such as linseed oil, tuna fish oil, dehydrogenated castor oil, coconut oil and dehydrogenated coconut oil. The final alkyd resin is then obtained by transesterification with the other acids and diols added. The transesterification is advantageously carried out at a temperature in the range of from 115 to 250° C., optionally in the presence of solvents such as toluene and/or xylene. The reaction is advantageously carried out in the presence of a catalytic amount of a transesterification catalyst. Examples of suitable transesterification catalysts include acids, such as p-toluenesulphonic acid, basic compounds, such as an amine, or compounds such as calcium oxide, zinc oxide, tetraisopropyl orthotitanate, dibutyltin oxide and tri-phenylbenzylphosphonium chloride.

The vinyl ether, acetal and/or alkoxysilane compounds used as part of component (a1) preferably contain at least two vinyl ether, acetal and/or alkoxysilane groups and have a molecular weight of 150 or more. Those vinyl ether, acetal and/or alkoxysilane compounds can be obtained, for example, by the reaction of a commercially available vinyl ether, acetal and/or alkoxysilane compound containing a vinyl ether, acetal and/or alkoxysilane group and in addition a maximum of one functional amino, epoxy, thiol, isocyanate, acrylic, hydride or hydroxyl group, with a compound having at least two groups capable of reacting with an amino, epoxy, thiol, isocyanate, acrylic, hydride or hydroxyl group. As examples thereof there may be mentioned compounds having at least two epoxy, isocyanate, hydroxyl and/or ester groups or compounds having at least two ethylenically or ethynylenically unsaturated groups.

As component (a1), preference is given to a composition in which the vinyl ether, acetal and/or alkoxysilane compounds are covalently bonded to the alkyd resin by addition via a reactive group such as an amino, hydroxyl, thiol, hydride, epoxy and/or isocyanate group. For that purpose, the compounds must have at least one group capable of forming an adduct with the reactive groups present in the alkyd resin.

To incorporate vinyl ether groups into the alkyd resin, use is made of a vinyloxyalkyl compound, the alkyl group of which is substituted by a reactive group, such as a hydroxyl, amino, epoxy or isocyanate group, that is capable of forming an adduct with one or more of the reactive groups present in the alkyd resin.

As component (a1), preference is given to compositions in which the ratio of the number of oxidatively drying groups present in the alkyd resin to the number of groups that are reactive in the presence of an acid is in the range of from 1/10 to 15/1, especially from 1/3 to 5/1. Instead of a single modified alkyd resin, it is also possible to use a plurality of alkyd resins, with one alkyd resin being highly modified and the others being less modified or not modified at all.

Examples of vinyl ether compounds capable of being covalently bonded to the alkyd resin are ethylene glycol monovinyl ether, butanediol monovinyl ether, hexanediol monovinyl ether, triethylene glycol monovinyl ether, cyclohexanedimethanol monovinyl ether, 2-ethylhexanediol monovinyl ether, polytetrahydrofuran monovinyl ether, tetraethylene glycol monovinyl ether, trimethylolpropane divinyl ether and aminopropyl vinyl ether.

Adducts can be formed, for example, by reacting the vinyl ether compounds containing a hydroxyl group or amino group with an excess of a diisocyanate, followed by the reaction of that free-isocyanate-group-containing adduct with the free hydroxyl groups of the alkyd resin. Preferably, a process is used in which first the free hydroxyl groups of the alkyd resin react with an excess of a polyisocyanate, and then the free isocyanate groups react with an amino-group- or hydroxyl-group-containing vinyl ether compound. Instead of a diisocyanate, it is also possible to use a diester. Transesterification of the hydroxyl groups present in the alkyd resin with an excess of the diester, followed by transesterification or transamidation of the remaining ester groups with hydroxy-functional vinyl ether compounds or amino-functional vinyl ether compounds, respectively, yields vinyl-ether-functional alkyd resins. It is also possible to incorporate (meth)acrylate groups into the alkyd resin during preparation of the alkyd resin, by carrying out the preparation in the presence of a hydroxy-functional (meth)acrylate ester, such as hydroxyethyl methacrylate (HEMA), and then reacting the thus functionalised alkyd resin by means of a Michael reaction with a vinyl-ether-group-containing compound and a primary-amino-group-containing compound, followed by reaction with e.g. an isocyanate compound, in order to obtain a non-basic nitrogen atom.

An example of such a reaction is described, for example, in WO 99/47617. Esterification of ricinine fatty acid with dipentaerythritol, followed by transesterification of the free hydroxyl groups with diethyl malonate and 4-hydroxybutyl vinyl ether in a suitable ratio, yields a vinyl-ether-functional alkyd resin suitable for use as component (a1).

For the preparation of acetal-functional alkyd resins, use is generally made of dialkyl acetal functionalised with an amino group. Examples of suitable acetal compounds include 4-aminobutyraldehyde dimethyl acetal and 4-aminobutyraldehyde diethyl acetal. The alkyd resin is modified by the addition of the aminoacetal monomer to an alkyd resin functionalised with isocyanate groups, with ester groups of a low-boiling alcohol or with (meth)acrylate groups. The resulting dialkyl-acetal-modified alkyd resin can be incorporated into the coating composition having a high solids content and low viscosity. The preparation of acetal-functional alkyd resins can also be carried out by reacting hydroxyacetal with the carboxyl groups of the alkyd resin or by reacting a diisocyanate or diester compound with the hydroxyl groups of the alkyd resin.

An example of this preparative method is described in WO 99/47617, for example the esterification of a hydroxy-functional alkyd resin with diethyl malonate, followed by transamidation of the free ester group with 4-aminobutyraldehyde dimethyl acetal in a suitable ratio. The resulting acetal-modified alkyd resin is suitable as component (a1).

For the incorporation of alkoxysilane groups into the alkyd resin, use is made of a siloxane compound having one or more reactive group(s) which are subsequently reacted with one or more of the constituents making up the alkyd resin. These are, for example, alkoxy-silanes of the formula: $(E)_a\text{-Si}(R_{10})_b(R_{20})_c$, wherein $R_{10}$ is alkoxy or oxyalkylenealkoxy or, when E is hydrogen, $R_{10}$ is halogen, $R_{20}$ is an aliphatic, cycloaliphatic or aromatic group, and E is hydrogen or an alkyl group substituted by an amino, isocyanate, mercapto or epoxy group; a is from 1 to 3, b is from 1 to 3, c is from 0 to 2, and a+b+c=4.

$R_{10}$ is preferably an alkoxy group having from 1 to 4 carbon atoms in the alkoxy group, and $R_{20}$ is preferably a group having not more than 18 carbon atoms.

Examples of suitable siloxane compounds are 3-aminopropyl-triethoxysilane, polyglycolether-modified aminosilane, 3-aminopropyl-trimethoxysilane, 3-aminopropyltris-methoxy-ethoxyethoxysilane, 3-aminopropyl-methyl-diethoxysilane, N-2-aminoethyl-3-aminopropyl-tri-methoxy-silane, N-2-aminoethyl-3-aminopropyl-methyldimethoxy-silane, N-methyl-3-amino-propyl-trimethoxysilane, 3-ureidopropyl-triethoxysilane, 3,4,5-dihydroimidazol-1-yl-propyltriethoxysilane, 3-methacryloxypropyl-trimethoxysilane, 3-glycidyloxypropyl-trimethoxysilane, 3-mercaptopropyl-trimethoxysilane and 3-mercaptopropyl-methyl-dimethoxysilane, triethoxysilane, diethoxymethylsilane, dimethoxymethylsilane, tri-methoxysilane, trichlorosilane, triiodosilane, tribromosilane, dichloromethylsilane and dibromomethylsilane.

The alkyd resin can be modified, for example, by the insertion of an amino-group-modified alkoxysilane into an alkyd resin modified with a polyisocyanate or a polyester of a low-boiling alcohol. Hydride-functional alkoxysilanes can be bonded directly to the alkyd, i.e. without modification with a binding molecule such as a diisocyanate or diester, by adding a compound containing a silylhydride group to an ethylenically unsaturated group in the alkyd resin. That addition is catalysed by a transition metal. In that process, use is preferably made of a halogenated silylhydride and, in order to terminate the addition reaction, conversion into an alkoxysilane compound with a low-boiling alcohol. The addition reaction is advantageously carried out in the absence of sterically hindering groups and proceeds in optimum manner when the ethylenically unsaturated groups are terminal groups, as is the case, for example, with esters of 10-undecenecarboxylic acid.

Examples of the preparation of alkoxysiloxane-modified alkyd resins are described in WO 99/47617. Esterification of a hydroxy-functional alkyd resin with diethyl malonate, followed by transamidation of the free ester group with 3-aminopropyltriethoxysilane in a suitable ratio yields an alkoxysilane-modified alkyd resin. Hydroxy-modified alkyd resin can also be reacted with an excess of isophorone diisocyanate, followed by reaction of the free isocyanate groups with 3-aminopropyltriethoxysilane. Both alkoxysiloxane-modified alkyd resins obtained by the processes described are suitable for use in component (a1).

When free-radically polymerisable components are added to the formulation according to the invention, or in case that a component (ax) is present, it may be advantageous to add also a suitable free-radical photoinitiator or a mixture of such photoinitiators, e.g. camphor quinone; benzophenone and derivatives thereof, ESACURE TZT® available from Lamberti, a mixture of 2,4,6-trimethylbenzophenone and 4-methylbenzophenone, Darocur®BP, benzophenone, 2-methylbenzophenone, 3-methylbenzophenone, 4-methyl benzophenone, 2,4,6-trimethylbenzophenone, 3-methyl-4'-phenyl-benzophenone, 2,4,6-trimethyl-4'-phenylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis (dimethylamino)-benzophenone, 4,4'-bis(diethylamino) benzophenone etc., acetophenone and derivatives thereof, e.g. 1-hydroxy-cyclohexyl-phenyl-ketone (IRGACURE®184) or IRGACURE®500 (a mixture of IRGACURE®184 with benzophenone); or 2-hydroxy-2-methyl-1-phenyl-propanone (DAROCUR® 1173), 2-hydroxy-1-[3-[4-(2-hydroxy-2-methyl-propionyl)-phenyl]-1,1,3-trimethyl-indan-5-yl]-2-methyl-propan-1-one, 4-aroyl-1,3-dioxolane, 1-(4-dodecylbenzoyl)-1-hydroxy-1-methyl-ethane, 1-(4-isopropylbenzoyl)-1-hydroxy-1-methyl-ethane, α-hydroxy- or α-amino-acetophenone such as, for example, 2-methyl-1[4-(methylthio)phenyl]-2-morpholinopropan-1-one (IRGACURE®907), 2-benzyl-2-dimethylamino-1-(4-morpholinophenyl)-butanone-1 (IrGACURE®369), 2-dimethylamino-2-(4-methyl-benzyl)-1-(4-morpholin-4-yl-phenyl)-butan-1-one (IRGACURE®379), (4-(2-hydroxyethyl)aminobenzoyl)-1-benzyl-1-dimethylaminopropane), (3,4-dimethoxybenzoyl)-1-benzyl-1-dimethylaminopropane, 1-[4-(2-hydroxyethoxy)-phenyl]-2-hydroxy-2-methyl-1-propan-1-one (IRGACURE®2959), 2,2-dimethoxy-1,2-diphenylethan-1-one (IRGACURE®651), 2-hydroxy-1-{4-[4-(2-hydroxy-2-methyl-propionyl)-benzyl]-phenyl}-2-methyl-propan-1-one (IRGACURE®127), 2-benzyl-1-(3,4-dimethoxy-phenyl)-2-dimethylamino-butan-1-one, 2-hydroxy-1-{4-[4-(2-hydroxy-2-methyl-propionyl)-phenoxy]-phenyl}-2-methyl-propan-1-one, ESACURE®KIP provided by F. Lamberti, 2-hydroxy-1-{1-[4-(2-hydroxy-2-methyl-propionyl)-phenyl]-1,3,3-trimethyl-indan-5-yl}-2-methyl-propan-1-one; benzoin alkyl ethers and benzil ketal, such as, for example, benzil dimethyl ketal, phenyl glyoxalate and derivatives thereof, e.g. oxo-phenyl-acetic acid 2-[2-(2-oxo-2-phenyl-acetoxy)-ethoxy]-ethyl ester (IRGACURE®754); mono- or bis-acylphosphine oxide, such as, for example, (2,4,6-trimethyl-benzoyl)-phenyl-phosphine oxide (DAROCUR®TPO), bis(2,6-dimethoxybenzoyl)-(2,4,4-trimethyl-pent-1-yl)phosphine oxide, bis(2,4,6-trimethylbenzoyl)-phenyl-phosphine oxide (IRGACURE®819) or bis(2, 4,6-trimethylbenzoyl)-(2,4-dipentyloxyphenyl)phosphine oxide; or oximeesters, e.g. 1,2-octanedione 1-[4-(phenylthio) phenyl]-2-(O-benzoyloxime) (IRGACURE® OXE01), ethanone 1-[9-ethyl-6-(2-methylbenzoyl)-9H-carbazol-3-yl]-1-(O-acetyloxime) (IRGACURE® OXE02), 9H-thioxanthene-2-carboxaldehyde 9-oxo-2-(O-acetyloxime), peresters, e.g. benzophenone tetracarboxylic peresters as described for example in EP 126541, as well as any other radical photoinitiator known to the art-skilled person.

The DAROCUR® and IRGACURE® compounds are available from Ciba Specialty Chemicals.

Other additional components can be, for example, hydroxy-functional components, such as alcohols, polyester polyols, polyether polyols, hydroxy-group-containing polyurethanes, castor oil, etc . . . Examples thereof include aliphatic and cycloaliphatic polyols, such as alkylene diols having preferably from 2 to 12 carbon atoms, e.g. ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-di-hydroxy-methylcyclohexane, glycerol, tris(β-hydroxy-ethyl) amine, trimethylolethane, tri-methylolpropane, pentaerythritol, dipentaerythritol and sorbitol. The polyols can be partially or fully esterified by one or by different unsaturated carboxylic acids, it being possible for the free hydroxyl groups in partial esters to have been modified, e.g. etherified, or esterified by other carboxylic acids. Examples of esters include: trimethylolpropane triacrylate, trimethylolethane triacrylate, trimethylolpropane trimethacrylate, trimethylolethane trimeth-acrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, or mixtures thereof.

The sulphonium salt compounds of formula I can also be used, for example, as photo-activatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxy-group-containing acrylic or polyester resin, a partially hydrolysed polyvinylacetal or a polyvinyl alcohol. That type of polycondensation of polysiloxanes is described, for example, in J. J. Lebrun, H. Pode, Comprehensive Polymer Science Vol. 5, page 593, Pergamon Press, Oxford, 1989.

Examples of compounds whose solubility increases in a developer under the action of acid, i.e., component (a2) include oligomers, polymers and copolymers that can be obtained by co-polymerisation of, for example, the following monomers: non-cyclic or cyclic secondary and tertiary alkyl (meth)acrylates, such as tert-butyl acrylate, tert-butyl methacrylate, 3-oxo-cyclohexyl(meth)acrylate, tetrahydropyranyl (meth)acrylate, 2-methyl-2-adamantyl(meth)acrylate, cyclohexyl(meth)acrylate, norbornyl(meth)acrylate, isobornyl methacrylate, 5-norbornene-2-tert-butyl ester, 8-ethyl-8-tricyclodecanyl(meth)acrylate, (2-tetrahydropyranyl)oxynorbornylalcohol acrylates, (2-tetrahydropyranyl)oxymethyltricyclododecane-methanol methacrylates, trimethylsilylmethyl(meth)acrylates, (2-tetrahydropyranyl)oxynorbornylalcohol acrylates, (2-tetrahydropyranyl)oxymethyltricyclododecanemethanol methacrylates, trimethylsilylmethyl (meth)acrylate, o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes, such as o-/m-/p-tert-butoxycarbonylstyrene, o-/m-/p-(3-oxocyclohexyloxycarbonyl)styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes, such as o-/m-/p-tert-butoxycarbonyloxystyrene, o-/m-/p-(3-oxocyclohexyloxycarbonyloxy)styrene, o-/m-/p-(1-methyl-1-phenylethoxycarbonyloxy)-styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes, such as o-/m-/p-butoxycarbonylmethoxystyrene, p-tert-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates, such as isopropenyl acetate and derivatives thereof, 5-norbornenyl-2-tert-butyl ester; also monomers that carry acid-labile groups having low activation energy, such as, for example, p- or m-(1-methoxy-1-methylethoxy)styrene, p- or m-(1-methoxy-1-methylethoxy)-methylstyrene, p- or m-(1-methoxy-1-methylpropoxy)styrene, p- or m-(1-methoxy-1-methyl-propoxy)methylstyrene, p- or m-(1-methoxyethoxy)styrene, p- or m-(1-methoxyethoxy)-methylstyrene, p- or m-(1-ethoxy-1-methylethoxy)styrenes, p- or m-(1-ethoxy-1-methyl-ethoxy)methylstyrene, p- or m-(1-ethoxy-1-methylpropoxy)styrene, p- or m-(1-ethoxy-1-methylpropoxy)methylstyrene, p- or m-(1-ethoxyethoxy)styrene, p- or m-(1-ethoxyethoxy)-methylstyrene, p-(1-ethoxyphenylethoxy)styrene, p- or m-(1-n-propoxy-1-methylethoxy)-styrene, p- or m-(1-n-propoxy-1-methylethoxy)methylstyrene, p- or m-(1-n-propoxyethoxy)styrene, p- or m-(1-n-propoxyethoxy)methylstyrene, p- or m-(1-isopropoxy-1-methylethoxy)-styrene, p- or m-(1-isopropoxy-1-methylethoxy)methylstyrene, p- or m-(1-isopropoxyethoxy)-styrene, p- or m-(1-isopropoxyethoxy)methylstyrene, p- or m-(1-isopropoxy-1-methyl-propoxy)styrene, p- or m-(1-isopropoxy-1-methylpropoxy)-methylstyrene, p- or m-(1-iso-propoxypropoxy)styrene, p- or m-(1-isopropoxypropoxy)-methylstyrene, p- or m-(1-n-butoxy-1-methylethoxy)styrene, p- or m-(1-n-butoxyethoxy)styrene, p- or m-(1-isobutoxy-1-methyl-ethoxy)-styrene, p- or m-(1-tert-butoxy-1-methylethoxy)styrene, p- or m-(1-n-pentyloxy-1-methylethoxy)styrene, p- or m-(1-isoamyloxy-1-methyl-ethoxy)styrene, p- or m-(1-n-hexyloxy-1-methylethoxy) styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)-styrene, p- or m-(1-trimethylsilyloxy-1- methylethoxy)methylstyrene. Further examples of polymers having alkoxyalkyl ester acid-labile groups can be found in U.S. Pat. No. 5,225,316 and EP 829766. Examples of polymers having acetal protecting groups are described, for example, in U.S. Pat. No. 5,670,299, EP 780 732, U.S. Pat. Nos. 5,627,006, 5,558,976, 5,558,971, 5,468,589, EP 704762, EP 762206, EP 342498, EP 553737 and in ACS Symp. Ser. 614, Microelectronics Technology, pp. 35-55 (1995), J. Photopolymer Sci. Technol. Vol. 10, No. 4 (1997), pp. 571-578, J. Photopolymer Sci. Technol. Vol. 12, no. 4 (1999) pp. 591-599 and in "Proceedings of SPIE", Advances in Resist Technology and Processing XVII, Vol. 3999, Part One, pp. 579-590, 28. Feb.-1. March 2000. The polymers suitable in the composition according to the invention are not, however, limited thereto.

The monomers having an acid-labile group can, where appropriate, also be co-polymerised with other free-radically polymerisable monomers that do not carry acid-labile groups, such as, for example, styrene, acrylonitrile, methyl(meth) acrylate, (meth)acrylic acid, 4-hydroxystyrene, 4-acetoxystyrene, 4-methoxystyrene, 4-vinylcyclohexanol, norbornene, ethylnorbornene and maleic acid anhydride, in order to establish specific solubility properties and adhesive properties. Alternatively, the acid-labile groups can be introduced only subsequently in a polymer-analogous reaction. It is also known to the person skilled in the art that the prepolymer can be modified in targeted manner before such a polymer-analogous reaction, for example by partial hydrogenation, partial alkylation, partial acetylation. That is to say, that the polymer having acid-labile groups does not, in every case, have to be synthesised from monomers by copolymerisation.

It is also possible to introduce acid-labile crosslinking, as described, for example, in H.-T. Schacht, P. Falcigno, N. Muenzel, R. Schulz and A. Medina, ACS Symp. Ser. 706 (Micro- and Nanopatterning Polymers), pp. 78-94, 1997; H.-T. Schacht, N. Muenzel, P. Falcigno, H. Holzwarth and J. Schneider, J. Photopolymer Science and Technology, Vol. 9, (1996), 573-586. Such acid-crosslinked systems are preferred in resist applications from the standpoint of heat stability. Such acid-labile crosslinking can also be obtained by the reaction of phenol-group-containing polymers, such as, for example, 4-hydroxystyrene co-polymers, with di- and polyfunctional vinyl ethers.

Other examples of component (a2) that increase their solubility in an alkaline developer upon reaction with acid are monomeric compounds, such as, for example, carboxylic acids and phenol-group-containing compounds, in which the carboxylic acid group or phenolic OH group, respectively, has been blocked by acid-labile protecting groups. Such acid-labile blocking can be effected, for example, by conversion of the carboxyl group into a tert-butyl ester group, a 2-methyl-2-adamantyl ester group, an 8-ethyl-8-tricyclodecanyl ester group, a tetrahydropyranyl ester group or some other acid-cleavable ester group. Phenolic OH groups can be blocked according to known processes by conversion, e.g. into acid-cleavable tert-butylcarbonate groups, silyl ethers, acetal groups and ketal groups.

The invention relates also to a radiation-sensitive composition wherein component (a2) is at least one compound selected from the group of cycloaliphatic copolymers, 4-hydroxy-phenyl-group-containing copolymers, maleic acid anhydride-containing copolymers and acrylic acid-, acrylic acid ester- and methacrylic acid ester-containing copolymers, with the proviso that those copolymers carry functional groups that increase the solubility of the polymer in an alkaline developer after reaction with an acid.

In the compositions according to the invention, the photoinitiator (b) is advantageously used in an amount of from 0.05% to 15%, e.g. from 0.5% to 10%, preferably from 1% to 5%, based on the composition.

The compositions according to the invention can be used in numerous applications, for example in cationically radiation-curable printing inks, in cationically radiation-curable coating compounds which may or may not be pigmented, in cationically radiation-curable adhesives, coatings and mouldings, including glass fibre-reinforced and carbon fibre-reinforced composites and inner and outer layers of printed circuit boards.

The compositions according to the invention include also adhesives, as used, for example, for adhesive bonding (DVD bonding) in the manufacture of digital versatile disks (DVD) and as described, for example, in: WO 99/66506, WO 99/63017, JP 11241055 A2 Heisei, JP 11181391 A2 Heisei, WO 98/31765, and also as radiation-curable laminating adhesives for flexible packaging (see, e.g., U.S. Pat. No. 5,328, 940), optical adhesives (e.g. German Patent Application DD 225985) and pressure-sensitive adhesives (e.g. U.S. Pat. No. 4,988,741 and EP 115870).

The compositions according to the invention are also suitable for use in uv-curing adhesives, e.g. in the preparation of pressure-sensitive adhesives, laminating adhesives, hot-melt adhesives, moisture-cure adhesives, silane reactive adhesives or silane reactive sealants and the like, and related applications.

Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

Hotmelt adhesives are interesting as pressure sensitive adhesives and suitable to replace the use of solvent base compositions, which from an environmental point of view are unwanted. The hotmelt extrusion process in order to achieve the high flow viscosity necessitates high application temperatures. The compositions of the present invention comprising isocyanates are suitable as crosslinkers in the preparation of a hotmelt coating, where the crosslinkers enter into a chemical reaction with the functional comonomers of the (meth)acrylate PSA. After the coating operation, the PSAs are first crosslinked thermally, or implementing the dual crosslinking mechanism, the PSA is subsequently crosslinked with UV light. UV crosslinking irradiation takes place by means of shortwave ultraviolet radiation in a wavelength range from 200 to 400 nm, even expanding in the visible range, e.g. up to 650 nm, depending on the source of the UV radiation equipment, as well as on the photolatent metal catalyst. Such systems and processes are for example described in US 2006/0052472, the disclosure of which hereby is incorporated by reference.

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

Depending on the kind of application of the compounds of formula I according to the present invention it may be advantageous to add appropriate further additives, sensitzers and/or photoinitiators. Such additives, sensitizers and photoinitiators are customary in the art and known to the person skilled in the art.

The photopolymerisable mixtures can comprise various additives (c) in addition to the photoinitiator. Examples thereof include thermal inhibitors, light stabilisers, optical brighteners, fillers and pigments, as well as white and coloured pigments, dyes, antistatics, adhesion promoters, wetting agents, flow auxiliaries, lubricants, waxes, anti-adhesive agents, dispersants, emulsifiers, anti-oxidants; fillers, e.g. talcum, gypsum, silicic acid, rutile, carbon black, zinc oxide, iron oxides; reaction accelerators, thickeners, matting agents, antifoams, and other adjuvants customary, for example, in lacquer and coating technology.

The formulations can also comprise dyes and/or white or coloured pigments as additional additives (c). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketo-pyrrolo-pyrrole, isoindolinone, e.g. tetrachloro-isoindolinone, isoindoline, dioxazine, benzimidazolone and quinophthalone pigments.

The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation. Such compositions then show, by the colour change, that they have been irradiated and can be used, for example, as irradiation dose indicators, e.g. for UV radiation, electron beams, X-rays, etc.

The choice of additives will depend upon the field of use in question and upon the properties desired for that field. The additives (c) described above are customary in the art and are accordingly used in amounts customary in the art.

The compositions according to the present invention as component (c) also may comprise a stabilizer for the compounds of the formula I, e.g. from the hindered nitroxyl or phosphite type as are for example described as stabilizers for iodonium salts in WO 05/070989.

Examples for said stabilizer compounds are organic phosphorus stabilizers as disclosed for example in U.S. Pat. No. 6,444,733, the disclosure of which is hereby incorporated by reference. Organic phosphorus stabilizers are known and many are commercially available. Other examples for said stabilizer compounds are hindered nitroxyl stabilizers, or hindered nitroxides, as are well known in the art and are disclosed for example in U.S. Pat. Nos. 6,337,426 and, 5,254,760, the relevant disclosures of which are hereby incorporated by reference.

Other suitable stabilizers (c) for the sulphonium salts of the formula I are for example disclosed in WO 99/35188. Examples are tertiary and sterically hindered amines, such as the TINUVIN® products, provided by Ciba Specialty Chemicals, in particular TINUVIN® 144 and TINUVIN® 292.

Acceleration of the photopolymerisation can also be effected by adding as further additives (d) photosensitisers that shift or broaden the spectral sensitivity. These are especially aromatic carbonyl compounds, such as, for example, benzophenone, thioxanthone, and especially also isopropylthioxanthone, phenothiazine derivatives, anthraquinone and 3-acyl-coumarin derivatives, terphenyls, styryl ketones, and 3-(aroylmethylene)-thiazolines, camphorquinone, and also eosin, rhodamine and erythrosin dyes, and anthracene derivatives, such as, for example, 9-methylanthracene, 9,10-dimethylanthracene, 9,10-diethoxyanthracene, 9,10-dibutyloxyanthracene, 9-methoxyanthracene, 9-anthracenemethanol, especially 9,10-dimethoxy-2-ethyl-anthracene, 9,10-dibutyloxyanthracene and 9,10-diethoxyanthracene. Further suitable photosensitisers are mentioned, for example, in WO 98/47046.

Subject of the invention also are radiation-sensitive compositions as described above, additionally to components (a1) or (a2) and (b) comprising at least one sensitizer compound (d), in particular benzophenone, thioxanthone, anthracene or derivatives thereof.

Further examples of suitable photosensitisers (d) are disclosed in WO 06/008251, page 36, line 30 to page 38, line 8, the disclosure of which is hereby incorporated by reference.

It is also possible to use electron donor compounds, such as, for example, alkyl- and aryl-amine donor compounds, in the composition. Such compounds are, for example, 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene. Such donor compounds are preferably used in a concentration of from 0.01 to 5%, especially in a concentration of from 0.05 to 0.50%, based on the formulation.

The sensitisers (d) described above are customary in the art and are accordingly used in amounts customary in the art, preferably in a concentration of from 0.05 to 5%, especially in a concentration of from 0.1 to 2%, based on the composition.

The compositions according to the invention may additionally comprise further photo-initiators (e), such as, for example, cationic photoinitiators, photo acid-formers and free-radical photoinitiators as co-initiators in amounts of from 0.01 to 15%, preferably from 0.1 to 5%.

Examples of cationic photoinitiators and acid-formers are phosphonium salts, diazonium salts, pyridinium salts, iodonium salts, such as for example tolylcumyliodonium tetrakis (pentafluorophenyl)borate, 4-[(2-hydroxy-tetradecyloxy)phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate (IRGACURE®250, Ciba Specialty Chemicals), 4-octyloxyphenyl-phenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable; further sulphonium salts, obtainable, for example, under the trade names CYRACURE® UVI-6990, CYRACURE® UVI-6974 (Union Carbide), DEGACURE® KI 85 (Degussa), SP-55, SP-150, SP-170 (Asahi Denka), GE UVE 1014 (General Electric), SarCat®KI-85 (=triarylsulphonium hexafluorophosphate; Sartomer), SarCat® CD 1010 (=mixed triarylsulphonium hexafluoroantimonate; Sartomer); SarCat® CD 1011(=mixed triarylsulphonium hexafluorophosphate; Sartomer); ferrocenium salts, e.g. ($\eta^6$-isopropylbenzene)($\eta^5$-cyclopentadienylyiron-II hexafluorophosphate, nitrobenzylsulphonates, alkyl- and aryl-N-sulphonyloxyimides and further known alkylsulphonic acid esters, haloalkylsulphonic acid esters, 1,2-disulphones, oxime sulphonates, benzoin tosylate, tolylsulphonyloxy-2-hydroxy-2-methyl-1-phenyl-1-propanone and further known beta-ketosulphones, beta-sulphonylsulphones, bis(alkylsulphonyl)diazomethane, bis(4-tert-butyl-phenyl-sulphonyl)-diazomethane, benzoyl-tosyl-diazomethane, iminosulphonates and imido-sulphonates and trichloromethyl-s-triazines and other haloalkyl-group-containing compounds. Examples of further suitable additional photolatent acids (b1) include the examples of cationic onic photoinitiators and acid-formers as given in WO 04/074242, page 38, line 10 to page 41, line 14, as well as the compounds disclosed in the examples of WO 04/074242, the relevant disclosure of which is incorporated herein by reference.

Examples of free-radical photoinitiators as co-initiators are compounds as described above.

The compositions according to the invention may be used for a variety of purposes, for example as printing inks, such as screen-printing inks, flexo printing inks or offset printing inks, as clear lacquer, as coloured surface-coating compositions, as white surface-coating compositions, e.g. for wood or metal, as powder coating compositions, as paint, inter alia for paper, wood, metal or plastics, as daylight-curable paint for marking structures and roads, for photographic reproduction processes, for holographic recording materials, for image-recording processes or for the production of printing plates that are to be developed with organic solvents or using aqueous-alkaline media, in the production of masks for screen-printing, as dental filling compounds, as radiation-curable adhesives, as pressure-sensitive adhesives, as anti-adhesive coatings, as laminating resins, as photoresists, e.g. galvanoresists, etch resists or permanent resists, liquid films and dry films, as photostructurable dielectrics, and as solder masks for electronic circuits, as resists in the manufacture of colour filters for any type of screen or for producing structures in the manufacture of plasma displays and electroluminescent displays, in the manufacture of optical switches, optical gratings (interference gratings), in the coating or sealing of electronic components, e.g. as electroinsulating compounds, or as coatings for optical fibres, for coil coating, as indicator systems for UV radiation, X-rays and electron beams, and in the manufacture of three-dimensional articles, e.g. for stereolithography and for composites, e.g. for composites reinforced with glass or carbon or graphite fibres. The compositions are also suitable for the manufacture of optical lenses, e.g. contact lenses or Fresnel lenses, and also in the manufacture of medical apparatus, aids or implants.

The photocurable compositions according to the invention are suitable, for example, as coating materials for all kinds of substrates, for example wood, textiles, paper, ceramics, glass, marble, plastics, such as polyester, polyethylene terephthalate, polyolefins or cellulose acetate, especially in the form of films, and metals, such as Al, Cu, Ni, Fe, Zn, Mg or Co and GaAs, Si or $SiO_2$, to which a coating is to be applied or an image is to be applied by imagewise exposure, or to which a structured resist layer is to be applied.

The coating of the substrates can be effected by applying a liquid composition, a solution or suspension to the substrate. The choice of solvent in a solution and the concentration are governed chiefly by the nature of the composition and by the coating method. The solvent should be inert, that is to say it should not enter into any chemical reaction with the components and it should be capable of being removed again upon drying after the coating operation.

Examples of suitable solvents are ketones, ethers and esters, such as methyl ethyl ketone, isobutyl methyl ketone, cyclopentanone, cyclohexanone, 2-heptanone, methyl amyl ketone, N-methylpyrrolidone, gamma-butyrolactone, dioxane, tetrahydrofuran, 2-methoxyethanol, 2-ethoxyethanol, 1-methoxy-2-propanol, 1,2-dimethoxyethane, acetic acid ethyl ester, acetic acid n-butyl ester, propylene glycol monomethyl ether acetate, lactic acid ethyl ester, propylene carbonate and 3-ethoxy-propionic acid ethyl ester.

After coating of the substrates, the solvent is generally removed by drying.

The formulation is applied uniformly to a substrate by known coating methods, for example by spin-coating, immersion, knife coating, curtain pouring, brush application or spraying, especially by electrostatic spraying and reverse-roll coating, and by electrophoretic deposition. It is also possible to apply the photosensitive layer to a temporary flexible support and then coat the final substrate, e.g. a copper-laminated printed circuit board, by transferring the layer by lamination.

The amount applied (layer thickness) and the type of substrate (layer support) are dependent upon the desired field of use. The layer thickness range generally includes values from about 0.1 μm to more than 100 μm, preferably from 0.5 micrometre to 50 micrometres. In the manufacture of three-dimensional articles, e.g. by stereolithography, the dimensions of the articles that can be obtained are limited only by the size of the exposure apparatus.

The compounds of the formula I can be used as photosensitive acid donors in a photoresist. Resist systems can be prepared by image-wise irradiation of systems comprising compounds of formula I followed by a developing step.

The invention accordingly relates to a radiation-sensitive composition as described above, which is a chemically amplified photoresist composition.

In particular a chemically amplified photoresist composition comprising
 (a1) a compound which cures upon the action of an acid or
 (a2) a compound whose solubility is increased upon the action of an acid; and
 (b) as photosensitive acid donor, at least one compound of the formula I.

A chemically amplified photoresist is understood to be a resist composition wherein the radiation sensitive component provides a catalytic amount of acid which subsequently catalyses a chemical reaction of at least one acid-sensitive component of the resist. Resulting is the induction of a solubility difference between the irradiated and non-irradiated areas of the resist. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas in the resist. Thus, only a small concentration of the latent acid compound is necessary. As a result, resists with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally very stable (as long as not irradiated) in order not to generate acid during resist storage or during processing, which—in most cases—requires a post exposure bake step to start or to complete the catalytic reaction which leads to the solubility differential. It is also required to have good solubility of the latent catalysts in the liquid resist formulation and the solid resist film to avoid any particle generation which would interfere with the application of these resists in microelectronic manufacturing processes.

In contrast, positive resist materials which are not based on the chemical amplification mechanism must contain a high concentration of the latent acid, because it is only the acid concentration which is generated from the latent acid under exposure which contributes to the increased solubility of the exposed areas in alkaline developer. Because small acid concentration has only a little effect on the change of the dissolution rate of such resist and the reaction proceeds typically without a post exposure bake here, the requirements regarding chemical and thermal stability of the latent acid are less demanding than for chemically amplified positive resists. These resists require also a much higher exposure dose to generate enough acid for achieving sufficient solubility in the alkaline developer in the exposed areas and also suffer from the relatively low optical transparency (due to the high concentration of latent acid necessary) and thus also lower resolution and sloped images. Resist compositions based on non-chemically amplified technology are therefore inferior in photosensitivity, resolution and image quality compared to chemically amplified resists.

From the above it becomes clear that chemical and thermal stability of a latent catalyst is vital for a chemically amplified resist and that latent acids which can work in a non-chemically amplified resist are not necessarily applicable to chemically amplified resists because of the different acid diffusion requirements, acid strength requirements and thermal and chemical stability requirements.

The difference in resist solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive.

The invention accordingly relates to a chemically amplified positive photoresist.

If, on the other hand, the components of the formulation reduce the solubility of the composition after irradiation, the resist is negative.

The invention accordingly relates also to a chemically amplified negative photoresist.

A monomeric or polymeric compound which—in the unexposed areas—reduces the dissolution rate of an additionally present alkaline soluble binder resin in the resist formulation and which is essentially alkali-insoluble in the unexposed areas so that the resist film remains in the unexposed area after development in alkaline solution, but which is cleaved in the presence of acid, or is capable of being rearranged, in such a manner that its reaction product becomes soluble in the alkaline developer is referred to hereinafter as dissolution inhibitor.

The invention includes, as a special embodiment a chemically amplified positive alkaline-developable photoresist composition, comprising (a11) at least one polymer having acid-labile groups which decompose in the presence of an acid and increase the solubility of the resist film in an aqueous alkaline developer solution in the exposed area and (b) at least one compound of formula I.

A further embodiment of the invention is a chemically amplified positive alkaline-developable photoresist composition, comprising (a21) at least one monomeric or oligomeric dissolution inhibitor having at least one acidabile group which decomposes in the presence of acid and increases the solubility in an aqueous alkaline developer solution and at least one alkali-soluble polymer and, (b) at least one compound of formula I.

Another specific embodiment of the invention resides in a chemically amplified positive alkaline-developable photoresist composition, comprising (a11) at least one polymer having acid labile groups which decompose in the presence of an acid and increase the solubility in an alkaline developer in the exposed area;

(a21) a monomeric or oligomeric dissolution inhibitor, having at least one acid labile group, which decomposes in the presence of an acid and increase the alkaline solubility in the exposed area;

(a31) an alkali-soluble monomeric, oligomeric or polymeric compound at a concentration which still keeps the resist film in the unexposed area essentially insoluble in the alkaline developer, and (b) at least one compound of formula I.

The invention therefore pertains to a chemically amplified photoresist composition, comprising (a11) at least one polymer having an acid-labile group which decomposes in the presence of an acid to increase the solubility in aqueous alkaline developer solution and/or (a21) at least one monomeric or oligomeric dissolution inhibtor having an acid-labile group which decomposes in the presence of an acid to increase the solubility in aqueous alkaline developer solution and/or (a31) at least one alkali-soluble monomeric, oligomeric or polymeric compound; and (b) as photosensitive acid donor, at least one compound of formula I.

The compositions may comprise additionally to the component (b) other photosensitive acid donors (b1) and/or other additives (c).

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups (in the polymers (a11)) which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyloxycarbonyloxy-, trityl ester groups, silyl ester groups, alkoxymethyl ester groups, cumyl ester groups, acetal groups, ketal groups, tetrahydropyranyl ester groups, tetrafuranyl ester groups, tertiary alkyl ether groups, tertiary alkyl ester groups, and the like. Examples of such group include alkyl esters such as methyl ester and tert-butyl ester, acetal type esters such as methoxymethyl ester, ethoxymethyl enter, 1-ethoxyethyl ester, 1-isobutoxyethyl ester, 1-ispropoxyethyl ester, 1-ethoxypropyl ester, 1-(2-methoxyethoxy) ethyl ester, 1-(2-acetoxyethoxy)ethyl ester, 1-[2-(1-adamantyloxy)ethoxy]ethyl ester, 1-[2-(1-adamantylcarbonyloxy)ethoxy]ethyl ester, tetrahydro-2-furyl ester and tetrahydro-2-pyranyl ester, and alicyclic ester such as isobornyl ester.

The polymer having functional groups capable of decomposing by the action of an acid to enhance solubility of the resist film comprising this polymer in an alkaline developing solution, which can be incorporated in the positive resist according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP 254853, EP 878738, EP 877293, JP-A-2-25850, JP-A-3-223860, and JP-A-4-251259. The polymers which have acid labile groups pendant to the polymer backbone, in the present invention preferably are polymers which have, for example silylether, acetal, ketal and alkoxyalkylester groups (called "low-activation energy blocking groups") which cleave completely at relatively low post exposure bake temperatures (typically between room temperature and 110° C.) and polymers which have, for example, tert.-butylester groups or tert.-butyloxycarbonyl (TBOC) groups or other ester groups which contain a secondary or tertiary carbon atom next to the oxygen atom of the ester bond (called "high-activation energy blocking groups") which need higher bake temperatures (typically >110° C.) in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive resist compositions according to the invention.

Preferred polymers which have acid labile groups are polymers and co-polymers comprising the following distinct monomer types:

1) monomers that contain acid-labile groups which decompose in the presence of an acid to increase the solubility in aqueous alkaline developer solution and 2) monomers that are free of acid labile groups and free of groups that contribute to the alkaline solubility and/or 3) monomers that contribute to aqueous alkaline solubility of the polymer.

Examples of monomers of type 1) are:

non-cyclic or cyclic secondary and tertiary-alkyl (meth) acrylates such as butyl acrylate, including t-butyl acrylate, butyl methacrylate, including t-butyl methacrylate, 3-oxocyclohexyl(meth)acrylate, tetrahydropyranyl(meth)acrylate, 2-methyl-adamantyl(meth)acrylate, cyclohexyl(meth)acrylate, norbornyl(meth)acrylate, (2-tetrahydropyranyl)oxynorbonylalcohol acrylates, (2-tetrahydropyranyl)oxymethyltricyclododecanemethanol methacrylates, trimethylsilylmethyl (meth)acrylate, (2-tetrahydropyranyl)oxynorbonylalcohol acrylates, (2-tetrahydropyranyl)oxymethyltricyclododecanemethanol methacrylates, trimethylsilylmethyl (meth) acrylate o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes such as o-/m-/p-butoxycarbonylstyrene, including p-t-butoxycarbonylstyrene, o-/m-/p-(3-oxocyclohexyloxycarbonyl)-styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes such as o-/m-/p-butoxycarbonyloxystyrene, including p-t-butoxycarbonyloxystyrene, o-/m-/p-(3-oxocyclohexyloxycarbonyloxy)styrene, o-/m-/p-(1-methyl-1-phenylethoxycarbonyloxy)-styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes such as o/m/p-butoxycarbonylmethoxystyrene, p-t-butoxycarbonylmethoxystyrene, o-/m-/p-(3-oxocyclohexyloxycarbonylmethoxy)-styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)-styrene, p- or m-(1-methoxy-1-methylethoxy)-methylstyrene, p- or m-(1-methoxy-1-methylpropoxy)styrene, p- or m-(1-methoxy-1-methylpropoxy) methylstyrene, p- or m-(1-methoxyethoxy)-styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p- or m-(1-ethoxyethoxy)styrene, p- or m-(1-ethoxyethoxy)-methylstyrene, p-(1-ethoxyphenyl-ethoxy)styrene, p- or m-(1-n-propoxy-1-metylethoxy)styrene, p- or m-(1-n-propoxy-1-metylethoxy)-methylstyrene, p- or m-(1-n-propoxyethoxy) styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene, p- or m-(1-isopropoxy-1-methylpropoxy)styrene, p- or m-(1-isopropoxy-1-methylporpoxy)-methylstyrene, p- or m-(1-isopropoxypropoxy)styrene, p- or m-(1-isopropoxyporpoxy)-methylstyrene, p- or m-(1-n-butoxy-1-methylethoxy)styrene, p- or m-(1-n-butoxyethoxy)styrene, p- or m-(1-isobutoxy-1-methylethoxy)styrene, p- or m-(1-tert-butoxy-1-methylethoxy)styrene, p- or m-(1-n-pentoxy-1-methylethoxy)styrene, p- or m-(1-isoamyloxy-1-methylethoxy) styrene, p- or m-(1-n-hexyloxy-1-methylethoxy)styrene, p- or m-(1-cyclohexyloxy-1-methylethoxy)styrene, p- or m-(1- trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)-methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)styrene p- or m-(1-trimethylsilyloxy-1-methylethoxy)-methylstyrene. Other examples of polymers having alkoxyalkylester acid labile groups are given in U.S. Pat. No. 5,225,316 and EP 829766. Examples of polymers with acetal blocking groups are given in U.S. Pat. No. 5,670, 299, EP 780732, U.S. Pat. Nos. 5,627,006, 5,558,976, 5,558, 971, 5,468,589, EP 704762, EP 762206, EP 342498, EP 553737 and described in ACS Symp. Ser. 614, Microelectronics Technology, pp. 35-55 (1995) and J. Photopolymer Sci. Technol. Vol. 10, No. 4 (1997), pp. 571-578. The polymer used in the present invention is not limited thereto.

With respect to polymers having acetal groups as acid-labile groups, it is possible to incorporate acid labile crosslinks as for example described in H.-T. Schacht, P. Falcigno, N. Muenzel, R. Schulz, and A. Medina, ACS Symp. Ser. 706 (Micro- and Nanopatterning Polymers), p. 78-94, 1997; H.-T. Schacht, N. Muenzel, P. Falcigno, H. Holzwarth, and J. Schneider, J. Photopolymer Science and Technology, Vol. 9, (1996), 573-586. This crosslinked system is preferred from the standpoint of heat resistance of the resist patterns.

Monomers with high activation energy acid labile groups are, for example, p-tert.-butoxy-carbonyloxystyrene, tert.-butyl-acrylate, tert.-butyl-methacrylate, 2-methyl-2-adamantyl-methacrylate, isobornyl-methacrylate.

Monomers of type 1) suitable for ArF resist technology in particular include, for example, 2-methyl-2-adamantyl acrylate, 2-ethyl-2-adamantyl acrylate, 2-n-butyl-2-adamantyl acrylate, 2-n-butyl-2-adamantyl methacrylate, 2-methyl-2-adamantyl methacrylate and 2-ethyl-2-adamantyl methacrylate. Other monomers comprising acid-labile adamantyl moieties are disclosed in JP-A-2002-1265530, JP-A-2002-338627, JP-A-2002-169290, JP-A-2002-241442, JP-A-2002-145954, JP-A-2002-275215, JP-A-2002-156750, JP-A-2002-268222, JP-A-2002-169292, JP-A-2002-162745, JP-A-2002-301161, WO02/06901 A2, JP-A-2002-311590, JP-A-2002-182393, JP-A-2002-371114, JP-A-2002-162745.

Particular olefins with acid labile-group are also suitable for ArF resist technology as shown in, for example, JP-A-2002-308938, JP-A-2002-308869, JP-A-2002-206009, JP-A-2002-179624, JP-A-2002-161116.

Examples of comonomers according to type 2) are:

aromatic vinyl monomers, such as styrene, α-methylstyrene, acetoxystyrene, α-methylnaphthylene, acenaphthylene, vinyl alicyclic compounds such as vinyl norbornane, vinyl adamantine. vinyl cyclohexane, alkyl (meth)acrylates such as methyl methacrylate, (meth)acrylonitrile, vinylcyclohexane, vinylcyclohexanol, itaconic anhydride, as well as maleic anhydride.

Comonomers according to type 2) suitable for ArF resist technology in particular include, for example, alpha-acryloyloxy-gamma-butyrolactone, alpha-methacryloyloxy-gamma-butyrolactone, alpha-acryloyloxy-beta, beta-dimethyl-gamma-butyro-lactone, alpha-methacryloyloxy-beta, beta-dimethyl-gamma-butyrolactone, alpha-acryloyloxy-alpha-methyl-gamma-butyrolactone, alpha-methacryloyloxy-alpha-methyl-gamma-butyrolactone, beta-acryloyloxy-gamma, beta-methacryloyloxy-alpha-methyl-gamma-butyrolactone, 5-acryloyloxy-2,6-norbornanecarbolactone, 5-methacryloyloxy-2,6-norbolnanecarbolactone, 2-norbornene, methyl 5-norbornene-2-carboxylate, tert-butyl 5-norbornene-2-carboxylate, 1-cyrohexyl-1-methylethyl 5-norbornene-2-carboxylate, 1-(4-methylcyclohexyl)-1-methylethyl 5-norbornene-2-carboxylate, 1-methyl-1-(4-oxocyclohexyl)ethyl 5-norbornene-2-carboxylate, 1-(1-adamatyl)-1-methylethyl 5-norbornene-2-carboxylate, 1-methylcyclohexyl 5-norbornene-2-carboxylate, 2-methyl-2-adamantyl 5-norbornene-2-carboxylate, 2-ethy-2-adamantyl 5-norbornene-2-carboxylate, 5-norbornene-2,3-dicarboxylic acid anhydrate, 2(5H)-furanone. 3-vinyl-gamma-butyrolactone.

Examples of comonomers according to type 3) are:

vinyl aromatic compounds such as hydroxystyrene, acrylic acid compounds such as methacrylic acid, ethylcarbonyloxystyrene and derivatives of thereof. These polymers are described, for example, in U.S. Pat. Nos. 5,827,634, 5,625, 020, 5,492,793, 5,372,912, EP 660187, U.S. Pat. No. 5,679, 495, EP 813113 and EP 831369. Further examples are crotonic acid, isocrotonic acid, 3-butenoic acid, acrylic acid, 4-pentenoic acid, propiolic acid, 2-butynoic acid, maleic acid, fumaric acid, and acetylenecarboxylic acid. The polymer used in the present invention is not limited thereto.

Comonomers according to type 3) suitable for ArF resist technology in particular include, for example, 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 2-hydroxy-5-norbornene, 5-norbornene-2-carboxylic acid, 1-(4-hydroxycyclohexyl)-1-methylethyl 5-norbornene-2-carboxylate, 2-hydroxy-1-ethyl 5-norbornene-2-carboxylate, 5-norbornene-2-methanol.

Other monomers comprising lactone moieties suitable for ArF technology are disclosed in, for example, JP-A-2002-6502, JP-A-2002-145955, EP1127870A1, JP-A-2002-357905, JP-A-2002-296783. Other olefins suitable for ArF technology are published in, for example, JP-A-2002-351078, JP-A-2002-234918, JP-A-2002-251009, EP1127870A1, JP-A-2002-328475, JP-A-2002-278069, JP-A-2003-43689, JP-A-2002-202604, WO01/86353, JP-A-2002-23371, JP-A-2002-72484, JP-A-2002-202604, JP-A-2001-330959, JP-A-2002-3537, JP-A-2002-30114, JP-A-2002-278071, JP-A-2002-251011, JP-A-2003-122010, JP-A-2002-139837, JP-A-2003-195504, JP-A-2001-264984, JP-A-2002-278069, JP-A-2002-328475, U.S. Pat. Nos. 6,379,861, 6,599,677, US2002/119391, U.S. Pat. No. 6,277,538, US2003/78354.

The content of acid labile monomers in the polymer may vary over a wide range and depends on the amount of the other comonomers and the alkaline solubility of the deprotected polymer. Typically, the content of monomers with acid labile groups in the polymer is between 5 and 60 mol%. If the content is too small, too low development rates and residues of the resist in the exposed areas result. If the content of acid labile monomers is too high, resist patterns are poorly defined (eroded) after development and narrow features cannot be resolved anymore and/or the resist looses its adhesion to the substrate during development. Preferably the copolymers which have acid labile groups have a $M_W$ of from about 3,000 to about 200,000, more preferably from about 5,000 to about 50,000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a $M_W$ of from about 8,000 to about 50'000, and a molecular weight distribution of about 3 or less.

Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy-groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butylester group and 2-methyl-adamantyl group or an 1-ethoxy-ethoxy group and a tetrahydropyran-yloxy group. A mixture of a non-crosslinked resin and a crosslinked resin may also be used.

The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility.

Examples of polymer blends with polymers having different acid-labile groups are given in EP 780732, EP 679951 and U.S. Pat. No. 5,817,444.

Preferably monomeric and oligomeric dissolution inhibitors (a21) are used in the present invention.

The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3,000 or lower, preferably from 100 to 3,000, more preferably from 200 to 2'500.

Examples of monomeric and oligomeric dissolution inhibitors having acid-labile groups are described as formulae (I) to (XVI) in EP 0831369. Other suitable dissolution inhibitors having acid-labile groups are shown in U.S. Pat. Nos. 5,356,752, 5,037,721, 5,015,554, JP-A-1-289946, JP-A-1-289947, JP-A-2-2560, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-123567, JP-A-1-289946, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JP-A-3-279958, JP-A-3-279959, JP-A-4-1650, JP-A-4-1651, JP-A-11260, JP-A-4-12356, JP-A-4-12357 and Japanese Patent Applications Nos. 3-33229, 3-230790,3-320438, 4-254157, 4-52732, 4-103215, 4-104542, 4-107885, 4-107889, 4-152195, 4-254157, 4-103215, 4-104542, 4-107885, 4-107889, and 4-152195.

The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the resist film in the developer after exposure, or with a combination of both types of polymers.

In the case where the dissolution inhibitor having acid-labile groups is used in the present invention in combination with the sulfonium salts of formula I, the alkali-soluble polymer and/or the polymer having acid-labile groups, the amount of the dissolution inhibitor is from 3 to 55% by weight, preferably from 5 to 45% by weight, most preferably from 10 to 35% by weight, based on the total amount of all solid components of the photosensitive composition.

A polymer soluble in an aqueous alkali solution (a31) is preferably used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen-or alkyl-substituted poly(hydroxystyrene)s, hydroxystyrene/N-substituted maleimide copolymers, o/p- and m/p-hydroxystyrene copolymers, partially o-alkylated poly(hydroxystyrene)s, [e.g., o-methylated, o-(1-methoxy)ethylated, o-(1-ethoxy)ethylated, o-2-tetrahydropyranylated, and o-(t-butoxycarbonyl)methylated poly(hydroxystyrene)s having a degree of substitution of from 5 to 30 mol % of the hydroxyl groups], o-acylated poly(hydroxystyrene)s [e.g., o-acetylated and o-(t-butoxy)carbonylated poly(hydroxystyrene)s having a degree of substitution of from 5 to 30mol % of the hydroxyl groups], styrene/maleic anhydride copolymers, styrene/hydroxystyrene copolymers, α-methylstyrene/hydroxystyrene copolymers, carboxylated methacrylic resins, and derivatives thereof. Further suitable are poly(meth)acrylic acid [e.g. poly(acrylic acid)], (meth)acrylic acid/(meth)acrylate copolymers [e.g. acrylic acid/methyl acrylate copolymers, methacrylic acid/methyl methacrylate copolymers or methacrylic acid/methyl methacrylate/t-butyl methacrylate copolymers], (meth)acrylic acid/alkene copolymers [e.g. acrylic acid/ethylene copolymers], (meth)acrylic acid/(meth)acrylamide copolymers [e.g. acrylic acid/acrylamide copolymers], (meth)acrylic acid/vinyl chloride copolymers [e.g. acrylic acid/vinyl chloride copolymers], (meth)acrylic acid/vinyl acetate copolymer [e.g. acrylic acid/vinyl acetate copolymers], maleic acid/vinyl ether copolymers [e.g. maleic acid/methyl vinyl ether copolymers], maleic acid mono ester/methyl vinyl ester copolymers [e.g. maleic acid mono methyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/-vinyl chloride copolymers, maleic acid/vinyl acetate copolymers and maleic acid/alkene copolymers [e.g. maleic acid/ethylene copolymers and maleic acid/1-chloropropene copolymers]. However, the alkali-soluble polymer for use in the present invention should not be construed as being limited to these examples.

Especially preferred alkali-soluble polymers (a31) are novolak resins, poly(o-hydroxystyrene), poly(m-hydroxystyrene), poly(p-hydroxystyrene), copolymers of the respective hydroxystyrene monomers, for example with p-vinylcyclohexanol, alkyl-substituted poly(hydroxystyrene)s, partially o- or m-alkylated and o- or m-acylated poly(hydroxylstyrene)s, styrene/hydroxystyrene copolymer, and α-methylstyrene/hydroxystyrene copolymers. The novolak resins are obtained by addition-condensing one or more given monomers as the main ingredient with one or more aldehydes in the presence of an acid catalyst.

Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenylphenol, resorcinol, and naphthol. These compounds may be used alone or as a mixture of two or more thereof. The main monomers for novolak resins should not be construed as being limited to the above examples.

Examples of the aldehydes for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde.

These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1,000 to 30,000. If the weight-average molecular weight thereof is lower than 1,000, the film reduction at unexposed parts during development is liable to be large. If the weight-average molecular weight there of exceeds 50,000, the developing rate may be too low. The especially preferred range of the molecular weight of the novolak resin is from 2,000 to 20,000.

The poly(hydroxystyrene)s and derivatives and copolymers thereof shown above as alkali-soluble polymers other than novolak resins each have a weight-average molecular weight of 2,000 or higher, preferably from 4,000 to 200,000, more preferably from 5,000 to 50,000. From the standpoint of obtaining a polymer film having improved heat resistance, the weight-average molecular weight thereof is desirably at least 5,000 or higher.

Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the resist pattern suffers a considerable decrease in thickness, resulting in poor images and low resolution.

In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85%by weight, most preferably 60 to 80% by weight. If the amount thereof is smaller than 40% by weight, undesirable results such as reduced sensitivity are caused. On the other hand, if it exceeds 90% by weight, the resist pattern suffers a considerable decrease in film thickness, resulting in poor resolution and image reproduction.

The content of the sulfonium salts of formula I (component (b)) in the positive resist according to the present invention is preferably between 0.01% to 20% by weight, based on the total amount of all solid components in the photoresist.

The use of the sulfonium salts according to the invention in chemically amplified systems, which operates on the principle of the removal of a protecting group from a polymer, generally produces a positive resist. Positive resists are preferred over negative resists in many applications, especially because of their higher resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP 361906. For this purpose, the image-wise irradiated resist material is before the developing step treated with, for example, a gaseous base, thereby image-wise neutralizing the acid which has been produced. Then, a second irradiation, over the whole area, and thermal aftertreatment are carried out and the negative image is then developed in the customary manner.

The compounds of the formula I according to the present invention are in particular suitable as photolatent acids in the ArF resist technology, i.e. a technology using ArF excimer lasers (193 nm) for the imaging step. This technology requests the use of specific polymers/copolymers. Suitable formulations and the preparation of suitable polymer/copolymers are for example published in

*Proceeding of SPIE* 2438, 474 (1995); *Proceeding of SPIE* 3049, 44 (1997); *Proceeding of SPIE* 3333, 144 (1998); *J. Photopolym. Sci. Technol.* 14, 631 (2001); *Proceeding of SPIE* 3333, 546 (1998); *J. Photopolym. Sci. Technol.* 13, 601 (2000); JP2001-242627A; JP2001-290274A; JP2001-235863A; JP2001-228612A; *Proceeding of SPIE* 3333, 144 (1998); JP2001-5184A, commercially available as Lithomax alpha-7K from Mitsubishi Rayon; JP2001-272783A; U.S. patent application Ser. No. 09/413763 (filed 1999 Oct. 7); EP 1091249; JP2000-292917A; JP2003-241385A; *J. Photopolym. Sci. Technol.* 14, 631 (2001); *Proceeding of SPIE* 3333, 11 (1998); ACS 1998 (University of Texas); JP2001-290274A; JP2001-235863A; JP2001-228612A; *Proceeding of SPIE* 3999, 13 (2000); JP2001-296663A; U.S. patent application Ser. No. 09/567814 (filed 2000 May 9); EP 1128213; Proceeding of SPIE 3049, 104 (1997); *J. Photopolym. Sci. Technol.* 10, 521 (1997); JP2001-290274A; JP2001-235863A; JP2001-228612A; *Proceeding of SPIE* 4345, 680 (2001); *J. Vac. Sci. Technol.* B 16(6), p. 3716, 1998; *Proceeding of SPIE* 2724, 356 (1996); *Proceeding of SPIE* 4345, 67 (2001); *Proceeding of SPIE* 3333, 546 (1998); *Proceeding of SPIE* 4345, 87 (2001); *Proceeding of SPIE* 4345, 159 (2001); *Proceeding of SPIE* 3049, 92 (1997); *Proceeding of SPIE* 3049, 92 (1997); *Proceeding of SPIE* 3049, 92 (1997); Proceeding of SPIE 3999, 2 (2000);

Proceeding of SPIE 3999, 23 (2000); *Proceeding of SPIE* 3999, 54 (2000); *roceeding of SPIE* 4345, 119 (2001).

The formulations disclosed in the aforementioned publications are incorporated herein by reference. It is understood, that the compounds of the present invention are in particular suitable for use as photolatent acid in all the polymers/copolymers and compositions described in these cited publications.

The compounds of the formula I according to the present invention are suitable as photo-latent acids in the bi-layer resist. This technology requests the use of specific polymers/copolymers. Suitable formulations and the preparation of suitable polymer/copolymers are for example published in Proc. SPIE 4345, 361-370 (2001), Proc. SPIE 4345, 406-416 (2001), JP-A-2002-278073, JP-A-2002-30116, JP-A-2002-30118, JP-A-2002-72477, JP-A-2002-348332, JP-A-2003-207896, JP-A-2002-82437, US2003/65101, US2003/64321.

The compounds of the formula I according to the present invention are suitable as photo-latent acids in the multi-layer resist. This technology requests the use of specific polymers/copolymers. Suitable formulations and the preparation of suitable polymer/copolymers are for example published in JP-A-2003-177540, JP-A-2003-280207, JP-A-2003-149822, JP-A-2003-177544.

In order to make fine hole pattern, thermal flow process or chemical shrink technology, so-called RELACS (resolution enhancement lithography assisted by chemical shrink) process, are applied for chemically amplified resist. The compounds of the formula I according to the present invention are suitable as photolatent acids in the resists for thermal flow process or RELACS process. These technologies request the use of specific polymers/copolymers.

Suitable formulations and the preparation of suitable polymer/copolymers are for example published in JP-A-2003-167357, JP-A-2001-337457, JP-A-2003-66626, US2001/53496, JP-A-2003-202679, *Proceeding of SPIE* 5039, 789 (2003), *IEDM98, Dig.*, 333 (1998), *Proceeding Silicon Technology* 11, 12 (1999).

The compounds of the formula I according to the present invention are suitable as photo-latent acids in the $F_2$ resist technology, i.e. a technology using $F_2$ excimer lasers (157 nm) for the imaging step. This technology requests the use of specific polymers/copolymers which have high transparency at 157 nm. Examples of polymer suitable for this application are fluoropolymers described in, for example, Proc. SPIE 3999, 330-334 (2000), Proc. SPIE 3999, 357-364 (2000), Proc. SPIE 4345, 273-284 (2001), Proc. SPIE 4345, 285-295 (2001), Proc. SPIE 4345, 296-307 (2001), Proc. SPIE 4345, 327-334 (2001), Proc. SPIE 4345, 350-360 (2001), Proc. SPIE 4345, 379-384 (2001), Proc. SPIE 4345, 385-395 (2001), Proc. SPIE 4345, 417-427 (2001), Proc. SPIE 4345, 428-438 (2001), Proc. SPIE 4345, 439-447 (2001), Proc. SPIE 4345, 1048-1055 (2001), Proc. SPIE 4345, 1066-1072 (2001), Proc. SPIE 4690, 191-199 (2002), Proc. SPIE 4690, 200-211 (2002), Proc. SPIE 4690, 486-496 (2002), Proc. SPIE 4690, 497-503 (2002), Proc. SPIE 4690, 504-511 (2002), Proc. SPIE 4690, 522-532 (2002), US 20020031718, US 20020051938, US 20020055060, US 20020058199, US 20020102490, US 20020146639, US 20030003379, US 20030017404, WO 2002021212, WO 2002073316, WO 2003006413, JP-A-2001-296662, JP-A-2001-350263, JP-A-2001-350264, JP-A-2001-350265, JP-A-2001-356480, JP-A-2002-60475, JP-A-2002-90996, JP-A-2002-90997, JP-A-2002-155112, JP-A-2002-155118, JP-A-2002-155119, JP-A-2002-303982, JP-A-2002-327013, JP-A-2002-363222, JP-A-2003-2925, JP-A-2003-15301, JP-A-2003-2925, JP-A-2003-177539, JP-A-2003-192735, JP-A-2002-155115, JP-A-2003-241386, JP-A-2003-255544, US2003/36016, US2002/81499. Other suitable polymer for $F_2$ resist is silicon-containing polymers described in, for example, Proc. SPIE 3999, 365-374 (2000), Proc. SPIE 3999, 423-430 (2000), Proc. SPIE 4345, 319-326 (2001), US 20020025495, JP-A-2001-296664, JP-A-2002-179795, JP-A-2003-20335, JP-A-2002-278073, JP-A-2002-55456, JP-A-2002-348332. Polymers containing (meth)acrylonitrile monomer unit described in, for example, JP-A-2002-196495 is also suitable for $F_2$ resist.

The compounds of the formula I according to the present invention are suitable as photo-latent acids in the EUV resist, i.e. a technology using light source of extreme ultra violet (13 nm) for the imaging step. This technology requests the use of specific polymers/copolymers. Suitable formulations and the preparation of suitable polymer/copolymers are for example published in JP-A-2002-55452, JP-A-2003-177537, JP-A-2003-280199, JP-A-2002-323758, US2002/51932.

The compounds of the formula I according to the present invention are suitable as photo-latent acids in the EB (electron beam) or X-ray resist, i.e. a technology using EB or X-ray for the imaging step. These technologies request the use of specific polymers/copolymers. Suitable formulations and the preparation of suitable polymer/copolymers are for example published in JP-A-2002-99088, JP-A-2002-99089, JP-A-2002-99090, JP-A-2002-244297, JP-A-2003-5355, JP-A-2003-5356, JP-A-2003-162051, JP-A-2002-278068, JP-A-2002-333713, JP-A-2002-31892.

The compounds of the formula I according to the present invention are suitable as photo-latent acids in the chemically amplified resist for immersion lithography. This technology reduces minimum feature size of resist pattern using liquid medium between the light source and the resist as described in *Proceeding of SPIE* 5040, 667 (2003), *Proceeding of SPIE* 5040, 679 (2003), *Proceeding of SPIE* 5040, 690 (2003), *Proceeding of SPIE* 5040, 724 (2003).

The compounds of the formula I according to the present invention are suitable as photo-latent acids in the positive and negative photosensitive polyimide. This technology requests the use of specific polymers/copolymers. Suitable formulations and the preparation of suitable polymer/copolymers are for example published in JP-A-9-127697, JP-A-10-307393, JP-A-10-228110, JP-A-10-186664, JP-A-11-338154, JP-A-11-315141, JP-A-11-202489, JP-A-11-153866, JP-A-11-84653, JP-A-2000-241974, JP-A-2000-221681, JP-A-2000-34348, JP-A-2000-34347, JP-A-2000-34346, JP-A-2000-26603, JP-A-2001-290270, JP-A-2001-281440, JP-A-2001-264980, JP-A-2001-255657, JP-A-2001-214056, JP-A-2001-214055, JP-A-2001-166484, JP-A-2001-147533, JP-A-2001-125267, JP-A-2001-83704, JP-A-2001-66781, JP-A-2001-56559, JP-A-2001-33963, JP-A-2002-356555, JP-A-2002-356554, JP-A-2002-303977, JP-A-2002-284875, JP-A-2002-268221, JP-A-2002-162743, JP-A-2002-122993, JP-A-2002-99084, JP-A-2002-40658, JP-A-2002-37885, JP-A-2003-26919.

The formulations disclosed in the aforementioned publications are incorporated herein by reference. It is understood, that the compounds of the present invention are in particular suitable for use as photolatent acid in all the polymers/copolymers and compositions described in these cited publications.

Acid-sensitive components that produce a negative resist characteristically are especially compounds which, when catalysed by an acid (e.g. the acid formed during irradiation of the compounds of formulae I) are capable of undergoing a crosslinking reaction or a polymerization with themselves and/or with one or more further components of the composition. Compounds of this type are, for example, the known acid-curable resins, such as, for example, acrylic, polyester, alkyd, melamine, urea, epoxy, vinyl ether and phenolic resins or mixtures thereof. Amino resins, phenolic resins and epoxy resins are very suitable. Acid-curable resins of this type are generally known and are described, for example, in "Ullmann's Encyclopädie der technischen Chemie" [Ullmanns Enceclopedia of Technical Chemistry], 4th Edition, Vol. 15 (1978), p. 613-628. The crosslinker components should generally be present in a concentration of from 2 to 40, preferably from 5 to 30, percent by weight, based on the total solids content of the negative resist composition.

The invention thus includes, as a special embodiment, chemically amplified negative, alkali-developable photoresists, comprising (a41) an alkali-soluble resin as binder (a51) a component that when catalysed by an acid undergoes a crosslinking reaction with itself and/or with the binder, and (b) as photosensitive acid donor an sulfonate derivative of formula I.

The composition may comprise additionally to the component (b) other photosensitive acid donors (b1), other photoinitiators (d) and/or (c) other additives.

Especially preferred as acid-curable resins (a5) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N-hexa(methoxymethyl) melamine and tetramethoxymethyl glucoril and N,N'-dimethoxymethylurone are the acid-curable resins given the greatest preference.

The concentration of the compound of formula I in negative resists in general is from 0.1 to 30, preferably up to 20, percent by weight, based on the total solids content of the compositions. From 1 to 15 percent by weight is especially preferred.

Where appropriate, the negative compositions may comprise a film-forming polymeric binder (a4). This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$-$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and co-polymers based on ethylenically unsaturated phenols, for example homopolymers of vinyl- and 1-propenyl-substituted phenols, such as p-vinylphenol or p-(1-propenyl)phenol or copolymers of these phenols with one or more ethylenically unsaturated materials, for example styrenes. The amount of binder should generally be from 30 to 95 percent by weight or, preferably, from 40 to 80 percent by weight.

An especially preferred negative resist composition comprises from 0.5 to 15 percent by weight of an sulfonate derivative of formula I (component (b)), from 40 to 99 percent by weight of a phenolic resin as binder (component (a41)), for example one of those mentioned above, and from 0.5 to 30 percent by weight of a melamine resin (component (a51)) as crosslinking agent, the percentages relating to the solids content of the composition. With novolak or especially with polyvinyl phenol as binder, a negative resist having especially good properties is obtained.

Sulfonium salts can also be used as acid generators, which can be activated photochemically, for the acid-catalysed crosslinking of, for example, poly(glycidyl)methacrylates in negative resist systems. Such crosslinking reactions are described, for example, by Chae et al. in Pollimo 1993, 17(3), 292.

Suitable formulations and the preparation of suitable polymer/copolymers for the negative resist using the compounds of the formula I according to the present invention are for example published in JP-A-2003-43688, JP-A-2003-114531, JP-A-2002-287359, JP-A-2001-255656, JP-A-2001-305727, JP-A-2003-233185, JP-A-2003-186195, U.S. Pat. No. 6,576,394.

The compounds of the formula I according to the present invention are suitable as photo-latent acids in a chemically amplified solvent-developable negative photoresists. This technology requests the use of a specific component that when catalysed by an acid undergoes a crosslinking reaction or a polymerization with itself and/or with other components in the formulation. Suitable formulations are for example published in U.S. Pat. Nos. 4,882,245, 5,026,624, 6,391,523.

The positive and the negative resist compositions may comprise in addition to the photosensitive acid donor compound of formula I further photosensitive acid donor compounds (b1), further additives (c), other photoinitiators (d), and/or sensitizers (e).

Therefore, subject of the invention also are chemically amplified resist compositions as described above, in addition to components (a) and (b), or components (a11), (a21), (a31) and (b), or components (a41), (a51) and (b) comprising further additives (c), further photosensitive acid donor compounds (b1), other photoinitiators (d), and/or sensitizers (e).

Sulfonium salts of the present invention in the positive and negative resist can also be used together with other, known photolatent acids (b1), for example, onium salts, 6-nitrobenzylsulfonates, bis-sulfonyl diazomethane compounds, cyano group-containing oximesulfonate compounds., etc. Examples of known photolatent acids for chemically amplified resists are described in U.S. Pat. Nos. 5,731,364, 5,800, 964, EP 704762, U.S. Pat. Nos. 5,468,589, 5,558,971, 5,558, 976, 6,004,724, GB 2348644 and particularly in EP 794457 and EP 795786.

If a mixture of photolatent acids is used in the resist compositions according to the invention, the weight ratio of sulfonium salts of formula I to the other photolatent acid (b1) in the mixture is preferably from 1:99 to 99:1.

Examples of photolatent acids which are suitable to be used in admixture with the compounds of formula I, e.g. as component (b1), are (1) onium salt compounds, for example, iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxyphenyl)benzylmethylsulfonium toluenesulfonate and the like; the iodonium cation may also be 4-Methylphenyl-4'-isobutylphenyliodonium or 4-Methylphenyl-4'-isopropylphenyliodonium. Particularly preferred are triphenylsulfonium triflate, diphenyliodonium hexafluoroantimonate. Other examples are described in JP-A-2002-229192, JP-A-2003-140332, JP-A-2002-128755, JP-A-2003-35948, JP-A-2003-149800, JP-A-2002-6480, JP-A-

2002-116546, JP-A-2002-156750, U.S. Pat. No. 6,458,506, US2003/27061, U.S. Pat. No. 5,554,664.

(2) halogen-containing compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methozyphenyl-bis(trichloromethyl)-s-triazine, naphthyl-bis-(trichloromethyl)-s-triazine and the like; 1.1-bis(4-chlorophnyl)-2,2,2-trichloroethane; and the like.

(3) sulfone compounds, for example of the formula

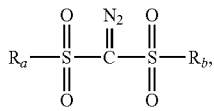

wherein $R_a$ and $R_b$ independently of one another are alkyl, cycloalkyl or aryl, each of which may have at least one substituent, e.g.

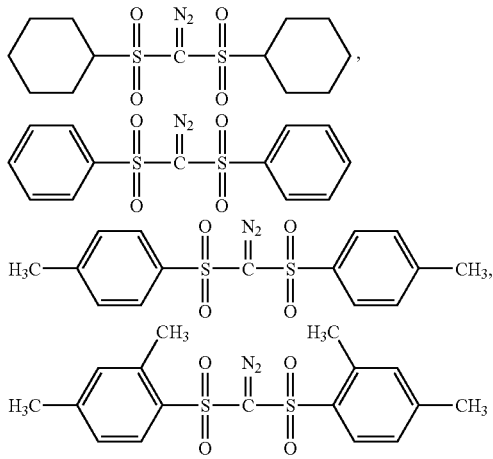

Such compounds are disclosed for example in US 2002/0172886-A, JP-A-2003-192665, US200219663. More examples are β-ketosulfones, β-sulfonylsulfones and their α-diazo derivatives and the like. Preferred are phenacylphenylsulfone, mesitylphenacylsulfone, bis(phenylsulfonyl)methane, bis(phenylsulfonyl)diazomethane.

(4) sulfonate compounds, for example alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy)diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide, N-(camphanylsulfonyloxy)succinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)bicyclo-[2,2,1]-hept-5-ene-2,3-dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-[2,2,1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2,2,1]-hept-5-ene-2,3-dicarboximide, N-(4-methylphenylsulfonyloxy)-7-oxabicyclo-[2,2,1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy)succinimide, N-(2-trifluoromethylphenylsulfonyloxy)naphthylimide, N-(2-trifluoromethylphenylsulfonyloxy)diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like.

Other suitable sulfonate compounds preferably are, for example, benzoin tosylate, pyrogallol tristriflate, pyrogallolomethanesulfonic acid triester, nitrobenzyl-9,10-diethyoxyanthracene-2-sulfonate, α-(4-toluene-sulfonyloxyimino)-benzyl cyanide, α-(4-toluene-sulfonyloxyimino)-4-methoxybenzyl cyanide, α-(4-toluene-sulfonyloxyimino)-2-thienylmethyl cyanide, α-(methanesulfonyloxyimino)-1-cyclohexenylacetonitrile, α-(butylsulfonyloxyimino)-1-cyclopentenylacetonitrile, (4-methylsulfonyloxyiminocyclohexa-2,5-dienylidene)-phenyl-acetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-propylsulfonyloxyimino-5H-thiophen-2-ylidene)-(2-methylphenyl)-acetonitrile, (5-(p-toluenesulfonyloxyimino)-5H-thiophen-2-ylidene)-(2-methylphenyl)-acetonitrile, (5-(10-camphorsulfonyloxyimino)-5H-thiophen-2-ylidene)-(2-methylphenyl)-acetonitrile, (5-methylsulfonyloxyimino-5H-thiophen-2-ylidene)-(2-chlorophenyl)-acetonitrile, 2,2,2-trifluoro-1-{4-(3-[4-{2,2,2-trifluoro-1-(1-propanesulfonyloxyimino)-ethyl}-phenoxy]-propoxyyphenyl}-ethanone oxime 1-propanesulfonate, 2,2,2-trifluoro-1-{4-(3-[4-{2,2,2-trifluoro-1-(1-p-toluenesulfonyloxyimino)-ethyl}-phenoxy]-propoxyyphenyl}-ethanone oxime 1-p-toluenesulfonate and the like.

In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy)naphthylimide, N-(2-trifluoromethylphenylsulfonyloxy)phthalimide, N-(trifluoromethylsulfonyloxy)-bicyclo-[2,2,1]-hept-5-ene-2,3-dicarboximide, N-(camphanylsulfonyloxy)naphthylimide, N-(2-trifluoromethylphenylsulfonyloxy)phthalimide and the like.

(5) Quinonediazide compounds, for example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2- quinonediazidesulfonic acid esters of (poly)hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'-tetrahydroxybenzophenone 2,2',3,4,-4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxyphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-tridroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly)hydroxyphenylflavans such as 2,4,4-trimethyl-2',4',7-trihydroxy-2-phenylflavan, 2,4,4-trimethyl-2',4',5',6,7-pentahydroxy-2-phenylflavan and the like.

Other examples of photolatent acids which are suitable to be used in admixture with the compounds according to the present invention are described in JP-A-2003-43678, JP-A-2003-5372, JP-A-2003-43677, JP-A-2002-357904, JP-A-2002-229192.

The positive and negative photoresist composition of the present invention may optionally contain one or more additives (c) customarily used in photoresists in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers and organic basic compounds.

Further examples for organic basic compounds which can be used in the resist composition of the present invention are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups alkoxy groups, acyl groups acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoehtylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE 4408318, U.S. Pat. Nos. 5,609,989, 5,556,734, EP 762207, DE 4306069, EP 611998, EP 813113, EP 611998, and U.S. Pat. No. 5,498,506, JP-A-2003-43677, JP-A-2003-43678, JP-A-2002-226470, JP-A-2002-363146, JP-A-2002-363148, JP-A-2002-363152, JP-A-2003-98672, JP-A-2003-122013, JP-A-2002-341522. However, the organic basic compounds suitable in the present invention are not limited to these examples.

The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained. On the other hand, if it exceeds 10 parts by weight, reduced sensitivity and impaired developability at unexposed parts are liable to be caused.

The composition can further contain a basic organic compound which decomposes under actinic radiation ("suicide base") such as for example described in EP 710885, U.S. Pat. Nos. 5,663,035, 5,595,855, 5,525,453, and EP 611998.

Examples of dyes (c) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet (C142555), methyl violet (CI 42535), rhodamine B (CI 45170B), malachite green (CI 42000), and methylene blue (C152015).

Spectral sensitizers (e) may be further added to sensitize the photo latent acid to exhibit absorption in a region of longer wavelengths than far ultaviolet, whereby the photosensitive composition of the present invention can, for example, be rendered sensitive to an i-line or g-line radiation. Examples of suitable spectral sensitizers include 9,10-dialkoxyanthracene, benzophenones, p,p'-tetramethyldiaminobenzophenone, p,p'-tetraethylethylaminobenzophenone, thioxanthone, 2-chlorothioxanthone, anthrone, pyrene, perylene, phenothiazine, benzil, acridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonylcoumarin), 3-(aroylmethylene) thiazolines, eosin, rhodamine, erythrosine, and coronene. However, the suitable spectral sensitizers are not limited to these examples. These spectral sensitizers can be used also as light absorbers for absorbing the far ultraviolet emitted by a light source. In this case, the light absorber reduces light reflection from the substrate and lessens the influence of multiple reflection within the resist film, thereby diminishing the effect of standing waves.

Specific examples of such compounds are disclosed in WO 06/008251, page 36, line 30 to page 38, line 8, the disclosure of which is hereby incorporated by reference.

Further suitable additives (c) are "acid-amplifiers", compounds that accelerate the acid formation or enhance the acid concentration. Such compounds may also be used in combination with the sulfonium salts of the formula I according to the invention in positive or negative resists, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

Other additives (c) to improve the resist performance such as resolution, pattern profile, process latitude, line edge roughness, stability are described in JP-A-2002-122992, JP-A-2002-303986, JP-A-2002-278071, JP-A-2003-57827, JP-A-2003-140348, JP-A-2002-6495, JP-A-2002-23374, JP-A-2002-90987, JP-A-2002-91004, JP-A-2002-131913, JP-A-2002-131916, JP-A-2002-214768, JP-A-2001-318464, JP-A-2001-330947, JP-A-2003-57815, JP-A-2003-280200, JP-A-2002-287362, JP-A-2001-343750. Such compounds may also be used in combination with the sulfonium salts of the formula I according to the invention in positive or negative resists.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, butyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the sulfonium salts represented by formulae I according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyetheneleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 and F17.3 (manufactured by Dainippon Ink & Chemicals, Inc,. Japan), Fluorad FC 430 and FC431 (manufactured by Sumitomo 3M Ltd., Japan), Asahi Guard AG710 and Surflon S-382, SC101, SC102, SC103, SC104, SC105, and SC106 (manufactured by Asahi Grass Col, Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). Other examples are described in JP-A-2001-318459, JP-A-2002-6483. The added amount of the surfactant usually is 2 parts by weight or lower, desirably 0.5 part by weight or lower, per 100 parts by weight of the solid components of the composition of the present invention. The surfactants may be added alone or in combination of two or more thereof.

The solution is uniformly applied to a substrate by means of known coating methods, for example by spin-coating, immersion, knife coating, curtain pouring techniques, brush application, spraying and roller coating. It is also possible to apply the photosensitive layer to a temporary, flexible support and then to coat the final substrate by coating transfer (laminating). The amount applied (coating thickness) and the nature of the substrate (coating substrate) are dependent on the desired field of application. The range of coating thicknesses can in principle include values from approximately 0.01 μm to more than 100 μm.

After the coating operation generally the solvent is removed by heating, resulting in a layer of the photoresist on the substrate. The drying temperature must of course be lower than the temperature at which certain components of the resist might react or decompose. In general, drying temperatures are in the range from 60 to 160° C.

The resist coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the resist surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 pp. 275-281 and by K. P. Nicolay in Offset Printing 1997, 6, pp. 34-37. After the irradiation and, if necessary, thermal treatment, the irradiated sites (in the case of positive resists) or the non-irradiated sites (in the case of negative resists) of the composition are removed in a manner known per se using a developer.

In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1-0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve®/water.

Subject of the invention also is a process for the preparation of a photoresist by
(1) applying to a substrate a composition as described above;
(2) post apply baking the composition at temperatures between 60° C. and 160° C.;
(3) image-wise irradiating with light of wavelengths between 10 nm and 1500 nm;
(4) optionally post exposure baking the composition at temperatures between 60° C. and 160° C.; and
(5) developing with a solvent or with an aqueous alkaline developer.

Preferred is a process, wherein the image-wise irradiation is carried out with monochromatic or polychromatic radiation in the wavelength range from 150 to 450 nm, in particular in the range from 190 to 260 nm.

The photoresist compositions can be used on all substrates and with all exposure techniques known to the person skilled in the art. For example, semiconductor substrates can be used, such as silicon, gallium arsenide, germanium, indium antimonide; furthermore substrate covered by oxide or nitride layers, such as silicon dioxide, silicon nitride, titanium nitride, siloxanes, as well as metal substrates and metal coated substrates with metals such as aluminium, copper, tungsten, etc. The substrate can also be coated with polymeric materials, for example with organic antireflective coatings, insulation layers and dielectric coatings from polymeric materials prior to coating with the photoresist.

The photoresist layer can be exposed by all common techniques, such as direct writing, i.e. with a laser beam or projection lithography in step- and repeat mode or scanning mode, or by contact printing through a mask.

In case of projection lithography a wide range of optical conditions can be used such as coherent, partial coherent or incoherent irradiation. This includes off-axis illumination techniques, for example annular illumination and quadrupol illumination where the radiation is allowed to pass only certain regions of the lens, excluding the lens center.

The mask used to replicate the pattern can be a hard mask or a flexible mask. The mask can include transparent, semitransparent and opaque patterns. The pattern size can include also patterns which are at or below the resolution limit of the projection optics and placed on the mask in a certain way in order to modify the aerial image, intensity and phase modulation of the irradiation after having passed the mask. This includes phase shift masks and half-tone phase shift masks.

The patterning process of the photoresist composition can be used to generate patterns of any desired geometry and shape, for example dense and isolated lines, contact holes, trenches, dots, etc.

The photoresists according to the invention have excellent lithographic properties, in particular a high sensitivity, and high resist transparency for the imaging radiation.

Possible areas of use of the composition according to the invention are as follows: use as photoresists for electronics, such as etching resists, ion-implantation resist, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques, which are employed for various applications, for example, 3D optical information storage described in J. Photochem. Photobio. A, 158, 163 (2003), Chem. Mater. 14, 3656 (2002).

The composition according to the invention is also suitable for making inter-metal dielectrics layer, buffer layer, passivation coat of semiconductor devices and suitable for making waveguide for optoelectronics. For MEMS (micro electro mechanical systems) application, the composition according to the invention can be used as etching resist, mold for material deposition, and three dimensional objects of device itself. The coating substrates and processing conditions vary accordingly. Such example is described in U.S. Pat. No. 6,391,523.

The compounds of formula I according to the present invention, in combination with a sensitizer compound as described above, can also be used in holographic data storage (HDS) systems as for example described in WO 03/021358.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds of formula I as photolatent acid donors in compositions that can be crosslinked under the action of an acid and/or as dissolution enhancers in compositions wherein the solubility is increased under the action of an acid.

Subject of the invention further is a process of crosslinking compounds that can be crosslinked under the action of an acid, which method comprises adding a compound of formula I to the above-mentioned compounds and irradiating image-wise or over the whole area with light having a wavelength of 10-1500 nm.

The invention relates also to the use of compounds of formula I as photosensitive acid donors in the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential buildup layer of a printed circuit board, colour filters, chemically amplified resist materials, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fibre cable coatings, microelectronic circuits; as well as to method for the preparation for the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential build-up layer of a printed circuit board, colour filters, chemically amplified resist materials, image-recording materials, image-recording materials for recording holographic images, optical information storage or holo-graphic data storage, decolorizing materials, decolorizing materials for image recording materials, image recording materials using microcapsules, magnetic recording materials, micromechanical parts, plating masks, etch masks, glass fibre cable coatings, microelectronic circuits.

Subject of the invention is also the use of compounds of formula I as photosensitive acid donors in the preparation of colour filters or chemically amplified resist materials; as well as to a process for the preparation of colour filters or chemically amplified resist materials.

The invention further pertains to a color filter prepared by providing red, green and blue picture elements and a black matrix, all comprising a photosensitive resin and a pigment and/or dye on a transparent substrate and providing a transparent electrode either on the surface of the substrate or on the surface of the color filter layer, wherein said photosensitive resin comprises compounds of formula I as photosensitive acid donors.

The person skilled in the art is aware of suitable pigments or dyes to provide the color elements, as well as the black matrix and corresponding suitable resins as shown in, for examples, JP-A-9-203806, JP-A-10-282650, JP-A-10-333334, JP-A-11-194494, JP-A-10-203037, JP-A-2003-5371.

As already mentioned above, in photocrosslinkable compositions, sulfonium salts act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Sulfonium salts according to the present invention can also be used to produce so-called "print-out" images when the compound is used together with a colourant that changes colour when the pH changes, as described e.g. in JP Hei 4 328552-A or in U.S. Pat. No. 5,237,059. Such color-change systems can be used according to EP 199672 also to monitor goods that are sensitive to heat or radiation.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with sulfonium salts can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, sulfonium salts that are sparingly soluble in an aqueous-alkaline developer can be rendered soluble in the developer by means of light-induced conversion into the free acid, with the result that they can be used as solubility enhancers in combination with suitable film-forming resins.

The sulfonium salts of the present invention can also be used to shape polymers that undergo an acid induced transition into a state where they have the required properties using photolithography. For instance the sulfonium salts can be used to pattern conjugated emissive polymers as described, for example, in M. L. Renak; C. Bazan; D. Roitman; Advanced materials 1997, 9, 392. Such patterned emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics as they are used in sequential build up systems for printed circuit boards, stress buffer layers in the manufacturing of integrated circuits.

It is known that conjugated polymers like, e.g. polyanilines can be converted from semiconductive to conductive state by means of proton doping. The sulfonium salts of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

The composition according to the present invention, comprising a cationic photoinitiator of the formula I may also be employed in a vacuum deposition process as described in WO 02/064268. That is, the photoinitiators are suitable to be flash-evaporated vacuum-deposited. Accordingly, in a process for forming a solid poylmeric structure from flash-evaporated vacuum-deposited cationically curable monomeric material, comprising the steps (i) preparing a mixture of a cationically-curable monomer with a thermally stable, chemically inactive at room temperature, cationic photoinitiator;

(ii) flash-evaporating said mixture in a vacuum to produce a vapor;

(iii) condensing the vapor to produce a film; and (iv) exposing said film to a radiation source to produce a polymeric solid film, said photoinitiator is of the formula I as described above.

Suitable apparatus for said procedure, as well as details concerning the monomers are described in WO 02/064268, the teachings of which are incorporated by reference.

Suitable radiation sources for the compositions comprising compounds of formula I are radiation sources that emit radiation of a wavelength of approximately from 150 to 1500, for example from 180 to 1000, or preferably from 190 to 700 nanometers as well as e-beam radiation and high-energy electromagnetic radiation such as X-rays. Both, point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the radiation source and the substrate according to the invention to be irradiated can vary, for example, from 2 cm to 150 cm, according to the intended use and the type and/or strength of the radiation source. Suitable radiaiton sources are especially mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emit at different wavelengths throughout the whole spectrum either as small band emitting source or as broad band (white light) source. Also suitable are laser radiation sources, for example excimer lasers, such as Kr—F lasers for irradiation at 248 nm, Ar—F lasers at 193 nm, or $F_2$ laser at 157 nm. Lasers in the visible range and in the infrared range can also be used. Especially suitable is radiation of the mercury i, h and g lines at wavelengths of 365, 405 and 436 nanometers. As a light source further EUV (Extreme Ultra Violet) at 13 nm is also suitable. A suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the sulfonium salts in the composition in the irradiated sections of the surface coating decompose to form the acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

EXAMPLE 1

Preparation of

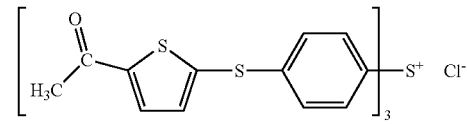

1.1: Preparation of the Intermediate 1a

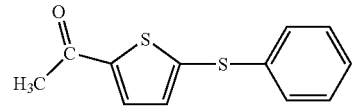

In a 350 ml reactor 25 g of 2-acetyl-5-bromothiophene are dissolved in 40 ml dimethylformamide and then 15.35 g of sodiumcarbonate are added. 15.9 g of thiophenol are added dropwise and the mixture is stirred for 6 h at 35° C. The reaction mass is poured on ice and extracted with ethyl acetate. After evaporation the product is obtained.

$^1$H-NMR data (ppm, CDCl$_3$): 7.53 1H d, 7.41-7.08 5H m, 7.07 1H d.

1.2: 13.2 g of aluminium chloride are suspended in 30 ml of dichloromethane. Then 12 g of the intermediate 1a (in 10 ml dichloromethane) are added dropwise at 0° C. To the reaction mixture are added dropwise 1.9 g of thionylchloride at −5° C., and the whole mass is stirred for 5 h at 25° C. The reaction mixture is then poured on ice and the organic phase is dried and evaporated. The product is purified by column chromatography.

¹H-NMR data (ppm, CDCl₃): 7.76 6H d, 7.68 3H d, 7.33 6H d, 7.29 3H d, 2.56 9H s.

EXAMPLE 2

Preparation of

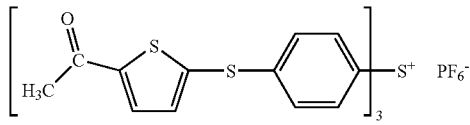

2.85 g of the compound of example 1 is dissolved in 10 ml dichloromethane and 1.02 g of potassium hexafluorophosphate is dissolved in 100 ml water. The two solutions are mixed together and stirred for 1 h at room temperature. Then the organic phase is separated, washed with water and dried and evaporated. The compound of example 2 is obtained.

¹H-NMR data (ppm, CDCl₃): 7.69 3H d, 7.47 6H d, 7.37-7.33 9H m, 2.55 9H s.

EXAMPLE 3

Preparation of

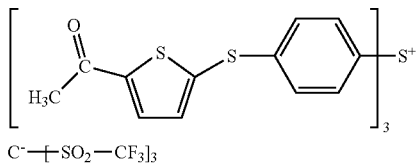

The compound is prepared from compound of example 1 according to the method as described in example 2, exchanging potassium hexafluorophosphate by lithium-tris(trifluoromethanesulfonyl)-methide.

¹H-NMR data (ppm, CDCl₃): 7.69 6H d, 7.42 6H d, 7.36 6H d, 7.34 6H d, 2.55 9H s.

EXAMPLE 4

Preparation of

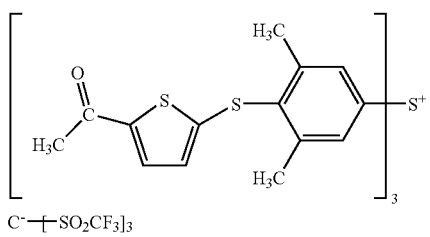

The compound is prepared according to the method as described in example 1 using the appropriate starting materials and exchanging potassium hexafluorophosphate by lithium-tris(trifluoromethanesulfonyl)-methide in the method as described in example 2.

¹H-NMR data (ppm, CDCl₃): 7.68 3H d, 7.42 6H d, 7.37-7.33 9H m, 2.55 9H s.

The compounds of the following examples 5-12 are prepared according to the method as described in example 1, optionally with an anion exchange as described in examples 2 or 3, by employing the appropriate intermediates.

EXAMPLE 5

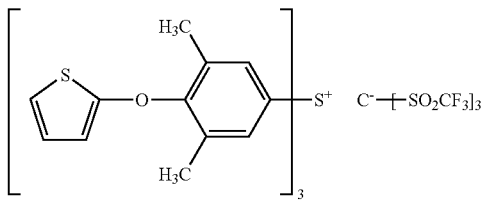

EXAMPLE 6

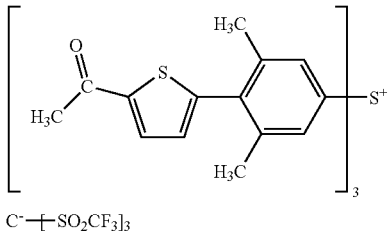

EXAMPLE 7

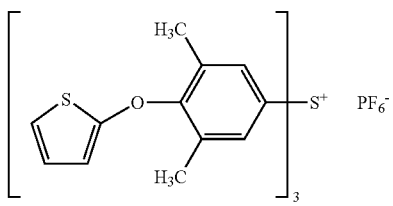

EXAMPLE 8

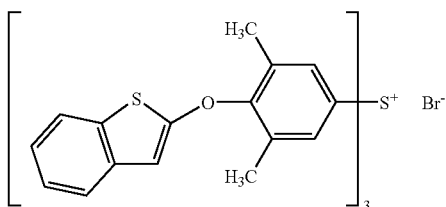

EXAMPLE 9

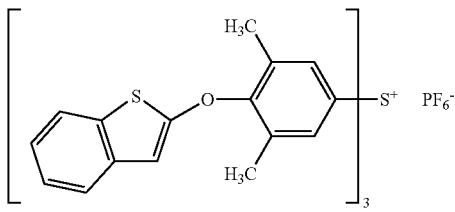

EXAMPLE 10

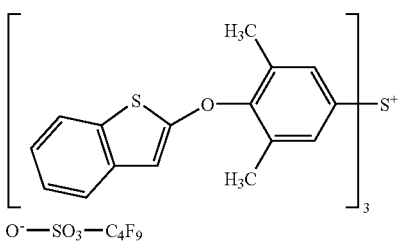

EXAMPLE 11

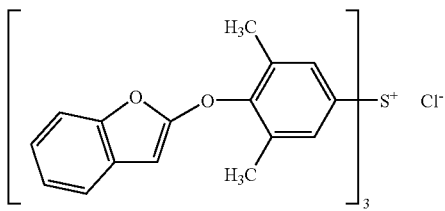

EXAMPLE 12

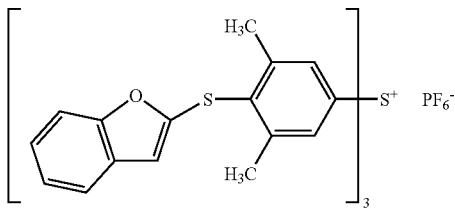

APPLICATION EXAMPLE A1

A composition is prepared by mixing the following components:

| | |
|---|---|
| 81.80 parts | of 3,4-epoxycyclohexylmethyl carboxylate (CYRACURE ® UVR 6105, provided by Dow Chemical) |
| 11.73 parts | of 3-ethyl-3-hydroxymethyl-oxetane (CYRACURE ® UVR 6000, provided by Dow Chemical) |
| 5.92 parts | of ε-caprolactone triol (Tone Polyol 301, provided by Dow Chemical) |
| 0.56 parts | of a silicon surface additive (Byk 307, provided by BYK) |
| 100.0 parts | overprint varnish, flexo ink basic formulation |

3% of the compound of example 2 is stirred into said formulation, which then is applied with a 4 μm wire bar onto an aluminum film of 85 μm thickness.

Curing is effected by moving the sample on a conveyor belt under a 1×120 W/cm medium pressure mercury lamp (IST) fitted with an aluminum reflector. A cured coating is obtained.

APPLICATION EXAMPLE A2

A chemically amplified negative resist formulation is prepared by mixing the following components:

| | |
|---|---|
| 100.00 parts | of an epoxy resin (SU-8 R 2002 provided by MicroChem., USA) |
| 245.00 parts | of cyclopentanone (ibidem) |
| 5.00 parts | of the photoacid generator (PAG) of example 3 |

The resist formulation is spin-coated onto a silicone wafer, on which chemical treatment with hexamethyldisilazane is applied beforehand, and soft-baked for 60 seconds at 95° C. on a hotplate to obtain a film thickness of 2 μm. The resist film is then exposed to UV radiation through V-42 and UV-D35 filters (provided by Asahi Technoglass, Japan) and a multi-density quartz mask using an Ushio's high-pressure mercury lamp, HB-25106AP, and a mask aligner Canon PLA-501 F. The samples then are post-exposure-baked for 120 seconds at 95° C. on a hotplate and developed. The dose ($E_{1:1}$), which is the dose just sufficient to give the same resist thickness after 60 seconds immersion development in ethyl lactate as the one before exposure, is determined from the measured contrast curve. The smaller the required dose the higher sensitive is the resist formulation. With the the compound of example 3 a dose to clear $E_{1:1}$ of 107 mJ/cm² is obtained.

The invention claimed is:
1. A compound of the formula I

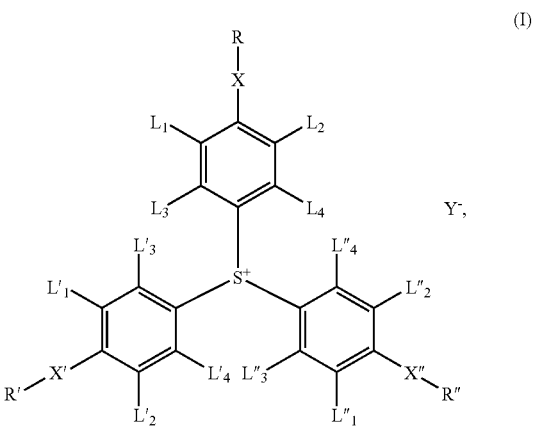

$L_1$, $L'_1$, $L''_1$, $L_2$, $L'_2$, $L''_2$, $L_3$, $L'_3$, $L''_3$, $L_4$, $L'_4$ and $L''_4$ independently of one another are hydrogen, $R_1$, $OR_1$, $SR_1$, $NR_1R_2$, halogen, $NO_2$, $CN$, $NR_1COR_2$, $COOR_1$, OCOR$_1$, CONR$_1$R$_2$, OCOOR$_1$, OCONR$_1$R$_2$, NR$_1$COOR$_2$, SO$_3$H, SO$_3$M, SOR$_1$, SO$_2$R$_1$, COOT or COT;

R and R' and R" independently of each another are C$_3$-C$_{20}$heteroaryl selected from the group consisting of thienyl, furyl, benzo[b]thienyl, naphtho[2,3-b]thienyl, thianthrenyl, benzofuryl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl and 10-methyl-2-phenoxazinyl, wherein all of said C$_3$-C$_{20}$heteroaryl are unsubstituted or substituted by one or more halogen, C$_1$-C$_4$alkyl or COT; and wherein the case that the C$_3$-C$_{20}$heteroaryl comprises an annelated benzene ring, the bond to the corresponding X, X' or X" is not located on said annelated ring;

X, X' and X" independently of each other are O, S, CR$_a$R$_b$, single bond, NR$_a$ or NCOR$_a$;

T is hydrogen, C$_1$-C$_{20}$alkyl, C$_1$-C$_{20}$alkyl substituted by one or more D, C$_2$-C$_{20}$alkyl interrupted by one or more E, C$_2$-C$_{20}$alkyl substituted by one or more D and interrupted by one or more E; or T is C$_3$-C$_{12}$cycloalkyl, C$_3$-C$_{12}$cycloalkyl substituted by one or more D, C$_2$-C$_{12}$cycloalkyl interrupted by one or more O, CO, COO, CONR$_5$, S or NR$_5$, C$_2$-C$_{12}$cycloalkyl substituted by one or more D and interrupted by one or more O, CO, COO, CONR$_5$, S or NR$_5$; or T is C$_2$-C$_{20}$alkenyl, C$_2$-C$_{20}$alkenyl substituted by one or more D, C$_3$-C$_{20}$alkenyl interrupted by one or more E, C$_3$-C$_{20}$alkenyl substituted by one or more D and interrupted by one or more E, C$_5$-C$_{12}$cycloalkenyl, C$_5$-C$_{12}$cycloalkenyl substituted by one or more D, C$_3$-C$_{12}$cycloalkenyl interrupted by one or more O, CO, COO, CONR$_5$, S or NR$_5$, C$_3$-C$_{12}$cycloalkenyl substituted by one or more D and interrupted by one or more O, CO, COO, CONR$_5$, S or NR$_5$; or T is C$_2$-C$_{20}$alkinyl, C$_2$-C$_{20}$alkinyl substituted by one or more D; C$_4$-C$_{20}$alkinyl interrupted by one or more O, CO, COO, CONR$_5$, S or NR$_5$, C$_4$-C$_{20}$alkinyl substituted by one or more D and interrupted by one or more O, CO, COO, CONR$_5$, S or NR$_5$; or T is C$_7$-C$_{12}$bicycloalkyl, C$_7$-C$_{12}$bicycloalkyl substituted by one or more D, C$_5$-C$_{12}$bicyclo-alkyl interrupted by one or more O, CO, COO, CONR$_5$, S or NR$_5$, C$_5$-C$_{12}$bicycloalkyl substituted by one or more D and interrupted by one or more O, CO, COO, CONR$_5$, S or NR$_5$; or T is C$_7$-C$_{12}$bicycloalkenyl, C$_7$-C$_{12}$bicycloalkenyl substituted by one or more D, C$_5$-C$_{12}$ bicycloalkenyl interrupted by one or more O, CO, COO, CONR$_5$, S or NR$_5$, C$_5$-C$_{12}$bicycloalkenyl substituted by one or more D and interrupted by one or more O, CO, COO, CONR$_5$, S or NR$_5$; or T is C$_{10}$-C$_{20}$tricycloalkyl, C$_6$-C$_{12}$tricycloalkyl substituted by one or more D, C$_7$-C$_{15}$tricycloalkyl interrupted by one or more O, CO, COO, CONR$_5$, S or NR$_5$, C$_7$-C$_{15}$tricycloalkyl substituted by one or more D and interrupted by one or more O, CO, COO, CONR$_5$, S or NR$_5$; or T is C$_8$-C$_{18}$cycloalkylenaryl, C$_8$-C$_{18}$cycloalkylenaryl substituted by one or more D, C$_7$-C$_{18}$cycloalkylenaryl interrupted by one or more O, CO, COO, CONR$_5$, S or NR$_5$, C$_7$-C$_{18}$cycloalkylenaryl substituted by one or more D and interrupted by one or more O, CO, COO, CONR$_5$, S or NR$_5$; or T is C$_7$-C$_{18}$cycloalkylenheteroaryl, C$_7$-C$_{18}$cycloalkylenheteroaryl substituted by one or more D, C$_6$-C$_{18}$cycloalkylenheteroaryl interrupted by one or more O, CO, COO, CONR$_5$, S or NR$_5$, C$_6$-C$_{18}$cycloalkylenheteroaryl substituted by one or more D and interrupted by one or more O, CO, COO, CONR$_5$, S or NR$_5$; or T is C$_6$-C$_{14}$aryl, C$_6$-C$_{14}$aryl substituted by one or more D, C$_3$-C$_{12}$heteroaryl or C$_3$-C$_{12}$heteroaryl substituted by one or more D;

R$_1$, R$_2$, R$_a$ and R$_b$ independently of one another have the meaning of T;

D is hydrogen, R$_5$, OR$_5$, SR$_5$, NR$_5$R$_6$, halogen, NO$_2$, CN, O-glycidyl, O-vinyl, O-allyl, COR$_5$, NR$_5$COR$_6$, COOR$_5$, OCOR$_5$, CONR$_5$R$_6$, OCOOR$_5$, OCONR$_5$R$_6$, NR$_5$COOR$_6$, SO$_3$H, SO$_3$M, =O, C$_6$-C$_{14}$aryl, C$_6$-C$_{14}$aryl substituted by one or more R$_{12}$, OR$_{12}$, halogen, SR$_{12}$, NO$_2$, CN, COR$_{12}$, NR$_{12}$COR$_{13}$, COOR$_{12}$, OCOR$_{12}$, CONR$_{12}$R$_{13}$, OCOOR$_{12}$, OCONR$_{12}$R$_{13}$, NR$_{12}$COOR$_{13}$ or SO$_3$H, C$_3$-C$_{12}$heteroaryl, C$_3$-C$_{12}$heteroaryl substituted by one or more R$_{12}$, OR$_{12}$, halogen, SR$_{12}$, NO$_2$, CN, COR$_{12}$, NR$_{12}$COR$_{13}$, COOR$_{12}$, OCOR$_{12}$, CONR$_{12}$R$_{13}$, OCOOR$_{12}$, OCONR$_{12}$R$_{13}$, NR$_{12}$COOR$_{13}$ or SO$_3$H; or is C$_3$-C$_{12}$cycloalkyl, C$_3$-C$_{12}$cycloalkyl substituted by one or more R$_{14}$, C$_2$-C$_{12}$cycloalkyl interrupted by one or more O, CO, COO, CONR$_5$, S or NR$_5$, C$_2$-C$_{12}$cycloalkyl substituted by one or more $R_{14}$ and interrupted by one or more O, CO, COO, $CONR_5$, S or $NR_5$; or D is $C_5$-$C_{12}$cycloalkenyl, $C_5$-$C_{12}$cycloalkenyl substituted by one or more $R_{14}$, $C_3$-$C_{12}$cycloalkenyl interrupted by one or more O, CO, COO, $CONR_5$, S or $NR_5$, $C_3$-$C_{12}$cycloalkenyl substituted by one or more $R_{14}$ and interrupted by one or more O, CO, COO, $CONR_5$, S or $NR_5$; or D is $C_7$-$C_{12}$bicycloalkyl, $C_7$-$C_{12}$bicycloalkyl substituted by one or more $R_{14}$, $C_5$-$C_{12}$bicycloalkyl interrupted by one or more O, CO, COO, $CONR_5$, S or $NR_5$, $C_5$-$C_{12}$bicycloalkyl substituted by one or more $R_{14}$ and interrupted by one or more O, CO, COO, $CONR_5$, S or $NR_5$; or D is $C_7$-$C_{12}$bicycloalkenyl, $C_7$-$C_{12}$bicycloalkenyl substituted by one or more $R_{14}$, $C_5$-$C_{12}$bicycloalkenyl interrupted by one or more O, CO, COO, $CONR_5$, S or $NR_5$, $C_5$-$C_{12}$bicycloalkenyl substituted by one or more $R_{14}$ and interrupted by one or more O, CO, COO, $CONR_5$, S or $NR_5$; or D is $C_{10}$-$C_{20}$tricycloalkyl, $C_{10}$-$C_{20}$tricycloalkyl substituted by one or more $R_{14}$, $C_7$-$C_{15}$tricycloalkyl interrupted by one or more O, CO, COO, $CONR_5$, S or $NR_5$, $C_6$-$C_{12}$tricycloalkyl substituted by one or more $R_{14}$ and interrupted by one or more O, CO, COO, $CONR_5$, S or $NR_5$; or is $C_8$-$C_{18}$cycloalkylenaryl, $C_8$-$C_{18}$cycloalkylenaryl substituted by one or more $R_{14}$, $C_7$-$C_{18}$cycloalkylenaryl interrupted by one or more O, CO, COO, $CONR_5$, S or $NR_5$, $C_7$-$C_{18}$cycloalkylenaryl substituted by one or more $R_{14}$ and interrupted by one or more O, CO, COO, $CONR_5$, S or $NR_5$; or $C_7$-$C_{18}$cycloalkylenheteroaryl, $C_7$-$C_{18}$cycloalkylenheteroaryl substituted by one or more $R_{14}$, $C_8$-$C_{18}$cycloalkylenheteroaryl interrupted by one or more O, CO, COO, $CONR_5$, S or $NR_5$, $C_8$-$C_{18}$cycloalkylenheteroaryl substituted by one or more $R_{14}$ and interrupted by one or more O, CO, COO, $CONR_5$, S or $NR_5$;

E is O, S, COO, OCO, CO, $NR_5$, $NCOR_5$, $NR_5CO$, $CONR_5$, OCOO, $OCONR_5$, $NR_5COO$, $SO_2$, SO, $CR_5$=$CR_6$ or

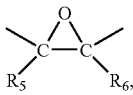

is $C_6$-$C_{14}$arylene, $C_3$-$C_{12}$heteroarylene, $C_3$-$C_{12}$cycloalkylene, $C_3$-$C_{12}$cycloalkylene substituted by one or more $R_{14}$, $C_2$-$C_{12}$cycloalkylene interrupted by one or more O, CO, COO, $CONR_5$, S or $NR_5$, $C_2$-$C_{12}$cycloalkylene substituted by one or more $R_{14}$ and interrupted by one or more O, CO, COO, $CONR_5$, S or $NR_5$; or E is $C_5$-$C_{12}$cycloalkenylene, $C_5$-$C_{12}$cycloalkenylene substituted by one or more $R_{14}$, $C_3$-$C_{12}$cycloalkenylene interrupted by one or more O, CO, COO, $CONR_5$, S or $NR_5$, $C_3$-$C_{12}$cycloalkenylene substituted by one or more $R_{14}$ and interrupted by one or more O, CO, COO, $CONR_5$, S or $NR_5$; or E is $C_7$-$C_{12}$bicycloalkylene, $C_7$-$C_{12}$bicycloalkylene substituted by one or more $R_{14}$, $C_5$-$C_{12}$bicycloalkylene interrupted by one or more O, CO, COO, $CONR_5$, S or $NR_5$, $C_5$-$C_{12}$bicycloalkylene substituted by one or more $R_{14}$ and interrupted by one or more O, CO, COO, $CONR_5$, S or $NR_5$; or E is $C_7$-$C_{12}$bicycloalkenylene, $C_1C_{12}$bicycloalkenylene substituted by one or more $R_{14}$, $C_5$-$C_{12}$bicycloalkenylene interrupted by one or more O, CO, COO, $CONR_5$, S or $NR_5$, $C_5$-$C_{12}$bicycloalkenylene substituted by one or more $R_{14}$ and interrupted by one or more O, CO, COO, $CONR_5$, S or $NR_5$; or E is $C_{10}$-$C_{20}$tricycloalkylene, $C_{10}$-$C_{20}$tricycloalkylene substituted by one or more $R_{14}$, $C_7$-$C_{15}$tricycloalkylene interrupted by one or more O, CO, COO, $CONR_5$, S or $NR_5$, $C_7$-$C_{15}$tricycloalkylene substituted by one or more $R_{14}$ and interrupted by one or more O, CO, COO, $CONR_5$, S or $NR_5$; or E is $C_8$-$C_{18}$cycloalkylenarylene, $C_8$-$C_{18}$cycloalkylenarylene substituted by one or more $R_{14}$, $C_7$-$C_{18}$cycloalkylenarylene interrupted by one or more O, CO, COO, $CONR_5$, S or $NR_5$, $C_7$-$C_{18}$cycloalkylenarylene substituted by one or more $R_{14}$ and interrupted by one or more O, CO, COO, $CONR_5$, S or $NR_5$; or E is $C_7$-$C_{18}$cycloalkylenheteroarylene,
$C_7$-$C_{18}$cycloalkylenheteroarylene substituted by one or more $R_{14}$, $C_6$-$C_{18}$cycloalkylenheteroarylene interrupted by one or more O, CO, COO, $CONR_5$, S or $NR_5$, $C_6$-$C_{18}$cycloalkylenheteroarylene substituted by one or more $R_{14}$ and interrupted by one or more O, CO, COO, $CONR_5$, S or $NR_5$;

$R_5$ and $R_6$ independently of one another are hydrogen, a covalent bond to another substituent to form a ring, $C_1$-$C_6$ alkylene to form a ring with another substituent, $C_1$-$C_{12}$alkyl, phenyl or phenyl substituted by $C_1$-$C_4$alkyl and/or $C_1$-$C_4$alkoxy;

$R_7$, $R_8$, $R_9$, $R_{10}$ and $R_{11}$ independently of one another are hydrogen, $C_1$-$C_{12}$alkyl, $C_1$-$C_{12}$alkoxy, phenyl, phenoxy, substituted phenyl or substituted phenoxy;

$R_{12}$ and $R_{13}$ independently of one another are hydrogen, $C_1$-$C_{12}$alkyl, $C_5$-$C_{12}$cycloalkyl or phenyl;

$R_{14}$ is hydrogen, $C_1$-$C_{12}$alkyl, $C_5$-$C_{12}$cycloalkyl, $C_1$-$C_{12}$alkoxy, $C_2$-$C_{12}$cycloalkyloxy,phenyl or halogen;

n is an integer from 1 to 100;

Y is an inorganic or organic anion;

M is an inorganic or organic cation.

2. A compound of the formula Ia according to claim 1, wherein $L_3$ and $L_4$ are hydrogen; and $L_1$, $L_2$ independently of one another are hydrogen or $C_1$-$C_4$alkyl;

L is hydrogen, $R_1$, $OR_1$, $SR_1$, halogen, $NO_2$, CN, $COOR_1$, $OCOR_1$, $OCOOR_1$, COOT or COT;

X is O, S, $CR_aR_b$ or a single bond, provided that if X is O, R is not pyridinyl; and $R_1$ has one of the meanings given for T.

3. A compound of the formula I according claim 1, wherein R and R' and R" as $C_3$-$C_{20}$heteroaryl are thienyl, furyl, benzo[b]thienyl, naphtho[2,3-b]thienyl, thianthrenyl, benzofuryl, dibenzofuryl, chromenyl, xanthenyl, thioxanthenyl, phenoxathiinyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl;

wherein all said $C_3$-$C_{20}$heteroaryl are unsubstituted or substituted by one or more halogen, $C_1$-$C_4$alkyl or COT; and wherein the case that the $C_3$-$C_{20}$heteroaryl comprises an annelated benzene ring, the bond to the corresponding X, X' or X" is not located on said annelated ring.

4. A compound of the formula I according to claim 1, wherein

R and R' and R" as $C_3$-$C_{20}$heteroaryl are thienyl or furyl, both of which are unsubstituted or are substituted by at least one $C_1$-$C_4$alkyl and/or COT.

* * * * *